US010457643B2

(12) United States Patent
Herzon et al.

(10) Patent No.: US 10,457,643 B2
(45) Date of Patent: Oct. 29, 2019

(54) (−)-HUPERZINE A PROCESSES AND RELATED COMPOSITIONS AND METHODS OF TREATMENT

(71) Applicant: Yale University, New Haven, CT (US)

(72) Inventors: Seth Herzon, New Haven, CT (US); Maung Kyaw Moe Tun, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/848,350

(22) Filed: Dec. 20, 2017

(65) Prior Publication Data

US 2018/0237395 A1   Aug. 23, 2018

Related U.S. Application Data

(62) Division of application No. 14/003,213, filed as application No. PCT/US2012/025628 on Feb. 17, 2012, now Pat. No. 10,059,672.

(60) Provisional application No. 61/449,198, filed on Mar. 4, 2011.

(51) Int. Cl.
*C07D 221/22* (2006.01)
*A61K 31/439* (2006.01)
*C07F 7/10* (2006.01)

(52) U.S. Cl.
CPC .......... *C07D 221/22* (2013.01); *A61K 31/439* (2013.01); *C07F 7/10* (2013.01)

(58) Field of Classification Search
CPC ........ C07D 221/22; A61K 31/439; C07F 7/10
USPC ....................................................... 514/295
See application file for complete search history.

(56) References Cited

U.S. PATENT DOCUMENTS

| 5,104,880 A | 4/1992 | Kozikowski |
| 6,271,379 B1 | 8/2001 | Tuckmantel et al. |
| 2009/0247754 A1 | 10/2009 | Underiner et al. |
| 2009/0275751 A1 | 11/2009 | Nagato et al. |
| 2010/0234416 A1 | 9/2010 | Schachter et al. |

FOREIGN PATENT DOCUMENTS

WO   1999/011625   11/1999

OTHER PUBLICATIONS

Tun, MKM; Wustmann, DJ; Herzon, SB. A robust and scalable synthesis of the potent neuroprotective agent (−)-Huperzine A. Chemical Science, 2011;2:2251-2253.
Wallis ES, Lane JF. The Hofmann Reaction. Organic Reactions, p. 267-306. Published Online: Mar. 15, 2011 DOI: 10.1002/0471264180. or003.07.
Shiori. The Hofman Reaction. Degradation Reactions, p. 800-806.
Radlick P, Brown LR. A Versatile Modification of the Hofmann Rearrangement. Communications, 1974;290-292.
Farid U, Wirth T. Highly Stereoselective Metal-Free Oxyaminations Using Chiral Hypervalent Iodine Reagents. Angew Chem Int Ed, 2012;51:3462-3465.
Serna S, et al. Iodine(III)—mediated aromatic amidation vs olefin amidohydroxylation. The amide N-substituent makes the difference. Tetrahedron, 2004;60:6533-3539.
Celik M, et al. Letters, Synthesis of 2006;47:3659-3663 diols using the hypervalent iodine(IIf) reagent, phenyliodine (III) bis(trfluoroacetate). Tetrahedron Letters, 2006;47:3659-3663.
Tellitu I, Dominguez E. On the regiosefectivity of the PI FA-mediated bis(trifluoroacetoxylation) of styrene-type compounds. Tetrahedron, 2008;64:2465-2470.
Loudon GM, et al. Conversion of Aliphatic Amides into Amines with [1,1-Bid(trifluoroacetoxy)iodo]benzene. 1. Scope of the Reaction. J Org Chem, 1984;49:4272-4276.
Kaneko S, et al. Synthetic Studies of Huperzine and Its Fluorinated Analogues. 1. Novel Asymmetric Syntheses of an Enantiomeric Pair of Huperzine A 1. Tetrahedron, 1998;54:54 71-5484.
Kozikowski AP, et al. Synthesis and Biological Evaluation of (+/−)-Z-Huperzine A. Tetrahedron Letters, 1990;31 (43):6159-6162.
Kozikowski AP, et al. Synthesis of Huperzine A and Its Analogues and Their Anticholinesterase Activity. J Org Chem, 1991 ;56:4636-4645.
Greene TW, Wuts PGM. Protective Groups in Organic Synthesis, 3rd ed; Wiley; New York, 1999.
Zhang L, et al. Rearrangement of N(alpha)-protected L-Asparagines with Iodosobenzene Diacetate. A Practical Route to Beta-Amino-L-alanine Derivatives. J Org Chem, 1997;62:6918-6920.
Schmuck C, Geiger L. Design and synthesis of a new class of arginine analogues with an improved anion binding site in the side chain. Chem Comm, 2005;772-774.
Nicolaou KC, et al. Chemistry and Biology of Diazonamide A: First Total Synthesis and Confirmation of the True Structure. J Am Chem Soc, 126;12888-12896.
Fleming I. Silyl-to-Hydroxy Conversion in Organic Synthesis. Chemtracts-Organic Chemistry, 1996;9:1-64.
Jones GR, et al. Tetrahedron Report No. 401. Tetrahedron, 1996;52:7599-7662.
Maryanoff BE, Reitz AB. The Wittig Olefination Reaction and Modifications Involving Phosphoryl-Stabilized Carbanions. Stereochemistry, Mechanism, and Selected Synthetic Aspects. Chem Rev, 1989;89:863-927.
Edmonds M, Abell A. The Wittig Reaction. Modern Carbonyl Olefination, 2004;1-17.
Nicolaou KC, et al. The Wittig and Related Reactions in Natural Product Synthesis. Liegis Ann Chem, 1997:1283-1301.

(Continued)

*Primary Examiner* — Rita J Desai
(74) *Attorney, Agent, or Firm* — Henry D. Coleman; R. Neil Sudol

(57) ABSTRACT

The invention provides (1) processes for making substantially-pure (−) huperzine A and substantially-pure (−) huperzine A derivatives; (2) compositions useful in making substantially-pure (−) huperzine A and substantially-pure (−) huperzine A derivatives; and (3) methods of treating or preventing neurological disorders using substantially-pure (−) huperzine A and substantially-pure (−) huperzine A derivatives.

10 Claims, 26 Drawing Sheets

(56) References Cited

OTHER PUBLICATIONS

Still WC, Kahn M, Mitra A. Rapid Chromatographic Technique for Preparative Separations with Moderate Resolution. J Org Chem, 1978;43:2923-2925.

Pangborn AB, et al. Safe and Convenient Procedure for Solvent Purification. Organometallics, 1996;15:1518-1520.

Fleming I, Roberts S, Smith SC. The preparation and analysis of the phenyldimethylsilyllithium reagent and its reation with silyl enol ethers. J Chem Soc Perkin Trans I, 1998;1209-1214.

Lee HW, et al. Convenient and Practical Synthesis of (R)-(+)-4-Methyl-2-cyclohexen-1-one. J Org Chem, 1996;61 :2542-2543.

Kelly SA, et al. A convergent approach to huperzine A and analogues. Org Biomol Chem, 2003;1 :2865-2876.

Dai C, Fu GC. The First General Method for Palladium-Catalyzed Negishi Cross-Coupling of Aryl and Vinyl Chlorides: Use of Commercially Available Pd(P(t-Bu)3)2 as a Catalyst. J Am Chem Soc, 2001 ;123:2719-2724.

Burgess EM, Penton HR, Taylor EA. Thermal Reactions of Alkyl N-Carbomethoxysulfamate Esters. J Org Chem, 1973;38:26-31.

Ghaffar T, Parkins AW. The catalytic hydration of nitriles to amides using a homogeneous platinum phosphinito catalyst. J Mol Catal A, 2000;160-249.

Yamada F, et al. A Route to optically Pure (−)-Huperzine A: Molecular Modelling and in Vitro Pharmacology. J Am Chem Soc, 1991;113:4695-4696.

Liu JS, et al. The structures of huperzine A and 8, two new alkaloids exhibiting marked anticholinesterase activity. Can D J Chem, 1986;64:837-839.

Kozikowski AP, Tuckmantel W. Chemistry, Pharmacology, and Clinical Efficacy of the Chinese Nootropic Agent Huperzine A. Ace Chem Res, 1999;32:641-650.

Wang YE, Yue DX, Tang XC. Anti-cholinesterase activity of huperzine A. Acta Pharmacol Sin, 1986;7:110-113.

Raves ML, et al. Structure of acetylcholinesterase complexed with the nootropic alkaloid, (−)-huperzine A. Nat Struct Biol, 1997;4:57-63.

Lallement G, et al. Subchronic Administration of Pyridostigmine or Huperzine to Primates: Compared Efficacy Against Soman Toxicity. Drug Chem Toxicol, 2002;25:309-320.

Gordon R, et al. Oral administration of pyridostigmine bromide and huperzine A protects human whole blood cholinesterases from ex vivo exposure to soman. Chem Biol Interact, 2005;157-158:239-246.

Haigh J, et al. Protection of red blood cell acetylcholinesterase by oral huperzine A against ex vivo soman exposure: Next generation prophylaxis and sequestering of acetylcholinesterase over butyrylcholinesterase. Chem Biol Interact, 2008;175:380-386.

Karasova JZ, et al. Pretreatment with Huperzine A Protects Acetylcholinesterase in the Rate Brain Against Inhibition by VX and Russian VX. Lett Drug Des Discovery, 2009;6:563-567.

Lallement G, et al. Review of the Value of Huperzine as Pretreatment of Organophosphate Poisoning. NeuroToxicology, 2002;23:1-5.

Bai DL, Tang C, He XC. Huperzine A, A Potential Therpeutic Agent for Treatment of Alzheimer's Disease.Curr Med Chem, 2000;7:355-374.

Wang R, Yan H, Tang XC. Progress in studies of Huperzine A, a natural cholinesterase inhibitor from Chinese herbal medicine. Acta Pharmacol Sin, 2006;27:1-26.

Zhang HY, Tang XC. Neuroprotective effects of huperzine A: new therapeutic targets for neurodegenerative disease. Trends Pharmacol Sci, 2006;27:619-625.

Zhang HY, et al. Potential therapeutic targets of huperzine A for Alzheimer's disease and vascular dementia. Chem Biol Interact, 2008;175:396-402.

Utile JT, Walsh S, Aisen PS. An update on huperzine A as a treatment for Alzheimer's disease. Expert Opin Invest Drugs, 2008;17:209-215.

Max, Tan C, Zhu D, Gang DR. A survey of potential huperzine A natural resources in China: The Huperziaceae. Ethnopharmacol, 2006;104:54-67.

Xi-Can T, Kindel H, Kozikowski AP, Hanin I. Comparison of the effects of natural and synthetic huperzine-A on rat brain cholinergic function in vitro and in vivo. Ethnopharmacol, 1994;44: 147.

Xin Y, Kozikowski AP. A Practical Synthesis of the Chinese "Nootropic" Agent Huperzine A: A Possible Lead in the Treatment of Alzheimer's Disease. H Am Chem Soc, 1989; 111 :4116-4117.

Kaneko S, Yoshino T, Katoh T, Terashima S. An Enantioselective Synthesis of Natural (−)-Huperzine A via Cinchona Alkaloids-Promoted Asymmetric Michael Reaction. Heterocycles, 1997;46:27-30.

Kaneko S, Yoshino T, Katoh T, Terashima S. A novel enantioselective synthesis of the key intermediate of(−)-huperzine A employing asymmetric palladium-catalyzed bicycloannulation. Tetrahedron: Asymmetry, 1997;8:829-832.

Kaneko S, Yoshino T, Katoh T, Terashima S. Synthetic Studies of Huperzine A and Its Fluorinated Analogues. 1. Novel Asymmetric Syntheses of an Enantiomeric Pair of Huperzine A. Tetrahedron, 1998;54:5471-5484.

Chassaing C, Haudrechy A, Langlois Y. Asymmetric palladium annulation: formal synthesis of (+)-huperzine A. Tetrahedron Lett, 1999;40:8805-8809.

He XC, Wang B, Yu G, Bai D. Studies on the asymmetric synthesis of huperzine A. Part 2: Highly enantioselective palladium-catalyzed bicycloannulation of the beta-keto-ester using new chiral ferrocenylphosphine ligands. Tetrahedron: Asymmetry, 2001 ;12:3213-3216.

Pan QB, Ma DW. Chiral Guanidine Catalyzed Annulation to the Core Structure of(−)-Huperzine A. Chin J Chem, 2003;21 :793-796.

Koshiba T, Yokoshima S, Fukuyama T. Total Synthesis of (−)-Huperzine A. Org Lett, 2009;11:5354-5356.

Ward J, Caprio V. A radical mediated approach to the core structure of huperzine A. Tetrahedron Lett, 2006;47:553-556.

Haudrechy A, Chassaing C, Riche C, Langlois Y. A Formal Synthesis of (+)-Huperzine A. Tetrahedron, 2000;56:3181-3187.

Lee YC, Jung MH, Lee HW, Yang JY. Synthesis of huperzine intermediates via Mn(III)—mediated radical cyclization. Tetrahedron Lett, 2002;43:2407-2409.

Lucey C, Kelly SA, Mann J. A concise and convergent (formal) total synthesis of huperzine A. Org Biomol Chem, 2007;5:301-306.

Kozikowski AP, Reddy ER, Miller CP. A Simplified Route to a Key Intermediate in the Synthesis of the Chinese Nootropic Agent Huperzine A. J Chem Soc Perkin Trans, 1990;1:195-197.

Lee HW, Ji SK, Lee YC, Lee JH. Convenient and Practical Synthesis of (R)-(+)-4-Methyl-2-cyclohecen-1-one. J Org Chem, 1996;61 ;2542-2543.

Bertozzi F, et al. A Multigram, Catalytic and Enantioselective Synthesis of Optically Active 4-Methyl-2-cyclohexen-1-one: a Useful Chiral Building Block. Synthesis, 2001 ;483-486.

Naasz R, et al. Highly Enantioselective Copper-Phosphoramidite Catalyzed Kinetic Resolution of Chiral 2-Cyclohexenones. Chem Int Ed, 2001 ;40:927-930.

Bisai V, Sarpong R. Methoxypyridines ni the Synthesis of Lycopodium Alkaloids: Total Synthesis of(+−)-Lycoposerramine R. Org Lett, 2010; 12:2551-2553.

Kahne D, Collum DB. Kinetic Cyanations of Ketone Enolates. Tetrahedron Lett, 1981;22:5011-5014.

Kawatsura M, Hartwig JF. Simple, Highly Active Palladium Catalysts for Ketone and Malonate Arylation: Dissecting the Importance of Chelation and Steric Hindrance. J Am Chem Soc, 1999; 121 :1473-1478.

Fox JM, Huang X, Chieffi A, Buchwald SL. Highly Active and Selective Catalysts for the Formation of alpha-Aryl Ketones.J Am Chem Soc, 2000;122:1360.

Bellina F, Rossi R. Transition Metal-Catalyzed Direct Arylation of Substrates with Activated sp3-Hybridized C—H Bonds and Some of Their Synthetic Equivalents with Aryl Halides and Pseudohalides. Chem Rev, 2010;110:1082-1146.

Reitz AB, et al. Dramatic Concentration Dependence of Stereochemistry in the Wittig Reaction. Examination of the Lithium Salt Effect. J Org Chem, 1986;51 :3302-3308.

(56) References Cited

OTHER PUBLICATIONS

Ghaffar T, Parkins AW. The catalytic hydration of nitriles to amides using a homogeneous platinum phosphinito catalyst. J Mol Cata! A: Chem, 2000;160:249-261.
Kozikowski A, et al. Synthesis of Huperzine A and Its Analogues and Their Anticholinesterase Activity. J Org Chem, 1991;56:4636-4645.
Kozikowski AP, et al. Synthesis and Biological Evaluation of (plus or mines)-Z-Huperzine A. Tetrahedron Letters, 1990;31(43):6159-6162.

| Position | ¹H NMR Synthetic 1 (CDCl₃) | ¹H NMR Natural 1 (CDCl₃) | ¹³C NMR Synthetic 1 (CDCl₃) | ¹³C NMR Natural 1 (CDCl₃) |
|---|---|---|---|---|
| |  (−)-huperzine A (1) | | | |
| 1 | 7.88 (d, $J$ = 9.5 Hz) | 7.84 (d, $J$ = 9.0 Hz) | 140.3 | 140.3 |
| 2 | 6.37 (d, $J$ = 9.0 Hz) | 6.38 (d, $J$ = 9.0 Hz) | 117.1 | 117.0 |
| 3 | 13.25 (br s) | 13.20 (br s) | | |
| 4 | 2.86 (dd, $J$ = 17.0, 5.0 Hz) | 2.76 | 35.4 | 35.2 |
| 4 | 2.73 (dd, $J$ = 16.5, 1.0 Hz) | 2.76 | 35.4 | 35.2 |
| 5 | 3.59–3.55 (m) | 3.56 (m) | 33.0 | 33.0 |
| 6 | 5.38 (d, $J$ = 4.5 Hz) | 5.38 (d, $J$ = 5.0 Hz) | 124.4 | 124.4 |
| 7 | 2.12 (br s) | 2.12 (s) | 49.2 | 49.3 |
| 8 | 1.51 (s) | 1.46 (s) | 22.7 | 22.6 |
| 9 | 5.46 (q, $J$ = 6.5 Hz) | 5.46 (q, $J$ = 6.0 Hz) | 111.4 | 111.2 |
| 10 | 1.64 (d, $J$ = 6.5 Hz) | 1.62 (d, $J$ = 7.0 Hz) | 12.5 | 12.3 |
| 11 | 1.88 (br s) | not reported | | |
| 12 | | | 165.5 | 165.5 |
| 13 | | | 142.4 | 142.6 |
| 14 | | | 54.5 | 54.4 |
| 15 | | | 122.8 | 123.0 |
| 16 | | | 143.3 | 143.3 |
| 17 | | | 134.4 | 134.1 |

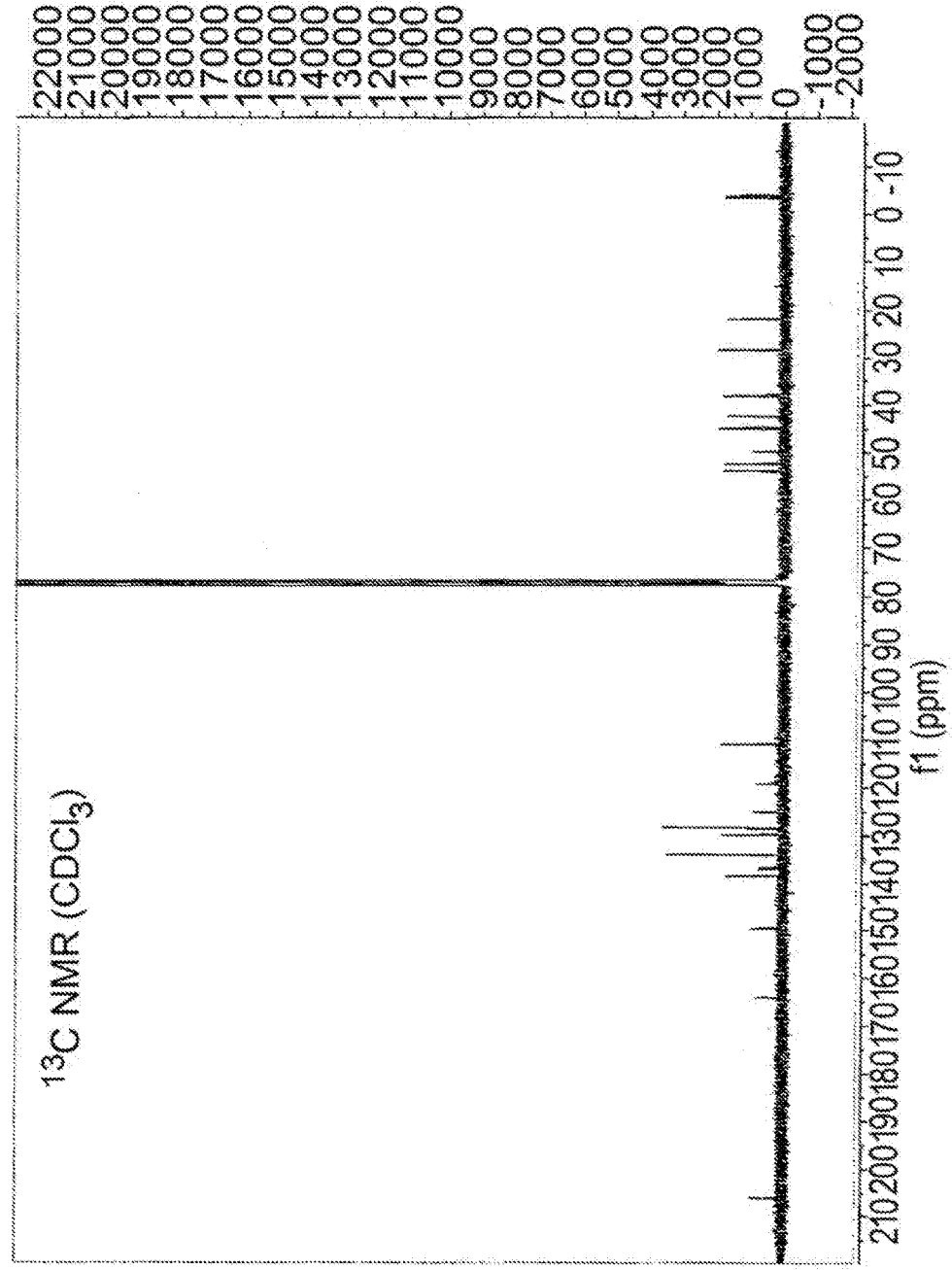

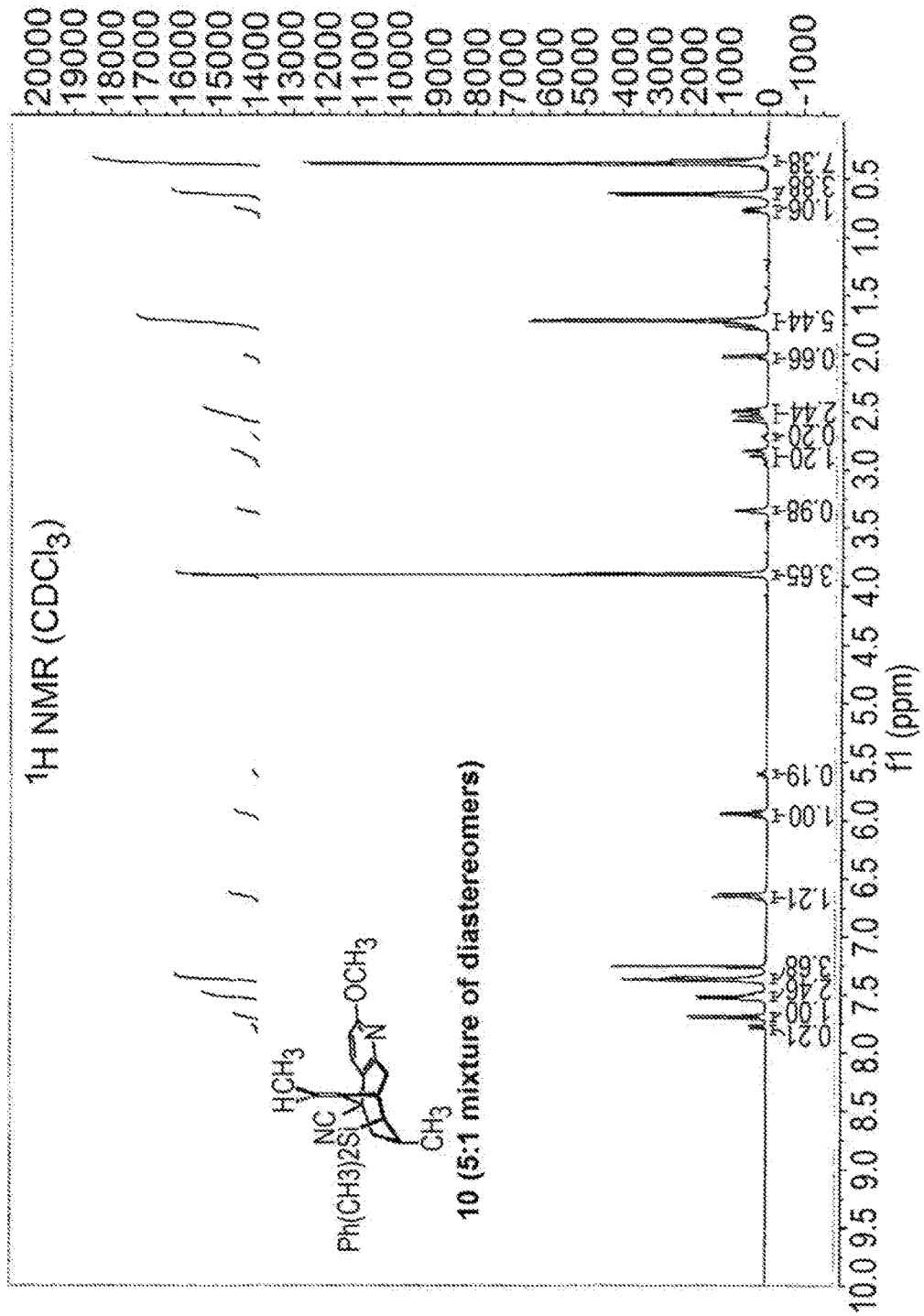

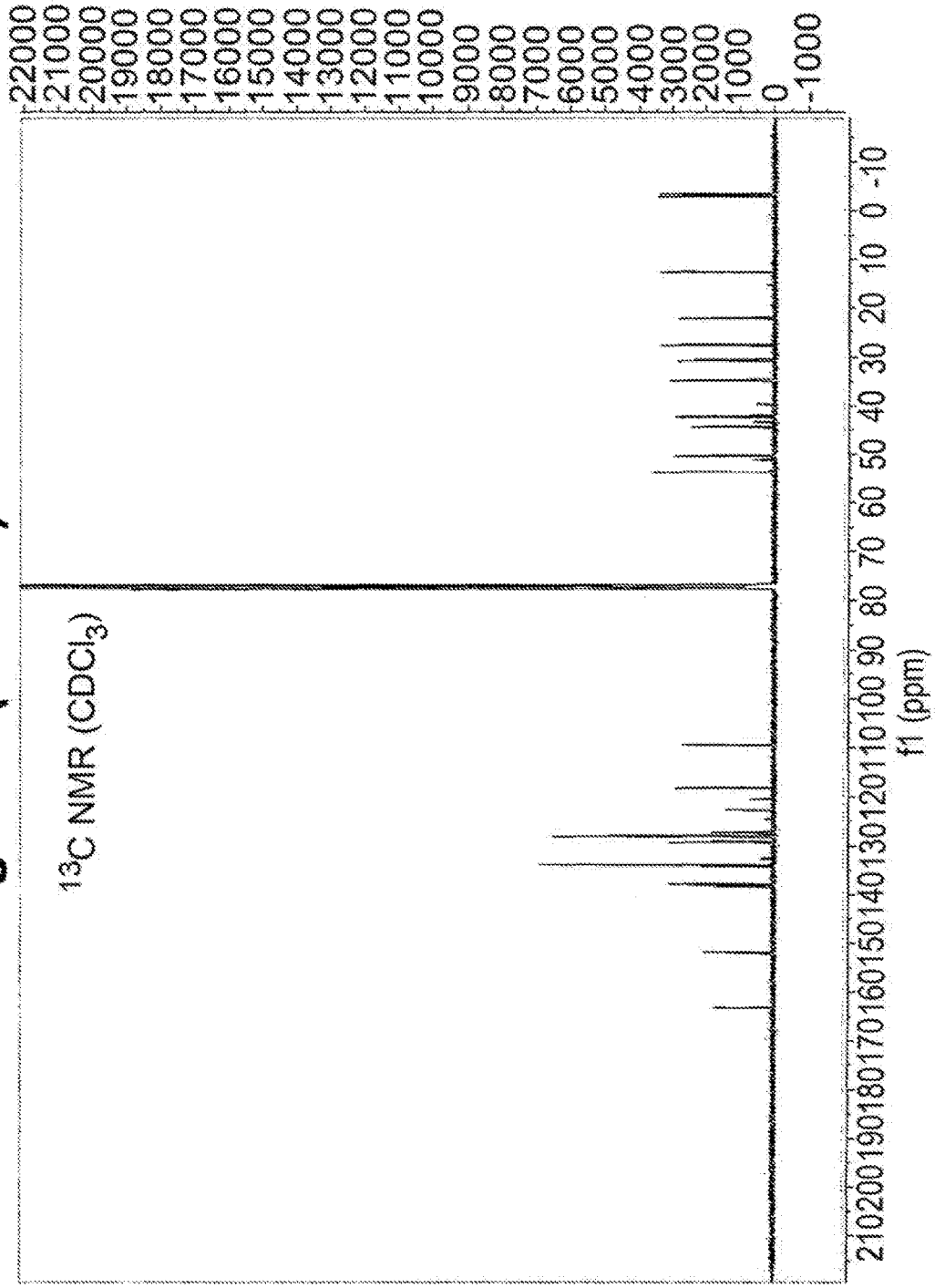

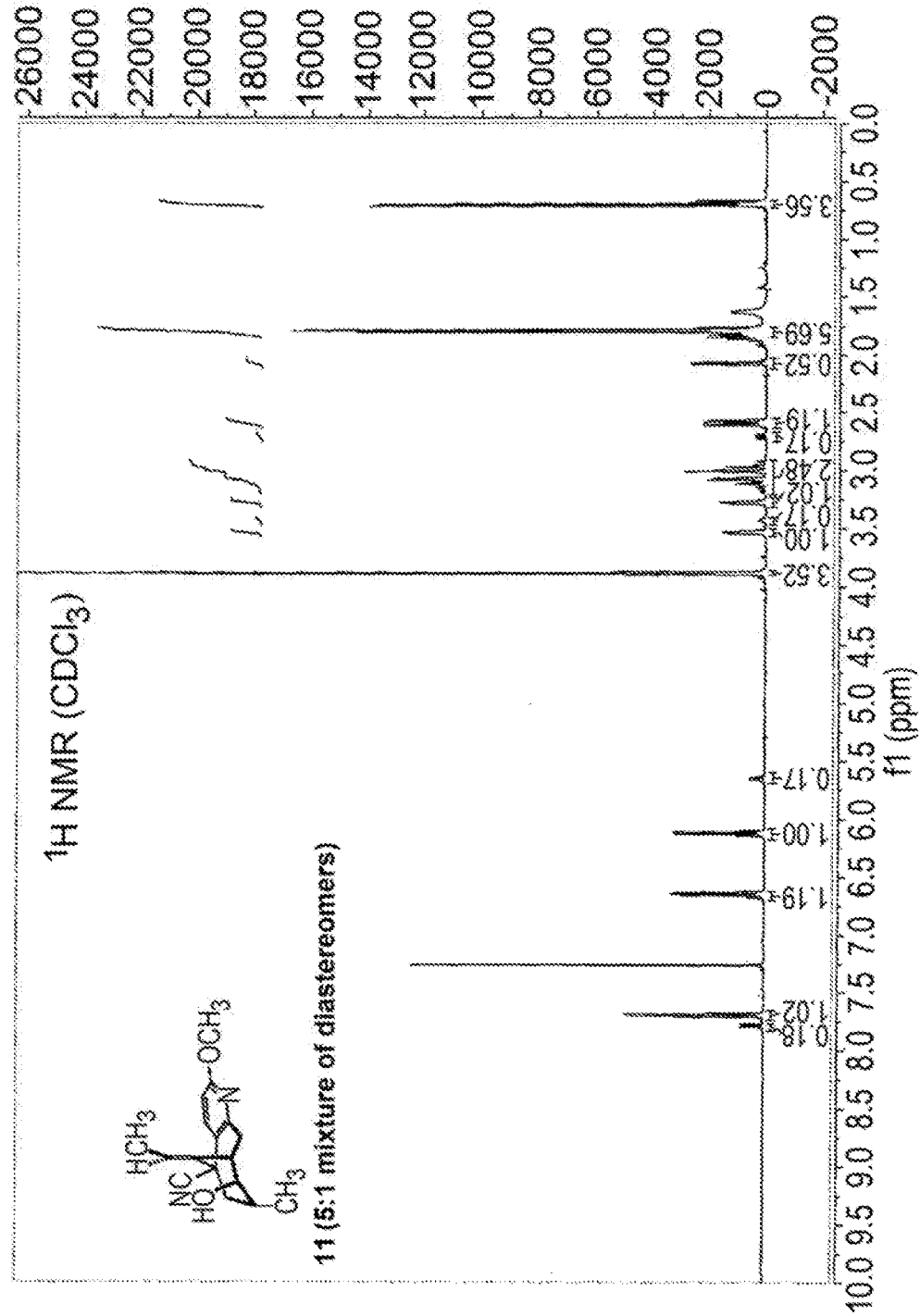

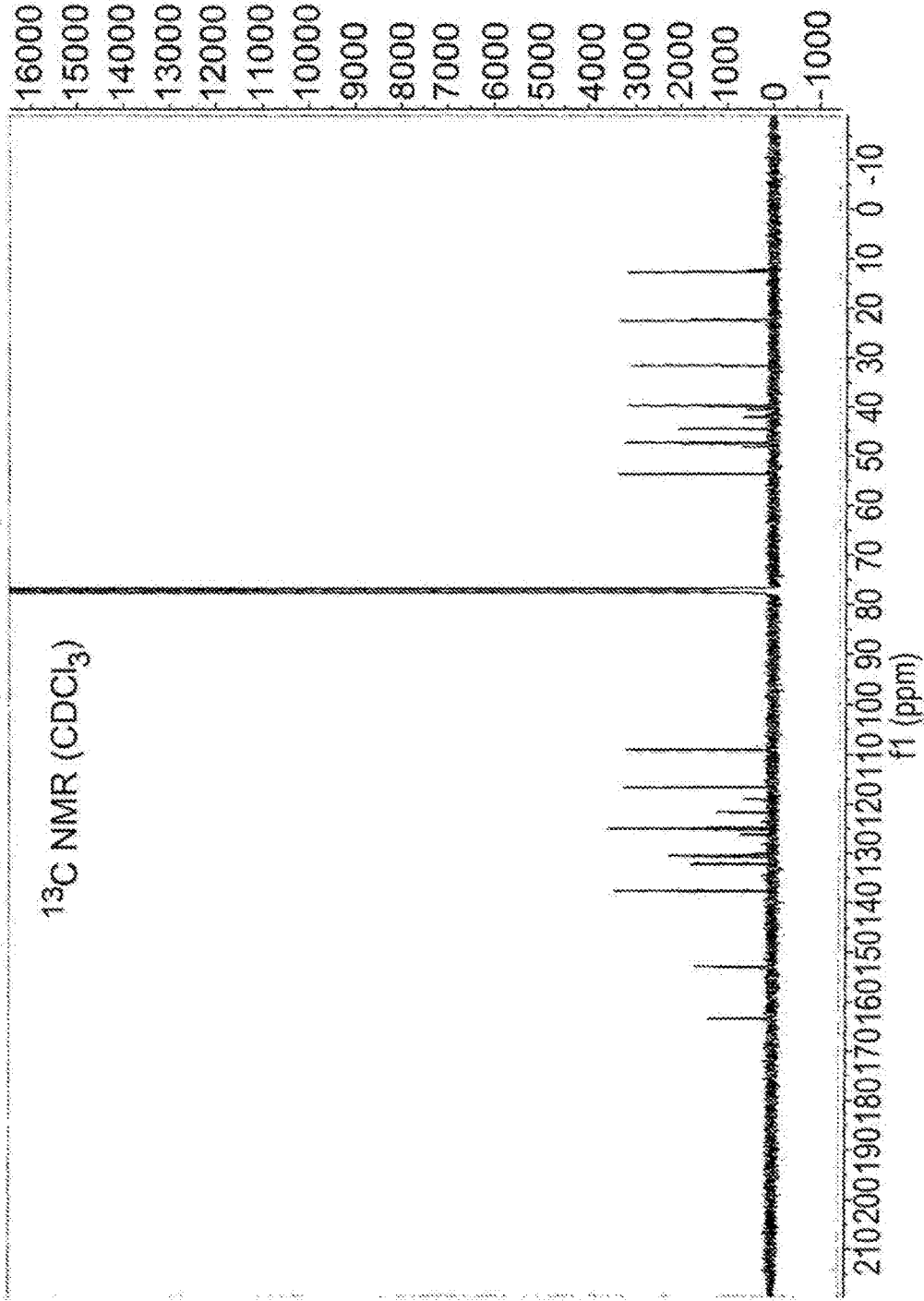

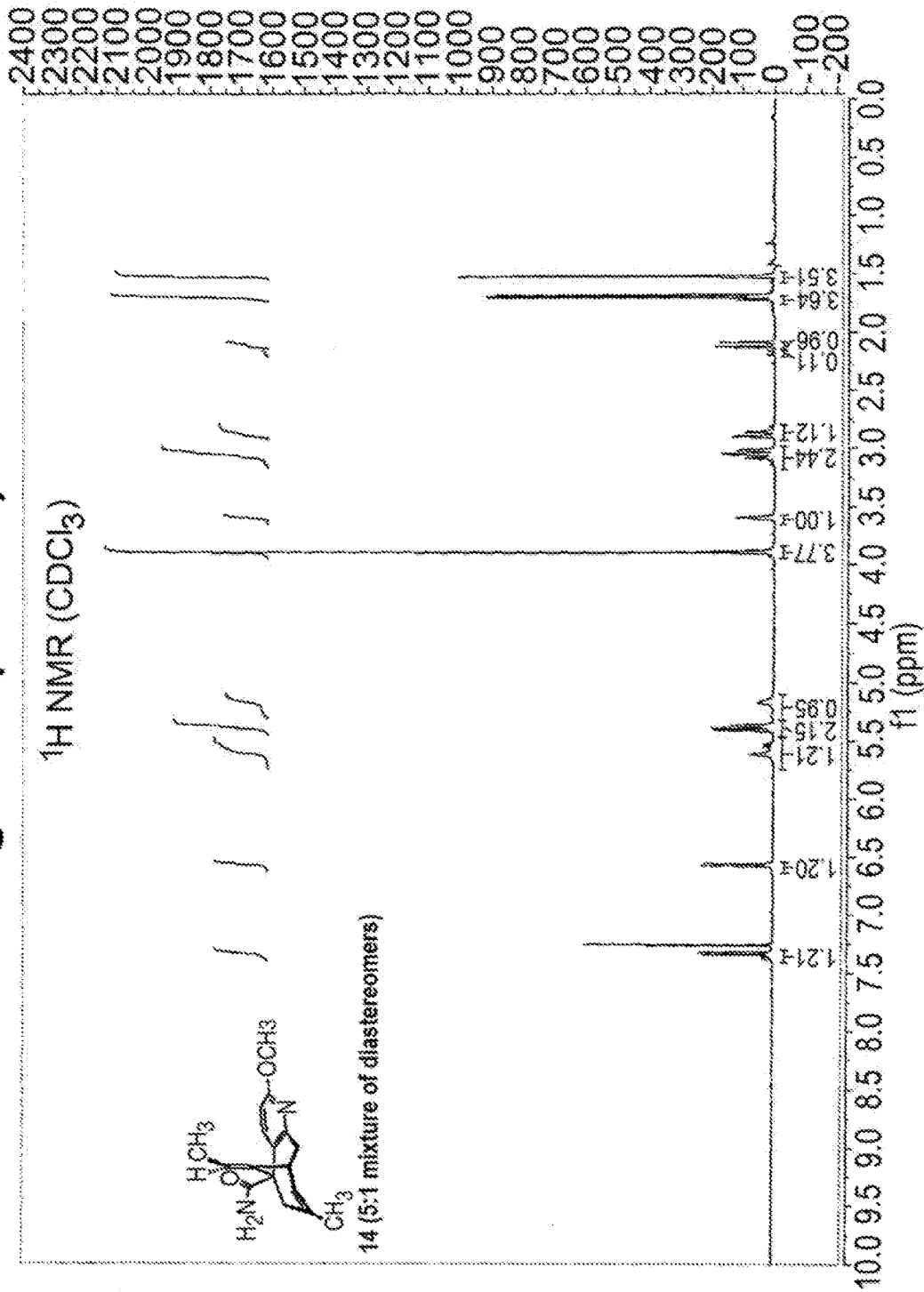

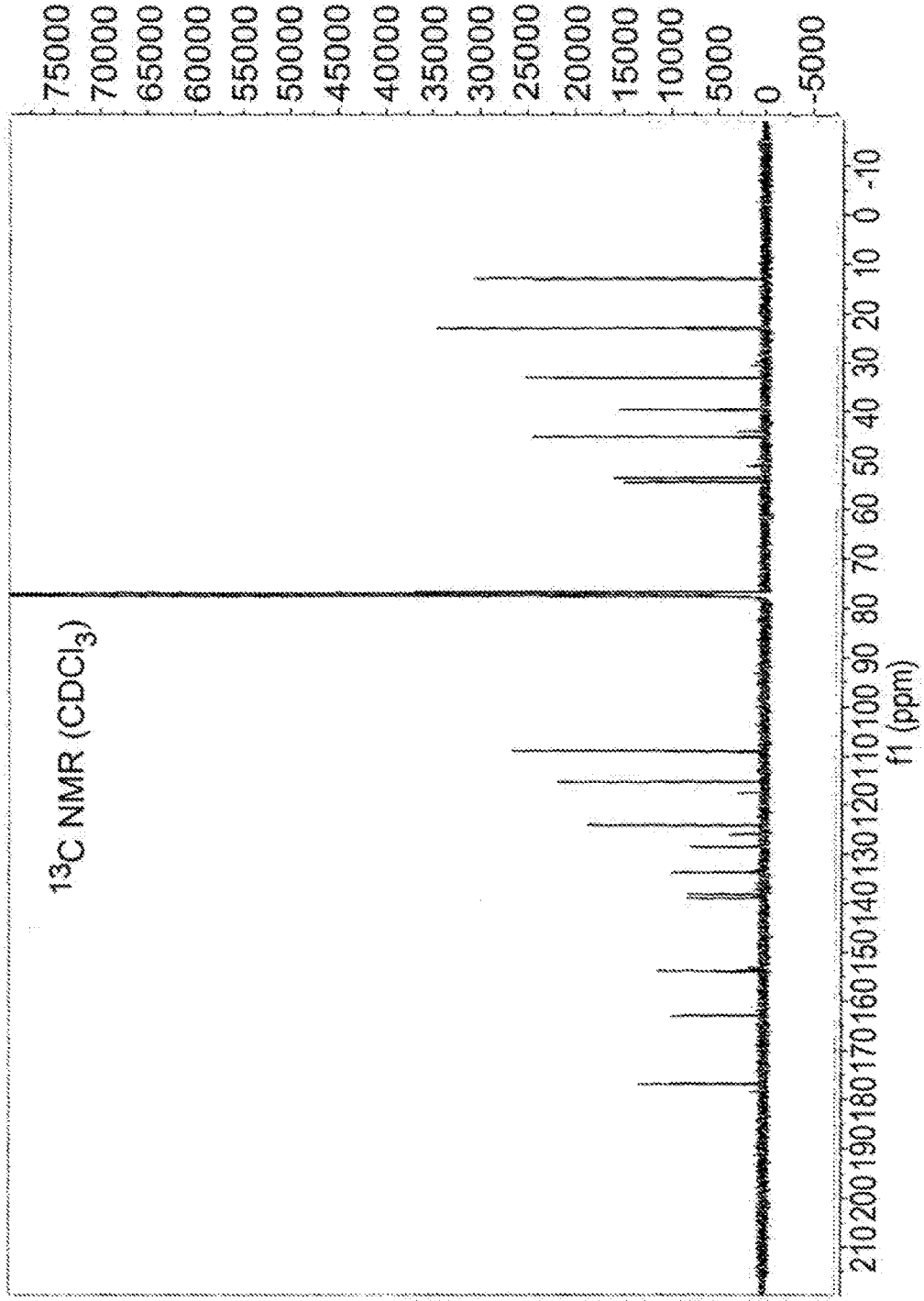

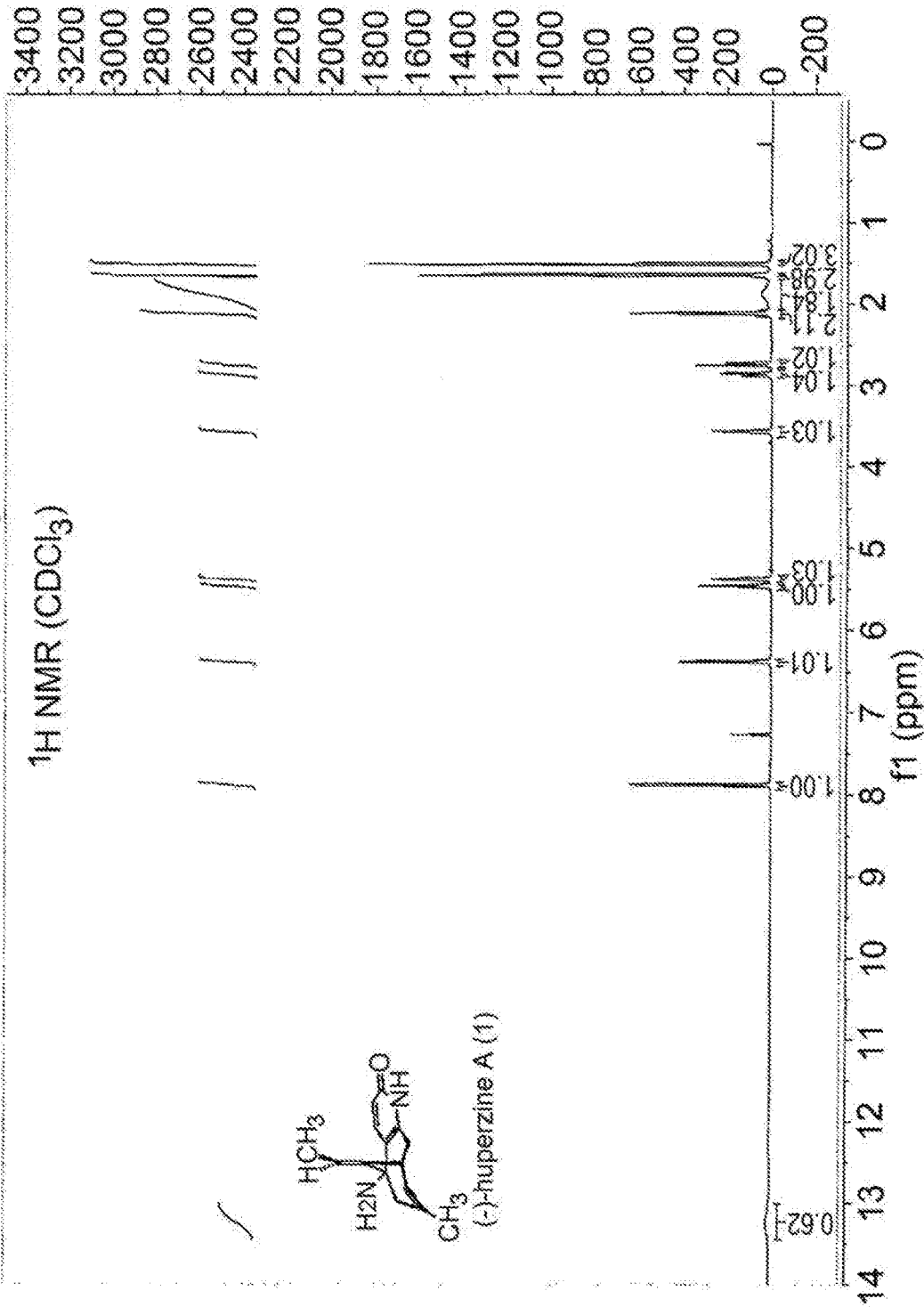

(−)-HUPERZINE A PROCESSES AND RELATED COMPOSITIONS AND METHODS OF TREATMENT

RELATED APPLICATIONS/RESEARCH SUPPORT

This application is a divisional application of United States national phase patent application Ser. No. 14/003,213 filed on Mar. 25, 2014, now U.S. Pat. No. 10,059,672, which is a United States national phase patent application based upon international patent application number PCT/US2012/025628, entitled "(--)-Huperzine A Processes and Related Compositions and Methods of Treatment", filed on Feb. 17, 2012, which claims the benefit of priority of U.S. provisional patent application Ser. No. 61/449,198, entitled "Huperzine A", filed Mar. 4, 2011, the entire contents of which are incorporated by reference herein.

BACKGROUND OF THE INVENTION (−)-Huperzine A (1) is a tricyclic alkaloid produced by the Chinese herb *Huperzia serrata*.[1] (−)-Huperzine A (1) is a potent, selective, and reversible inhibitor of acetylcholine esterase (AChE, Ki=23 nM).[2] Recent studies have established that this activity may be exploited to counteract organophosphate chemical warfare agents, such as sarin and VX, by inhibiting their covalent modification of peripheral and cerebral AChE.[3] A large body of evidence also suggests that (−)-huperzine A (1) may slow the progression of neurodegenerative diseases, including Alzheimer's disease.[4] (−)-Huperzine A (1) is well tolerated in humans, even at doses well above those required clinically.[5] Consequently, clinical investigation of (−)-huperzine A (1) is a subject of intense research in the pharmaceutical and defense industries.

The primary obstacle to the clinical development of (−)-huperzine A (1) has been one of supply. Extraction from natural sources is low-yielding (average yield=0.011% from the dried herb),[4a] and overharvesting has caused a rapid decline in the abundance of Huperziaceae.[6] Compounding these issues, the producing species requires nearly 20 years to reach maturity.[6]

Total synthesis offers an alternative potential source of huperzine. An enantioselective synthesis is highly desirable, because (+)-huperzine A is significantly less potent than the natural (−)-antipode (1).[7] The first total syntheses of (±)-huperzine A were reported by Kozikowski and Xia[8] and Qian and Ji.[9] A chiral auxiliary-based route was later developed by Kozikowski et al.[10] In the interceding years, several research groups have reported modifications to the Kozikowski route,[11] as well as complete,[12] partial,[13] and formal[14] routes to huperzine. Nonetheless, Kozikowski's chiral controller-based route,[10] which proceeds in 16 steps and ca. 2.8% yield, remains the most efficient published pathway to synthetic (−)-huperzine A (1).[15]

Given the large number of steps and relatively poor stereochemical yield of known processes for making (−)-huperzine A, and the increasing importance of (−)-huperzine A as a neuroprotective agent, the need exists for improved methods of making substantially pure (−)-huperzine A in yields that facilitate scale-up to commercial manufacturing.

SUMMARY OF THE INVENTION

In one embodiment, the invention provides novel processes for making substantially pure (−) huperzine A and substantially pure (−) huperzine A derivatives in relatively large yields through syntheses that employ significantly fewer steps than known techniques.

In another embodiment, the invention provides novel processes for making various intermediates useful in the manufacture of pharmaceutically-active ingredients, including substantially pure (−) huperzine A and substantially pure (−) huperzine A derivatives.

In still another embodiment, the invention provides various novel compositions useful in the manufacture of pharmaceutically-active ingredients, including substantially pure (−) huperzine A and substantially pure (−) huperzine A derivatives.

In still another embodiment, the invention provides methods of treating or preventing a neurological disorder comprising administering either substantially pure (−) huperzine A or a substantially pure (−) huperzine A derivative to a subject who suffers from, or who is at risk of developing, a neurological disorder.

In still another embodiment, the invention provides a novel process for making substantially pure (−) huperzine A having the formula:

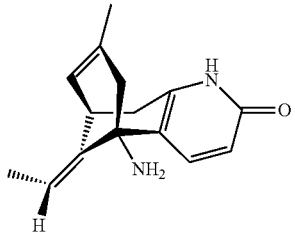

comprising subjecting an amide of the formula:

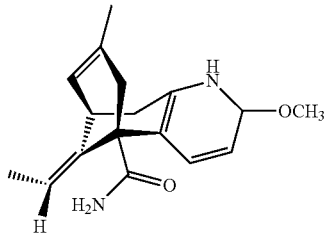

to a modified Hoffmann reaction in an aqueous or alcohol solvent (preferably methanol) and in the presence of bis(trifluoroacetoxyiodo)benzene (PIFA) to form an intermediate, globally deprotecting the intermediate to form (−) huperzine A, and purifying the (−) huperzine A (e.g. by crystallization and/or flash column chromatography) to yield substantially pure (−) huperzine A.

"Substantially pure (−) huperzine A" as used herein comprises greater than about 80% by weight of (−) huperzine A and less than about 20% by weight of (+) huperzine A, more preferably greater than about 90% by weight of (−) huperzine A and less than about 10% by weight of (+) huperzine A, even more preferably greater than about 95% by weight of (−) huperzine A and less than about 5% by weight of (+) huperzine A, and most preferably greater than about 99% by weight of (−) huperzine A and less than about 1% by weight of (+) huperzine A. A virtually pure (−) huperzine A derivative contains more than 99.5% (−) by weight huperzine A and less than 0.5% by weight (+) huperzine A, more preferably more than about 99.9% (−) huperzine A and less than about 0.1% (+) huperzine A. A "substantially pure (+) huperzine A derivative" is defined similarly with respect to the relative amounts of its (+) and (−) enantiomers.

As used herein, the term (+) huperzine A (or "racemic huperzine A" or "huperzine A racemate") means a composition comprising about 40-60% of (−) huperzine A and about 40-60% of (+) huperzine A. A racemate of a huperzine A derivative is defined similarly with respect to the relative amounts of its (−) and (+) enantiomers.

"Huperzine A derivatives" (e.g. as used in the term "substantially pure (−) huperzine A derivative") refers to compounds as described in U.S. Pat. No. RE38460, as well as the compounds of formulae (II) and (III) described hereinafter.

In one embodiment, the amide which is subjected to modified Hoffmann reaction as described above is made, preferably one pot, by a process comprising dehydrating a cyanoalcohol of the formula:

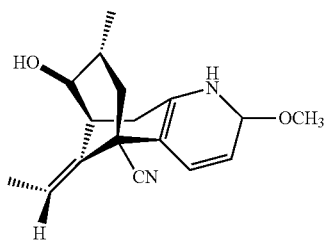

in an organic solvent (preferably toluene), under heated conditions, and in the presence of a Burgess reagent to form a dehydration product, and subjecting the dehydration product to thermolysis in an alcohol (preferably, aqueous ethanol) and in the presence of a platinum catalyst to form the amide. This novel reaction also constitutes an embodiment of the invention and can also be done in steps.

In one embodiment, the cyanoalcohol described above is made, preferably one pot, by subjecting an olefination product which is in substantially E isomer form and which has the formula:

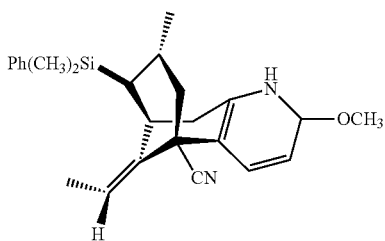

to oxidative desilylation (e.g. by reaction with boron trifluoride-acetic acid complex, or a Bronsted acid such as TFA, MSA, FMSA, or tetrafluoroboric acid in an inert solvent, e.g., DCM, or through use of Fleming-Tamao oxidation followed by fluoride, hydrogen peroxide and potassium carbonate). In addition to protic acid, removal of the silyl group involves the steps of treatment with fluoride, hydrogen peroxide and potassium carbonate. This novel reaction step also constitutes an embodiment of the invention.

In one embodiment, the olefination product described above is made, preferably one pot, in a process comprising deprotonating an addition alkylation product of the formula:

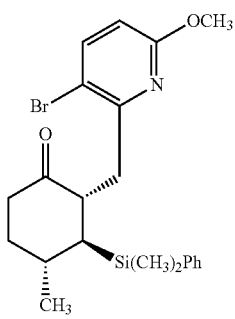

by reacting the addition alkylation product with lithium bis(trimethylsilyl) amide (LHMDS) or lithium diisopropyl amide (LDA) and an electrophilic source of cyanide (e.g., para-toluenesulfonyl cyanide, cyanogen bromide, etc.) in an organic solvent (e.g. THF or toluene) to form an α-cyanoketone, subjecting the α-cyanoketone to palladium-catalyzed (e.g., tetrakis(triphenylphosphine)palladium, tris(dibenzylidene acetone) dipalladium, palladium bis(tri-tert-butylphoshpine) intramolecular enolate heteroarylation in the presence of a base (most preferably sodium tert-butoxide) and a palladium catalyst to form a cyclized product, and stereoselectively olefinating a ketone function of the cyclized product in a Wittig olefination reaction in the presence of a base (e.g. n-butyllithium, sodium bis(trimethylsilyl) amide, lithium bis(trimethylsilyl)amide, potassium bis(trimethylsilyl)amide or lithium diisopropylamide) and in an organic solvent (e.g. THF, diethylether or 1,4-dioxane) to form an olefination product, wherein the stereoselective olefination of the cyclized product kinetically favors formation of the olefination product in E-isomer form. This novel reaction step also constitutes an embodiment of the invention and can also be done in steps.

In one embodiment, the addition alkylation product is made, preferably one pot, in a process comprising reacting (R)-4-methyl-cyclohex-2-ene-1-one with lithium dimethylphenylsilylcuprate in a conjugate addition reaction to form an incipient enolate and alkylating the incipient enolate with 3-bromo-2-(bromomethyl)-6-methoxypyridine) to form the addition alkylation product. This novel reaction step also constitutes an embodiment of the invention and can also be done in steps.

In still another embodiment, the invention provides a process for cyclizing a β-ketone comprising subjecting an α-cyanoketone to palladium-catalyzed intramolecular enolate heteroarylation, as described in detail hereinafter.

In still another embodiment, the invention provides a novel process for making substantially pure (−) huperzine A comprising:

(a) preferably in one pot, reacting (R)-4-methyl-cyclohex-2-ene-1-one with lithium dimethylphenylsilylcuprate in a conjugate addition reaction to form an incipient enolate and alkylating the incipient enolate with 3-bromo-2-(bromomethyl)-6-methoxypyridine) to form an addition alkylation product having the formula:

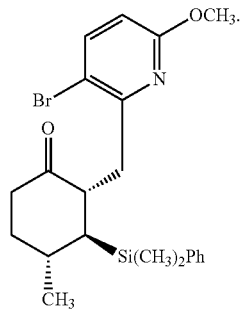

(b) preferably in one pot, deprotonating the addition alkylation product by reacting the addition alkylation product with lithium bis(trimethylsilyl) amide (LHMDS) or lithium diisopropyl amide (LDA) in an organic solvent (e.g. THF or toluene) to form an α-cyanoketone, subjecting the α-cyanoketone to palladium-catalyzed intramolecular enolate heteroarylation in the presence of a base (most preferably sodium tert-butoxide) to form a cyclized product, and stereoselectively olefinating a ketone function of the cyclized product in a Wittig olefination reaction in the presence of a base (e.g. n-butyllithium, sodium bis(trimethylsilyl)amide, lithium bis(trimethylsilyl)amide, potassium bis(trimethylsilyl)amide or lithium diisopropylamide) and in an organic solvent (e.g. THF, diethylether or 1,4-dioxane) to form an olefination product, wherein the stereoselective olefination of the cyclized product kinetically favors formation of the olefination product in E-isomer form and wherein the olefination product has the formula:

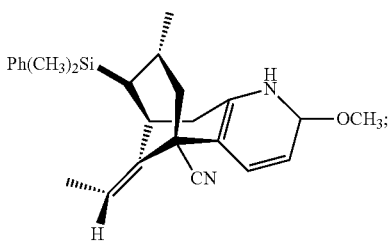

(c) subjecting the olefination product to to oxidative disilylation (e.g. by reaction with boron trifluoride-acetic acid complex, or a Bronsted acid such as TFA, MSA, FMSA, or tetrafluoroboric acid in an inert solvent, e.g., DCM, or through use of Fleming-Tamao oxidation) to form a cyanoalcohol having the formula:

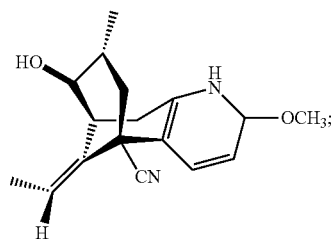

(d) preferably in one pot, dehydrating the cyanoalcohol in an organic solvent (preferably toluene), under heated conditions, and in the presence of a Burgess reagent to form a dehydration product, and subjecting the dehydration product to thermolysis in an alcohol (preferably ethanol) and in the presence of a platinum catalyst to form the amide having the formula:

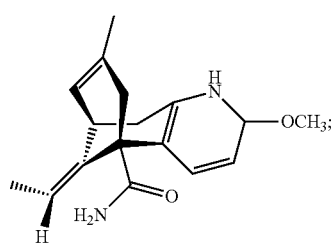

and (f) subjecting the amide to modified Hoffmann reaction in an aqueous or alcohol solvent (preferably methanol) and in the presence of bis(trifluoroacetoxyiodo)benzene (PIFA) to form an intermediate, globally deprotecting the intermediate to form (±) huperzine A, and purifying the (±) huperzine A (e.g. by flash column chromatography) to yield substantially pure (−) huperzine A:

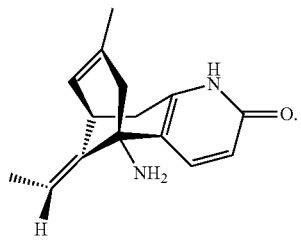

In still another embodiment, the invention provides a compound of the formula (I):

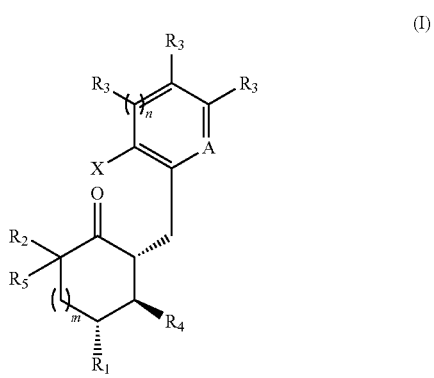

wherein:

$R_1$ is selected from the group consisting of substituted or unsubstituted $C_1$-$C_6$ alkyl and substituted or unsubstituted ether;

$R_2$ and $R_5$ are independently selected from the group consisting of H, substituted or unsubstituted $C_1$-$C_6$ alkyl, and CN, provided that when one of $R_2$ or $R_5$ is CN, the other must be H;

X is halogen;

$R_3$ at each occurrence is independently selected from the group consisting of H, substituted or unsubstituted $C_1$-$C_6$ alkyl, ether, amino, and alkoxy;

$R_4$ is selected from the group consisting of $Si(CH_3)_2Ph$, substituted or unsubstituted $C_1$-$C_6$ alkyl, substituted or unsubstituted $C_1$-$C_6$ alkenyl, substituted or unsubstituted aryl, and substituted or unsubstituted heteroaryl;

A is C, N, or S;

m is 0, 1, or 2;

n is 0 or 1;

or a pharmaceutically acceptable salt, enantiomer, diastereomer solvate or polymorph thereof.

In still another embodiment, the invention provides a compound of the formula (II):

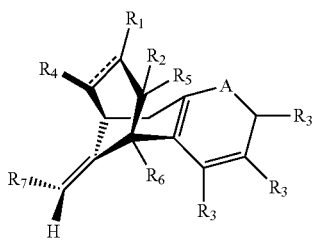

wherein:

$R_1$ is selected from the group consisting of substituted or unsubstituted $C_1$-$C_6$ alkyl and substituted or unsubstituted ether;

$R_2$ and $R_5$ are independently selected from the group consisting of H and substituted or unsubstituted $C_1$-$C_6$ alkyl;

$R_3$ at each occurrence is independently selected from the group consisting of H, substituted or unsubstituted $C_1$-$C_6$ alkyl, ether, amino, and alkoxy;

$R_4$ is selected from the group consisting of H, OH, and $Si(CH_3)_2Ph$;

$R_6$ is selected from the group consisting of $NH_2$, amide, CN, a carboxylic acid derivative (e.g. an ester, a ketone, or a secondary or tertiary amide), an alcohol, or an aldehyde;

$R_7$ is substituted or unsubstituted $C_1$-$C_6$ alkyl, ester, or substituted or unsubstituted aryl;

A is C, N, or S; and n is 0 or 1;

or a pharmaceutically acceptable salt, enantiomer, diastereomer solvate or polymorph thereof.

In one embodiment, compounds of formulae (I) and (II) are used to make pharmacologically active compositions, including substantially pure (−) huperizine A and substantially-pure (−) huperizine A derivatives.

Preferred compounds of the invention include:

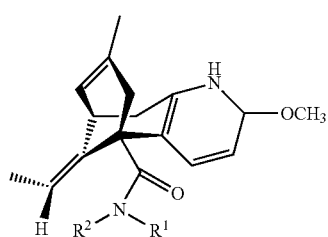

Where $R^1$ and $R^2$ are each independently H or a $C_1$-$C_6$ alkyl group;

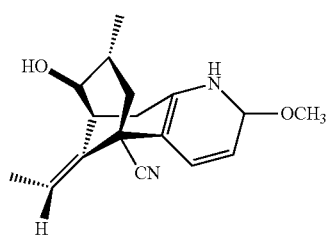

and its primary amine derivatives (where CN is converted to a $CH_2NR^1R^2$ group where $R^1$ and $R^2$ are the same as described above);

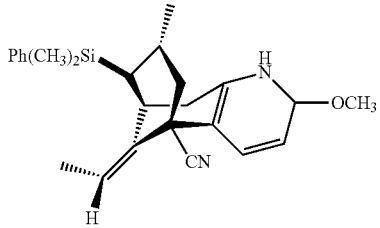

and its primary amine derivatives (where CN is converted to a $CH_2NR^1R^2$ group where $R^1$ and $R^2$ are the same as described above); and

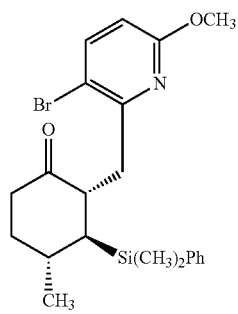

or a pharmaceutically acceptable salt, enantiomer, diastereomer solvate or polymorph thereof.

In still another embodiment, the invention provides a novel process for making substantially pure (−) huperzine A or a derivative thereof having the formula (III):

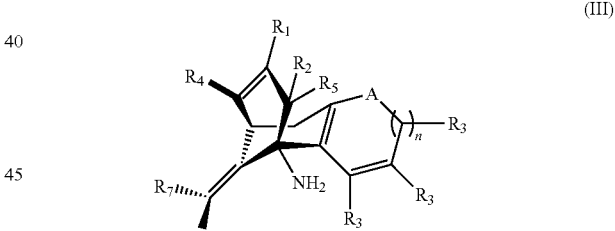

(III)

wherein:

$R_1$ is selected from the group consisting of substituted or unsubstituted $C_1$-$C_6$ alkyl and substituted or unsubstituted ether;

$R_2$ and $R_5$ are independently selected from the group consisting of H and substituted or unsubstituted $C_1$-$C_6$ alkyl;

$R_3$ at each occurrence is independently selected from the group consisting of H, substituted or unsubstituted $C_1$-$C_6$ alkyl, ether, amino, and alkoxy;

$R_4$ is selected from the group consisting of H, OH, and $Si(CH_3)_2Ph$;

$R_7$ is substituted or unsubstituted $C_1$-$C_6$ alkyl, ester, or substituted or unsubstituted aryl;

A is C, N, or S; and n is 0 or 1;

comprising subjecting an amide having the formula (IV):

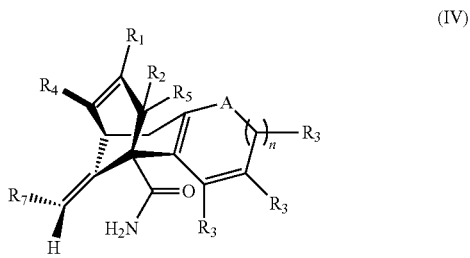

(IV)

wherein $R_1$, $R_2$, $R_3$, $R_4$, $R_5$, $R_7$, A, and n are as defined for the compound of formula (III), to a modified Hoffmann reaction in an aqueous or alcohol solvent (preferably methanol) and in the presence of bis(trifluoroacetoxyiodo)benzene (PIFA) to form an intermediate, globally deprotecting the intermediate to form (±) huperzine A or a (±)huperzine A derivative, and purifying the (±) huperzine A or (±)huperzine A derivative (e.g. by flash column chromatography) to yield substantially pure (−) huperzine A or a substantially pure (±)huperzine A derivative.

In still another embodiment, the invention provides a process for making an amide having the formula (IV):

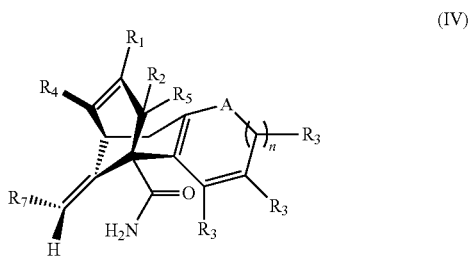

(IV)

wherein:
$R_1$ is selected from the group consisting of substituted or unsubstituted $C_1$-$C_6$ alkyl and substituted or unsubstituted ether;
$R_2$ and $R_5$ are independently selected from the group consisting of H and substituted or unsubstituted $C_1$-$C_6$ alkyl;
$R_3$ at each occurrence is independently selected from the group consisting of H, substituted or unsubstituted $C_1$-$C_6$ alkyl, ether, amino, and alkoxy;
$R_4$ is selected from the group consisting of H, OH, and $Si(CH_3)_2Ph$, and H;
$R_7$ is substituted or unsubstituted $C_1$-$C_6$ alkyl, ester, or substituted or unsubstituted aryl;
A is C, N, or S; and
n is 0 or 1;
comprising dehydrating a cyanoalcohol of the formula (V):

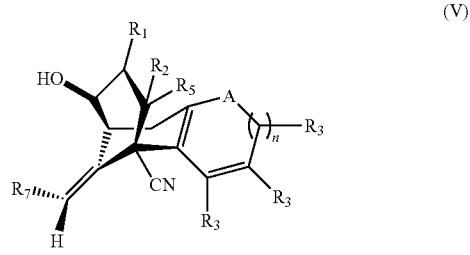

(V)

wherein $R_1$, $R_2$, $R_3$, $R_5$, $R_7$, A, and n are as defined for the compound of formula (IV), in an organic solvent (preferably toluene), under heated conditions, and in the presence of a Burgess reagent to form a dehydration product, and subjecting the dehydration product to thermolysis in an alcohol (preferably ethanol) and in the presence of a platinum catalyst to form the amide, wherein the dehydration and thermolysis can be done one-pot or in steps.

In still another embodiment, the invention provides a process for making a cyanoalcohol of the formula (V):

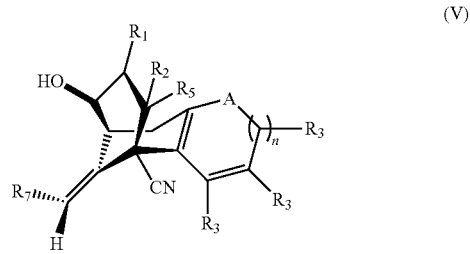

(V)

wherein:
$R_1$ is selected from the group consisting of substituted or unsubstituted $C_1$-$C_6$ alkyl and substituted or unsubstituted ether;
$R_2$ and $R_5$ are independently selected from the group consisting of H and substituted or unsubstituted $C_1$-$C_6$ alkyl;
$R_3$ at each occurrence is independently selected from the group consisting of H, substituted or unsubstituted $C_1$-$C_6$ alkyl, ether, amino, and alkoxy;
$R_7$ is substituted or unsubstituted $C_1$-$C_6$ alkyl, ester, or substituted or unsubstituted aryl;
A is C, N, or S; and
n is 0 or 1;
comprising subjecting an olefination product which is in substantially E isomer form and which has the formula (VI):

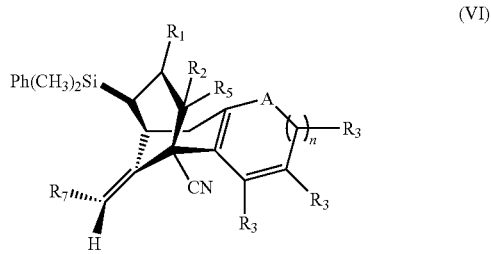

(VI)

wherein $R_1$, $R_2$, $R_3$, $R_5$, $R_7$, A, and n are as defined in the compound of formula (V), to oxidative disilylation (e.g. by reaction with boron trifluoride-acetic acid complex, or a Bronsted acid such as TFA, MSA, FMSA, or tetrafluoroboric acid in an inert solvent, e.g., DCM, or through use of Fleming-Tamao oxidation), wherein the process can be done one-pot or in steps.

In another embodiment, the invention provides a process for making an olefination product which is in substantially E isomer form and which has the formula (VI):

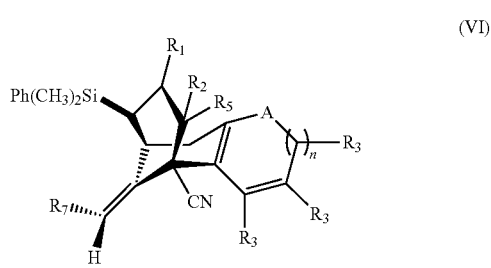

(VI)

wherein:
$R_1$ is selected from the group consisting of substituted or unsubstituted $C_1$-$C_6$ alkyl and substituted or unsubstituted ether;

$R_2$ and $R_5$ are independently selected from the group consisting of H and substituted or unsubstituted $C_1$-$C_6$ alkyl;

$R_3$ at each occurrence is independently selected from the group consisting of H, substituted or unsubstituted $C_1$-$C_6$ alkyl, ether, amino, and alkoxy;

$R_7$ is substituted or unsubstituted $C_1$-$C_6$ alkyl, ester, or substituted or unsubstituted aryl;

A is C, N, or S; and n is 0 or 1;

comprising deprotonating an addition alkylation product having the formula (VII):

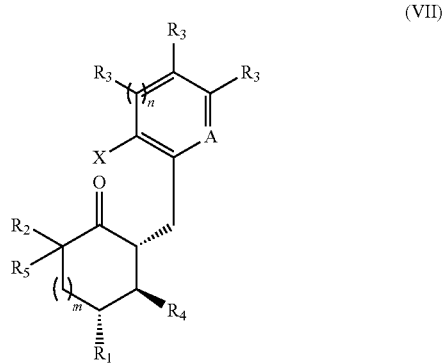

(VII)

wherein $R_1$, $R_2$, $R_3$, $R_5$, A, and n are as defined in (V), $R_4$ is selected from the group consisting of $Si(CH_3)_2Ph$, substituted or unsubstituted $C_1$-$C_6$ alkyl, substituted or unsubstituted $C_1$-$C_6$ alkenyl, substituted or unsubstituted aryl, and substituted or unsubstituted heteroaryl, X is halogen, and m is 0, 1, or 2, by reacting the addition alkylation product with lithium bis(trimethylsilyl) amide (LHMDS) or lithium diisopropyl amide (LDA) in an organic solvent (e.g. THF or toluene) to form an α-cyanoketone, subjecting the α-cyanoketone to palladium-catalyzed intramolecular enolate heteroarylation in the presence of a base (most preferably sodium tert-butoxide) to form a cyclized product, and stereoselectively olefinating a ketone function of the cyclized product in a Wittig olefination reaction in the presence of a base (e.g. n-butyllithium, sodium bis(trimethylsilyl)amide, lithium bis(trimethylsilyl)amide, potassium bis(trimethylsilyl)amide or lithium diisopropylamide) and in an organic solvent (e.g. THF, diethylether or 1,4-dioxane) to form the olefination product, wherein each of the aforementioned reactions can be done one-pot or in steps.

These and other aspects of the invention are described in further detail in the Detailed Description of the Invention.

DETAILED DESCRIPTION OF THE INVENTION

Figure 1:
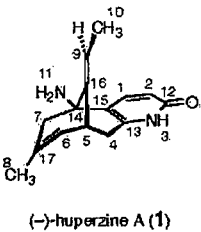
FIG. 1 presents a comparison of NMR data of synthetic and natural (−)-huperzine A.
Figure 2:
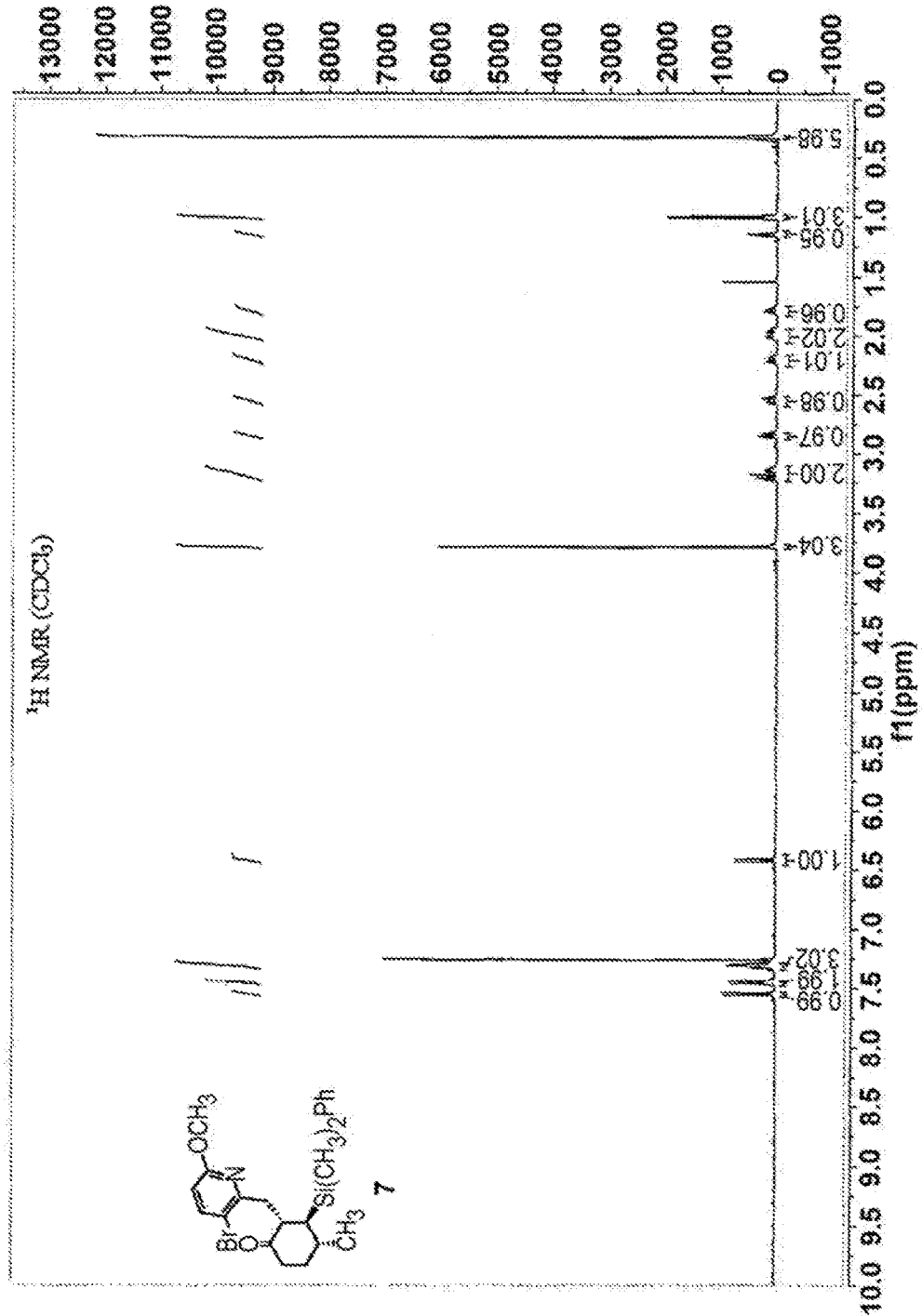
FIG. 2 comprises a catalog of nuclear magnetic resonance and infrared spectra for compositions of the instant invention.
Figure 2:
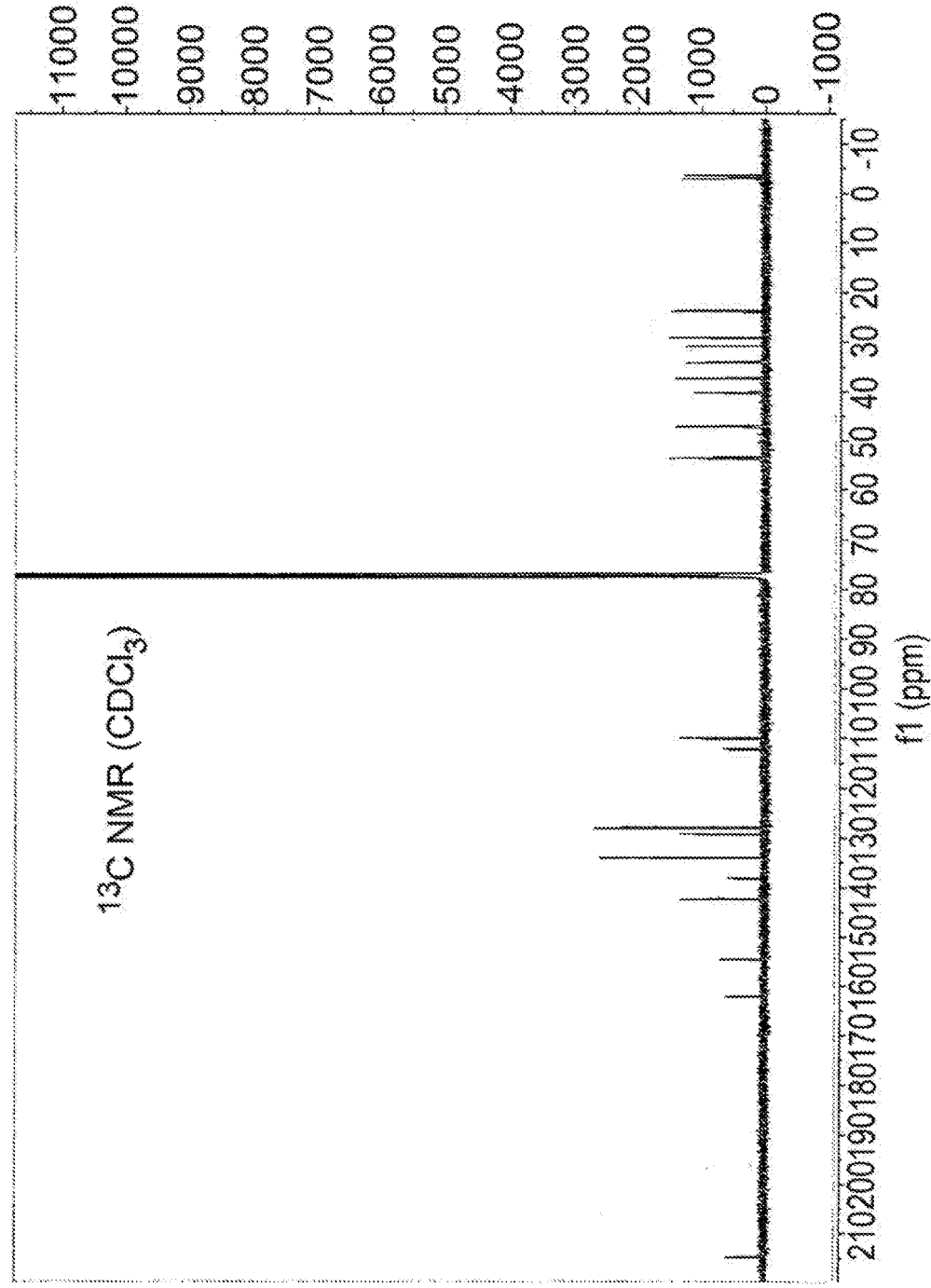
Figure 2:
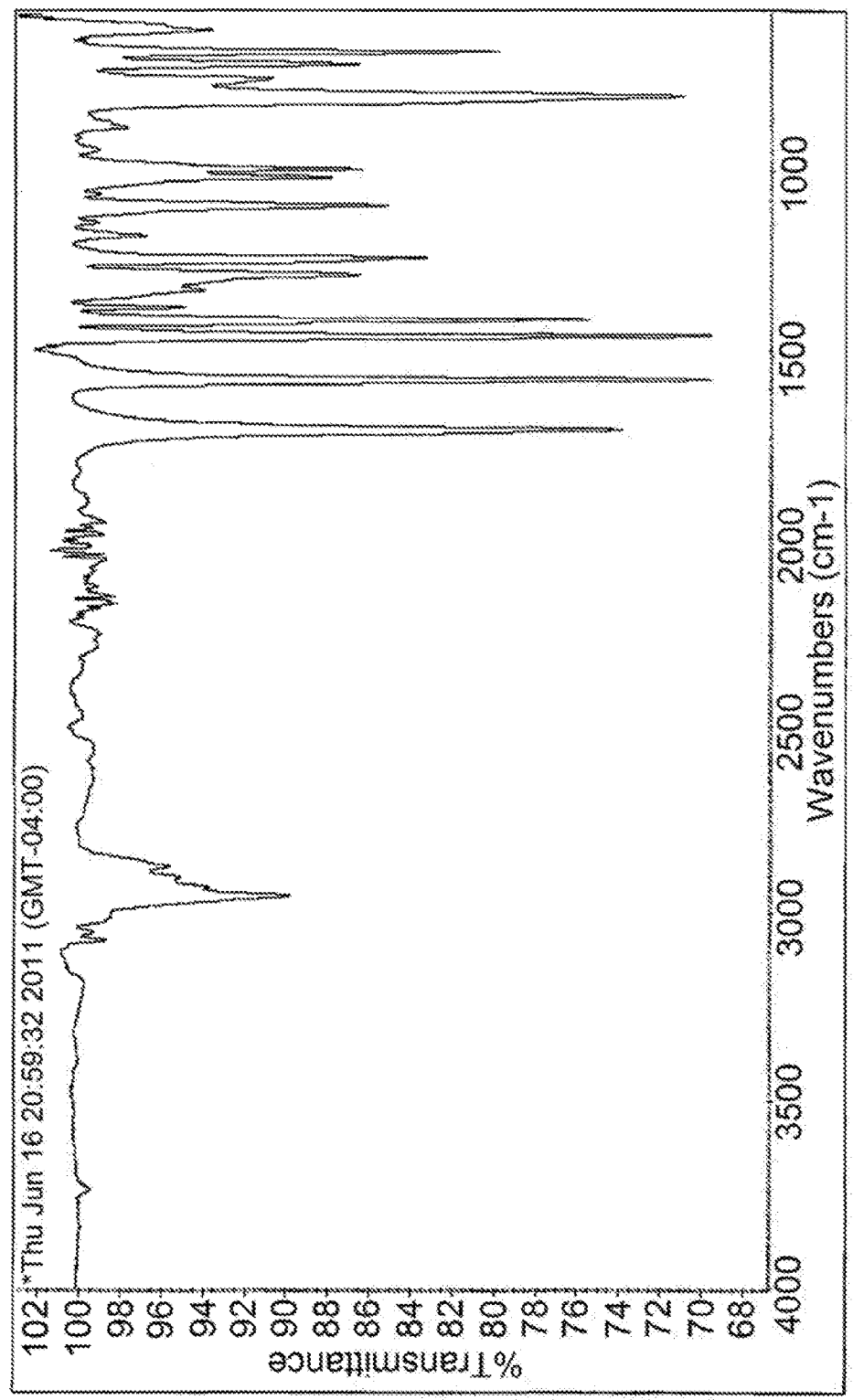
Figure 2:
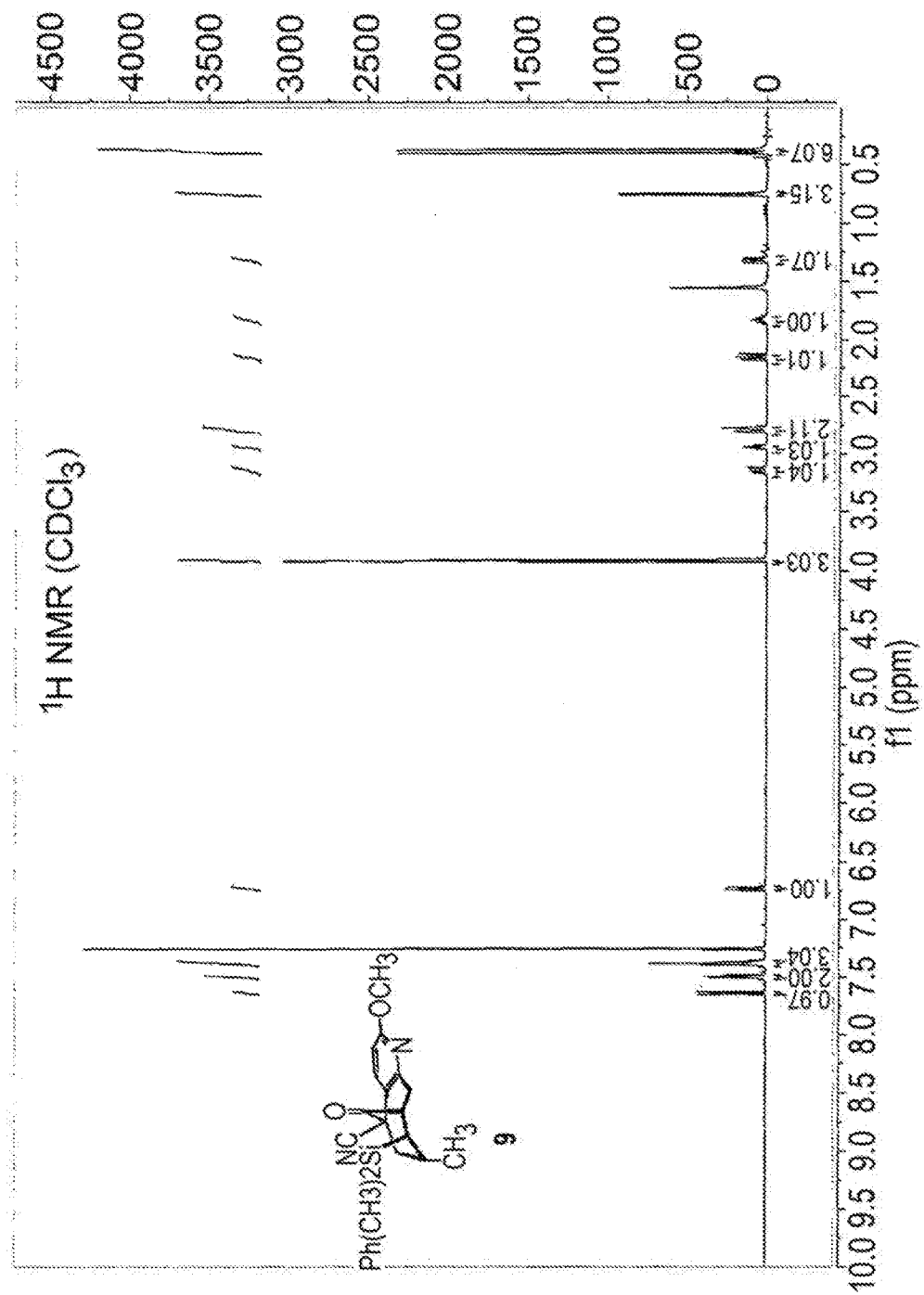
Figure 2:
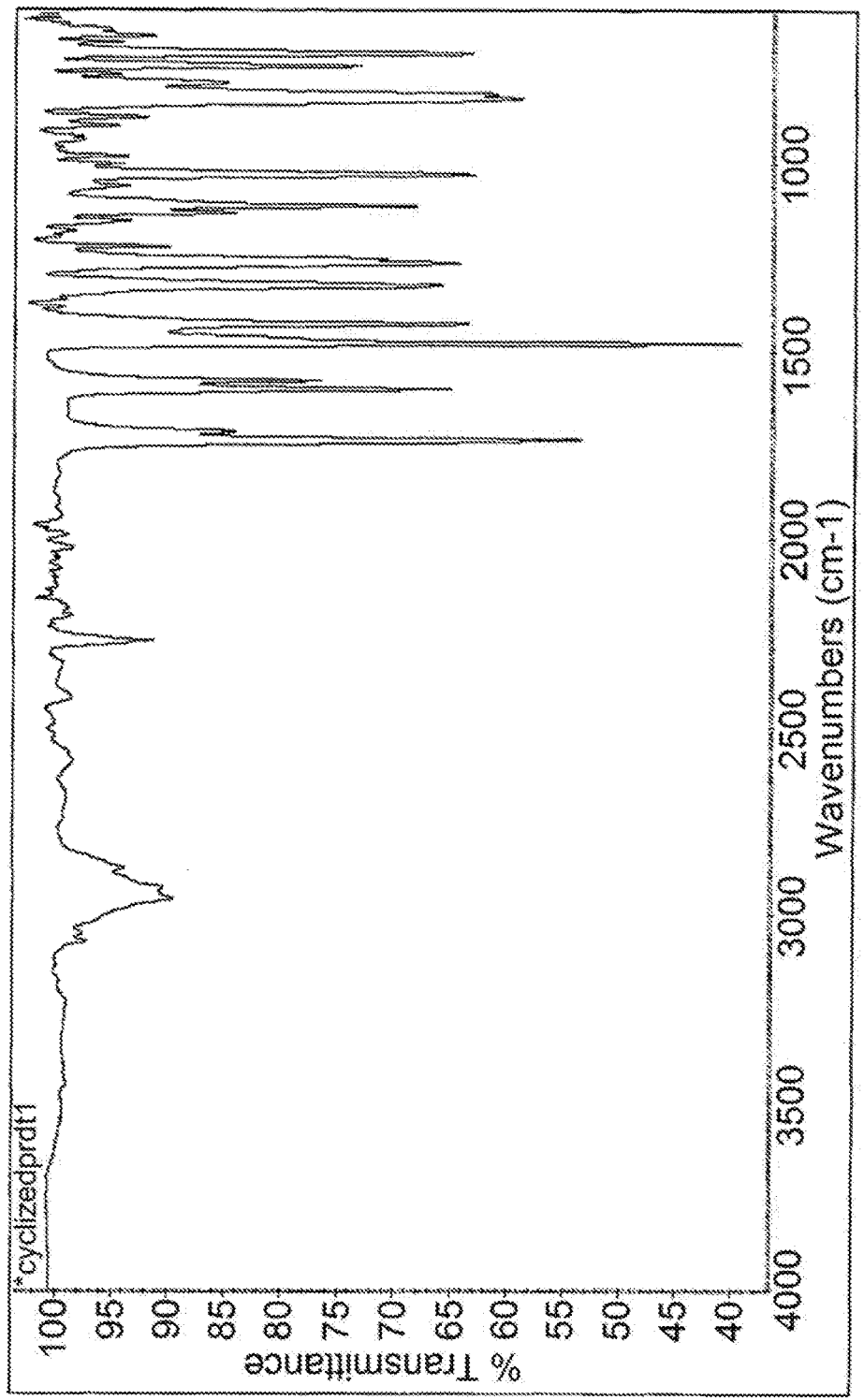
Figure 2:
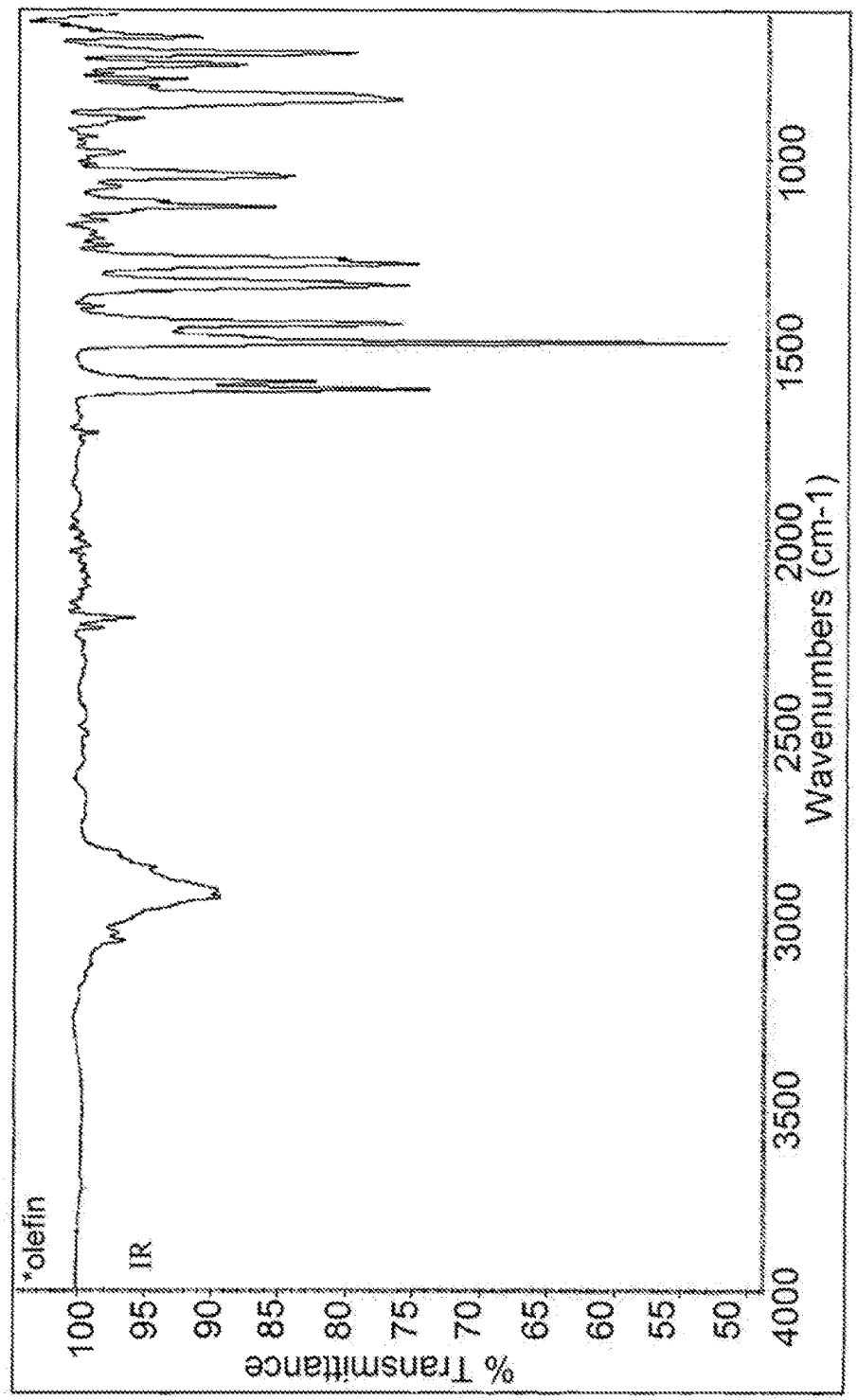
Figure 2:
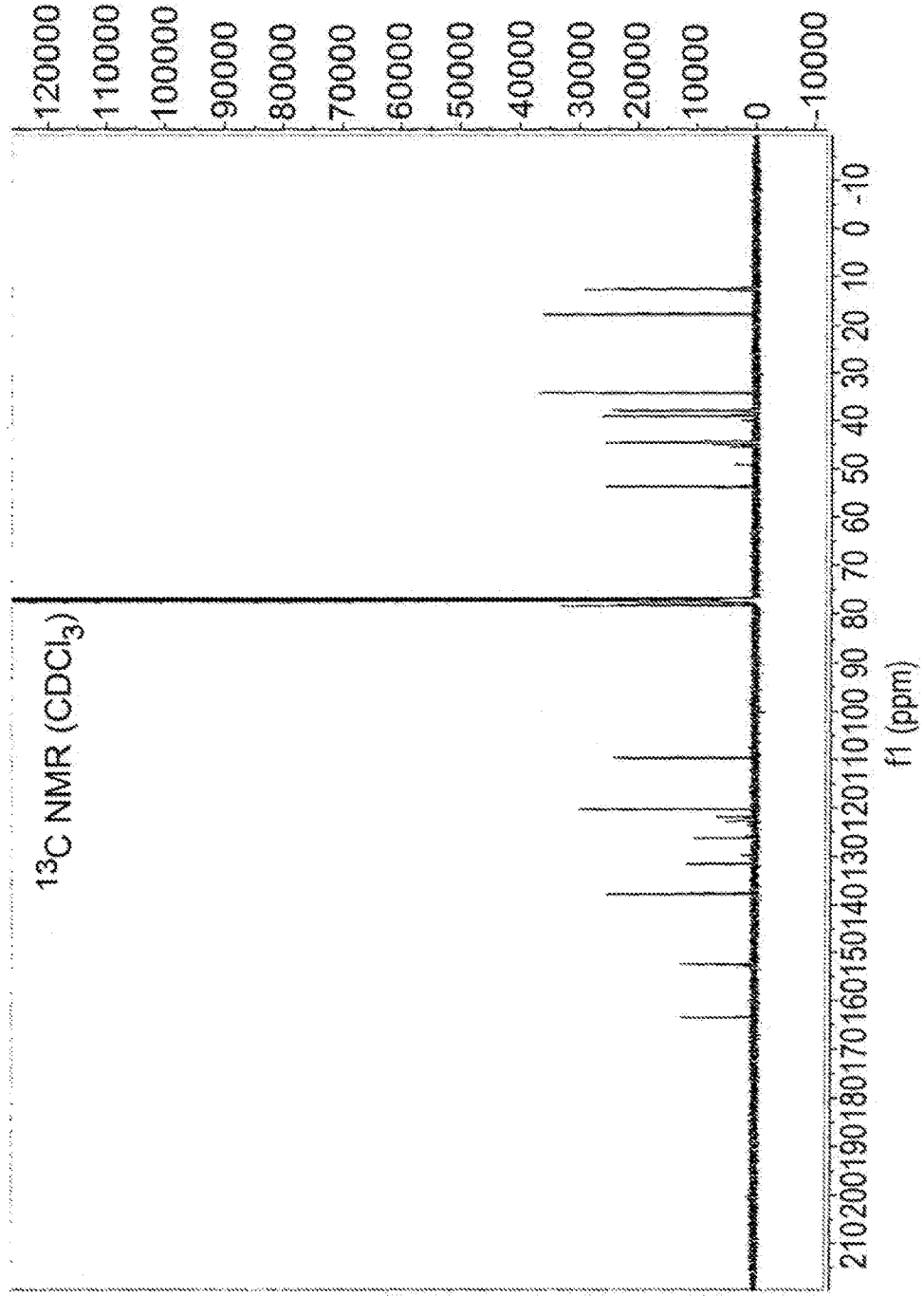
Figure 2:
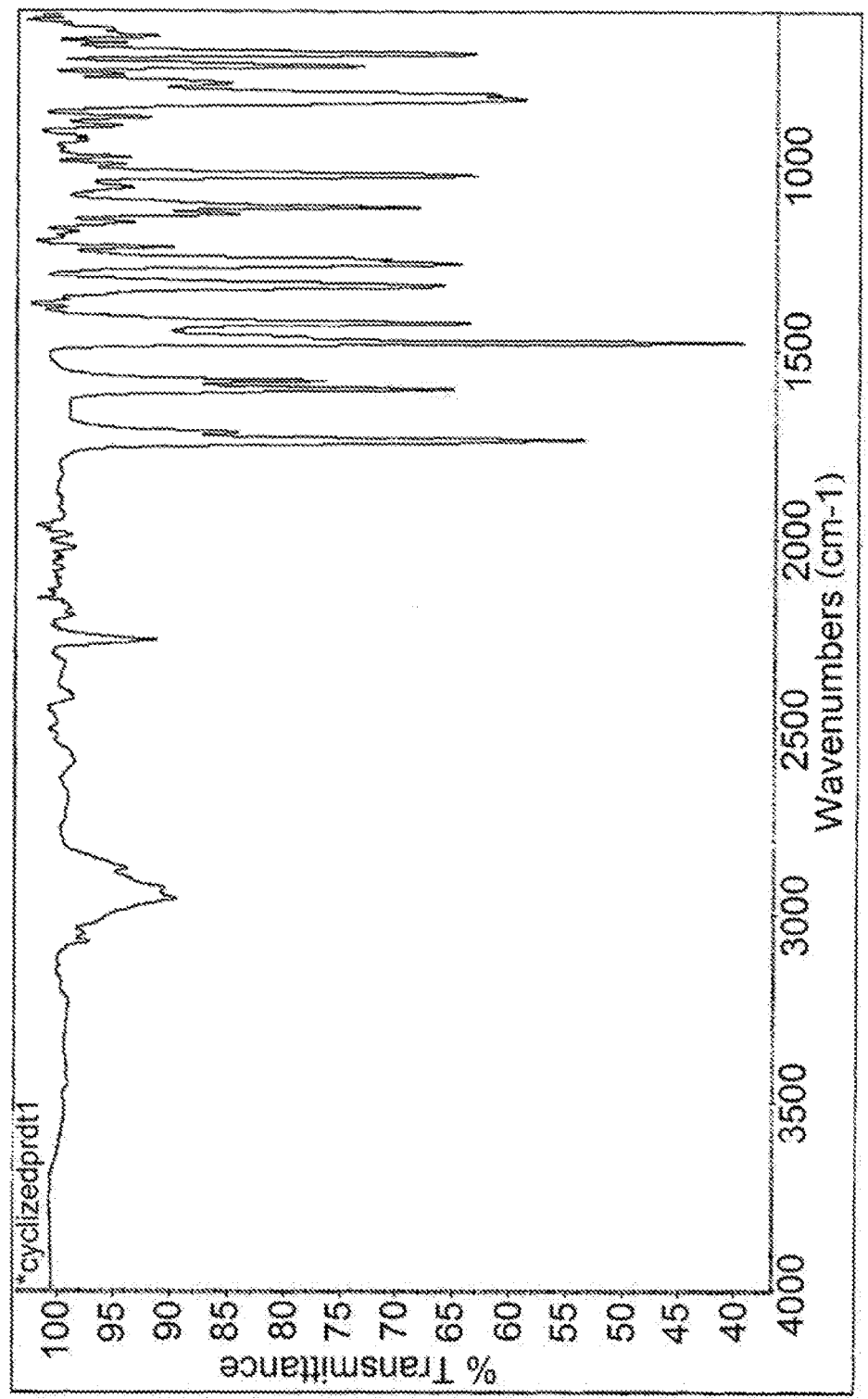
Figure 2:
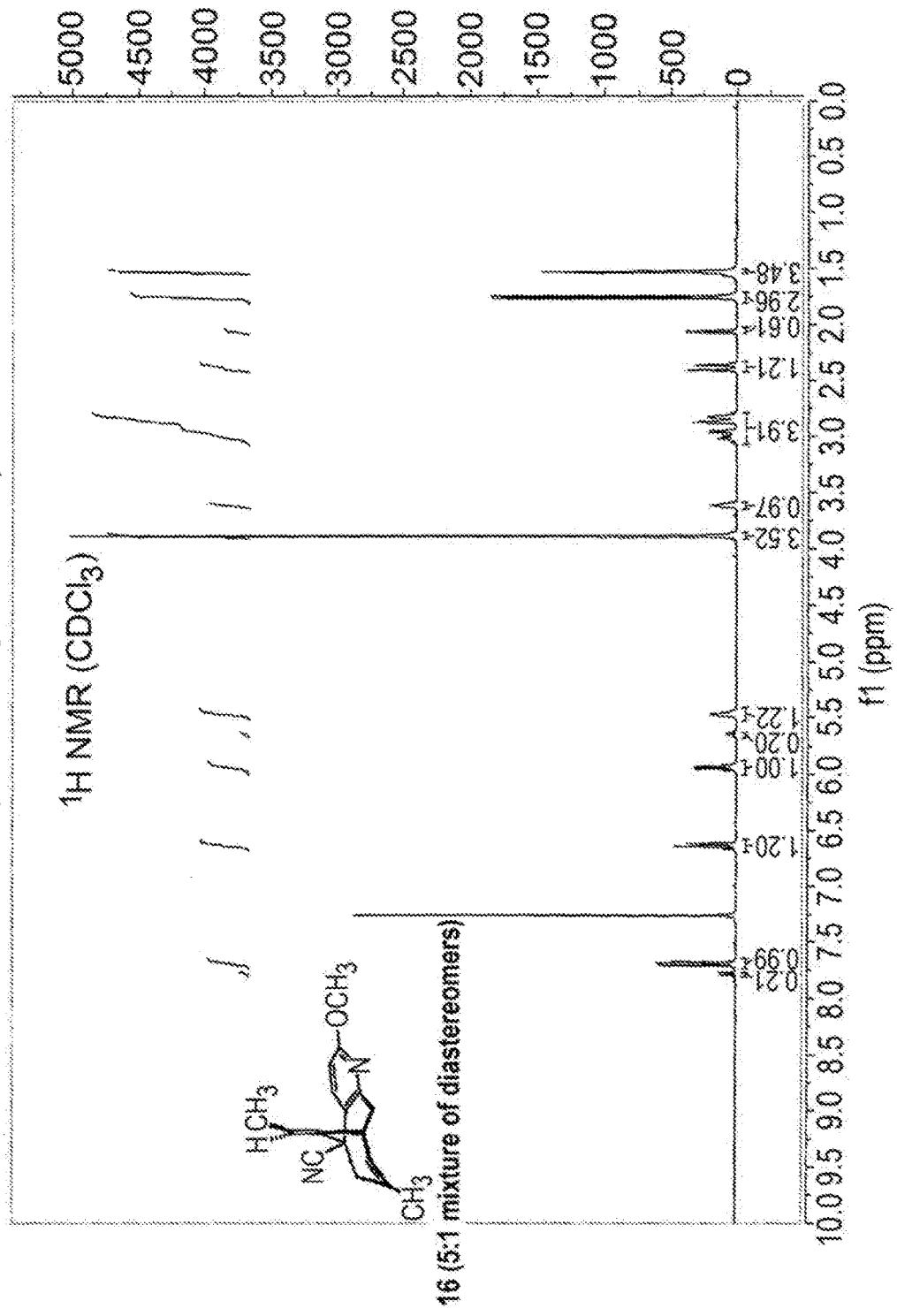
Figure 2:
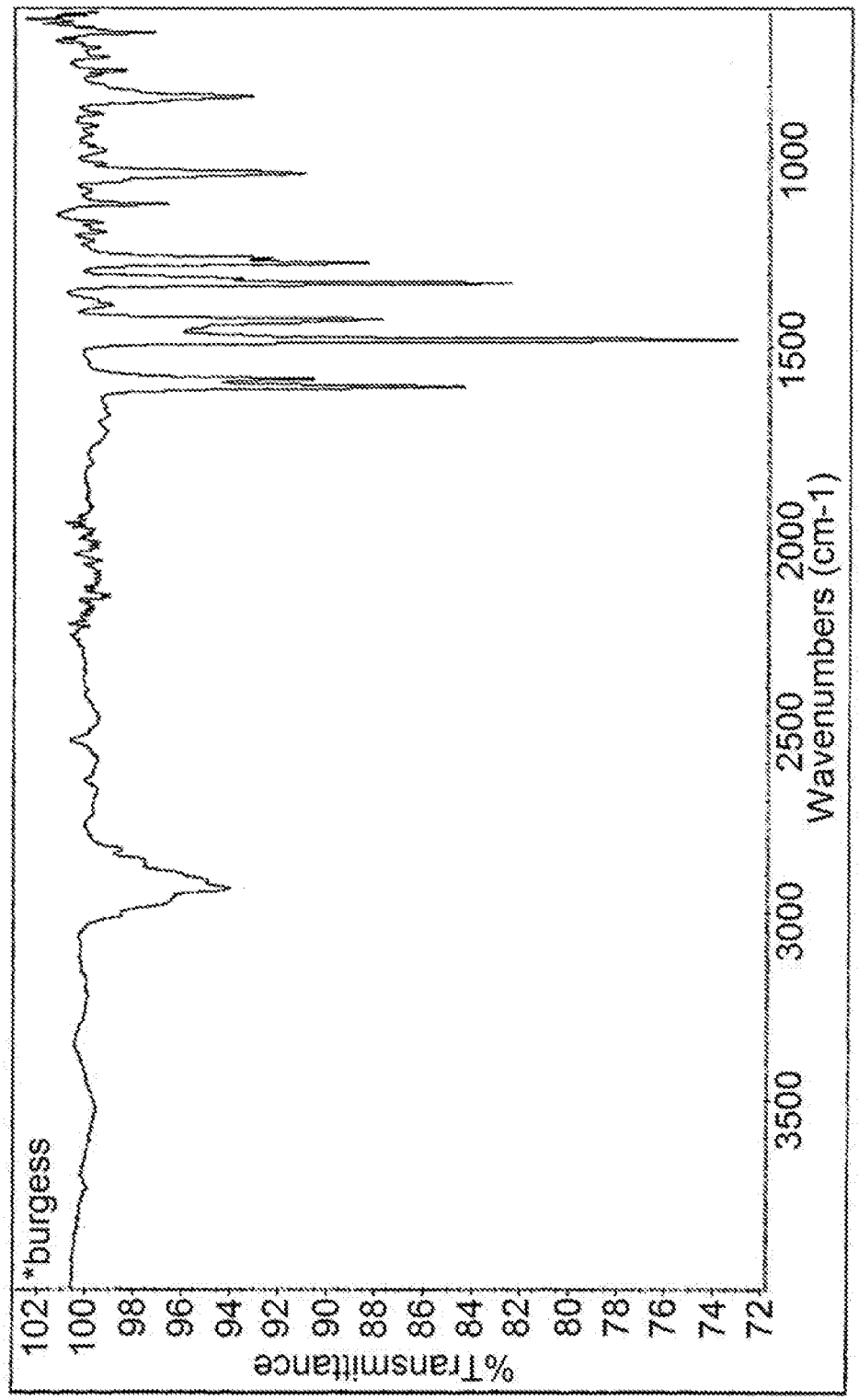
Figure 2:
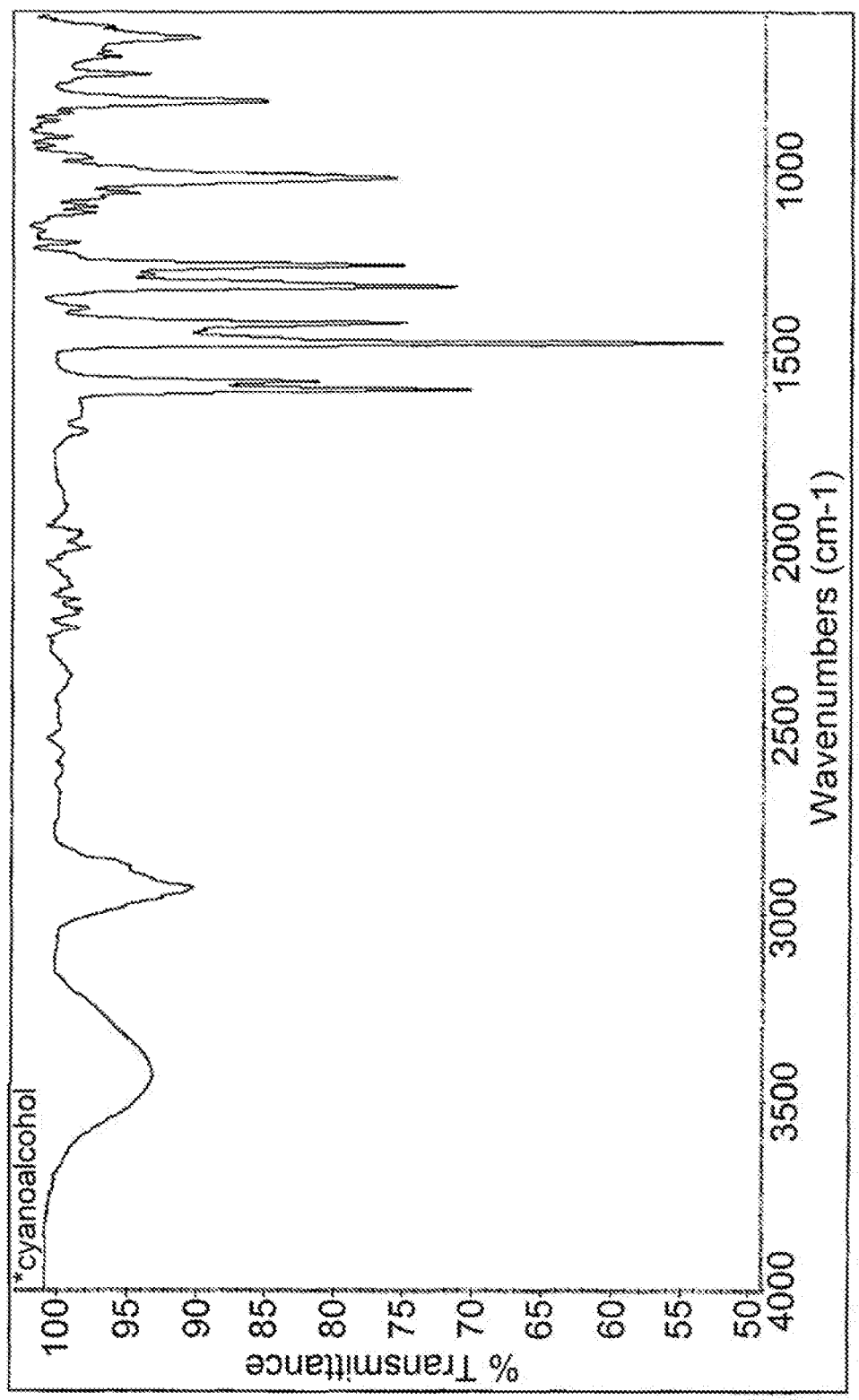
Figure 2:
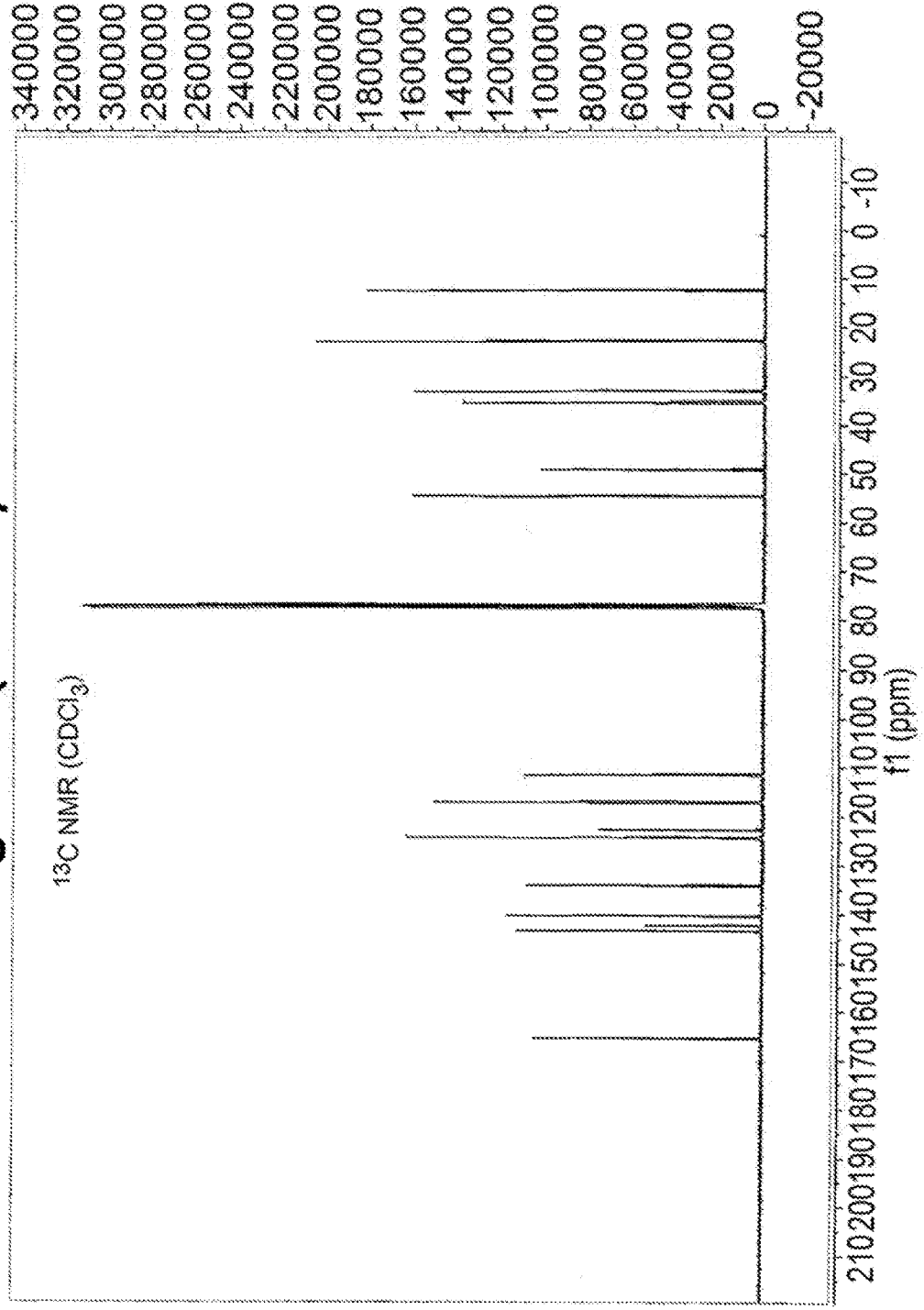
Figure 2:
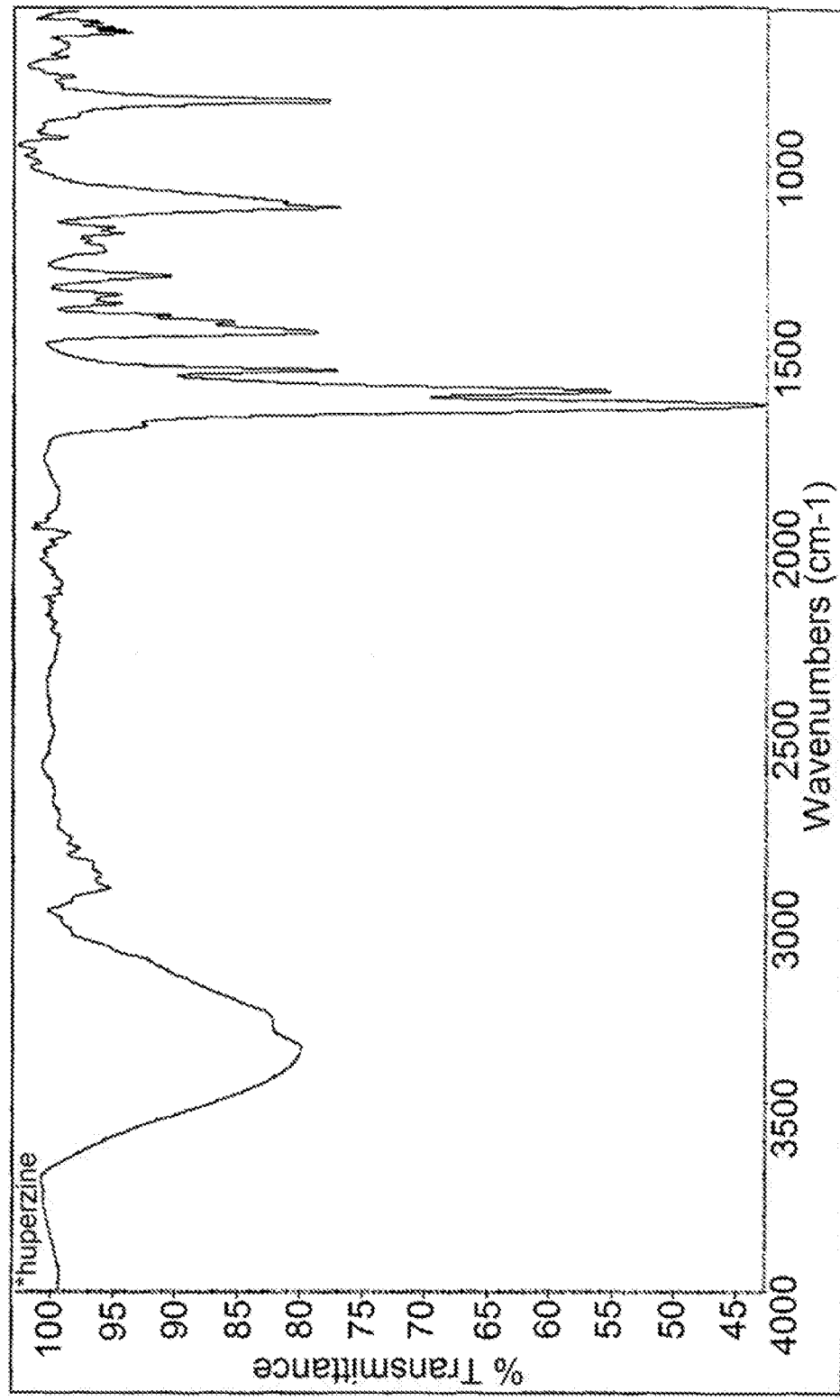
Figure 2:
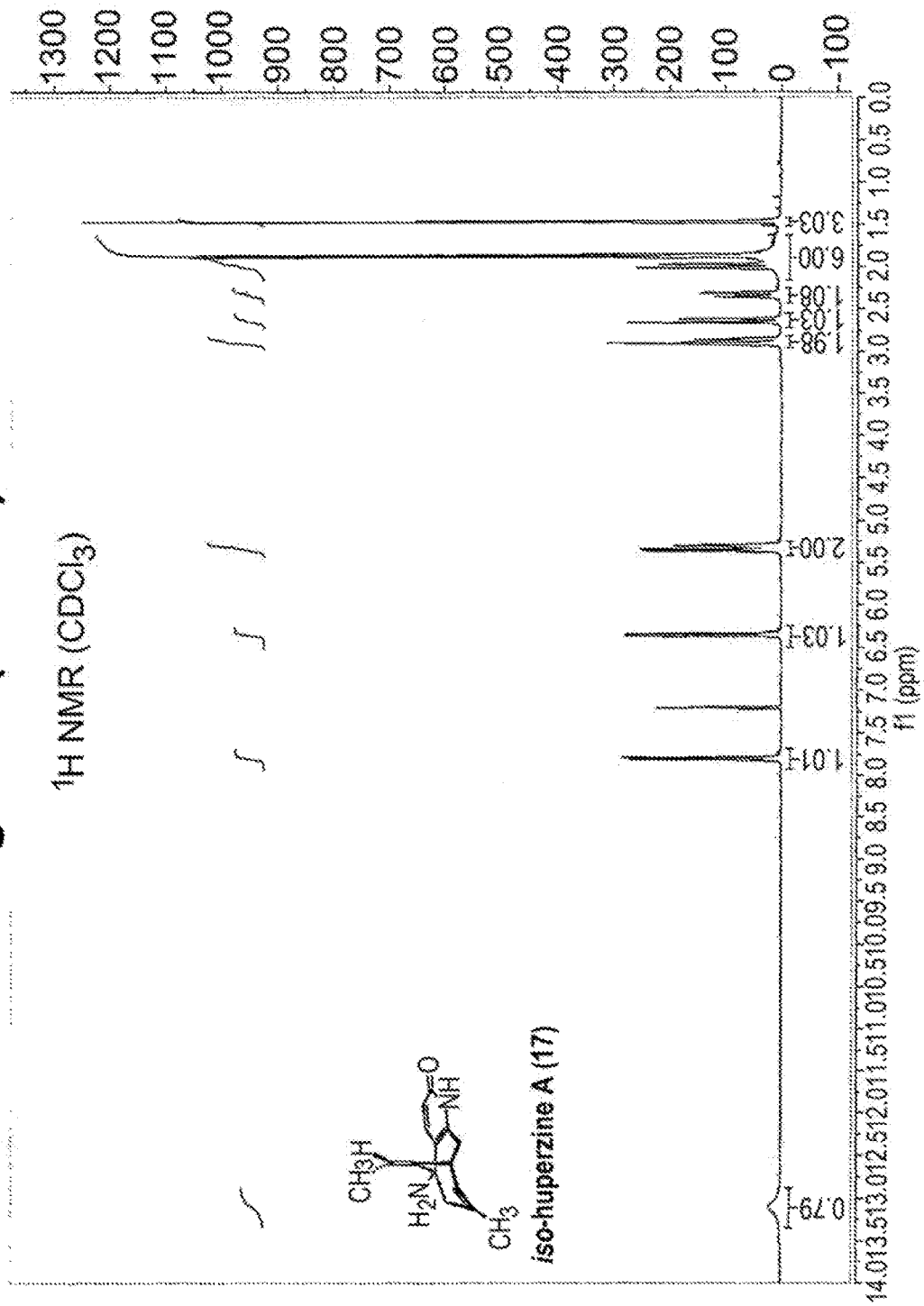
Figure 2:
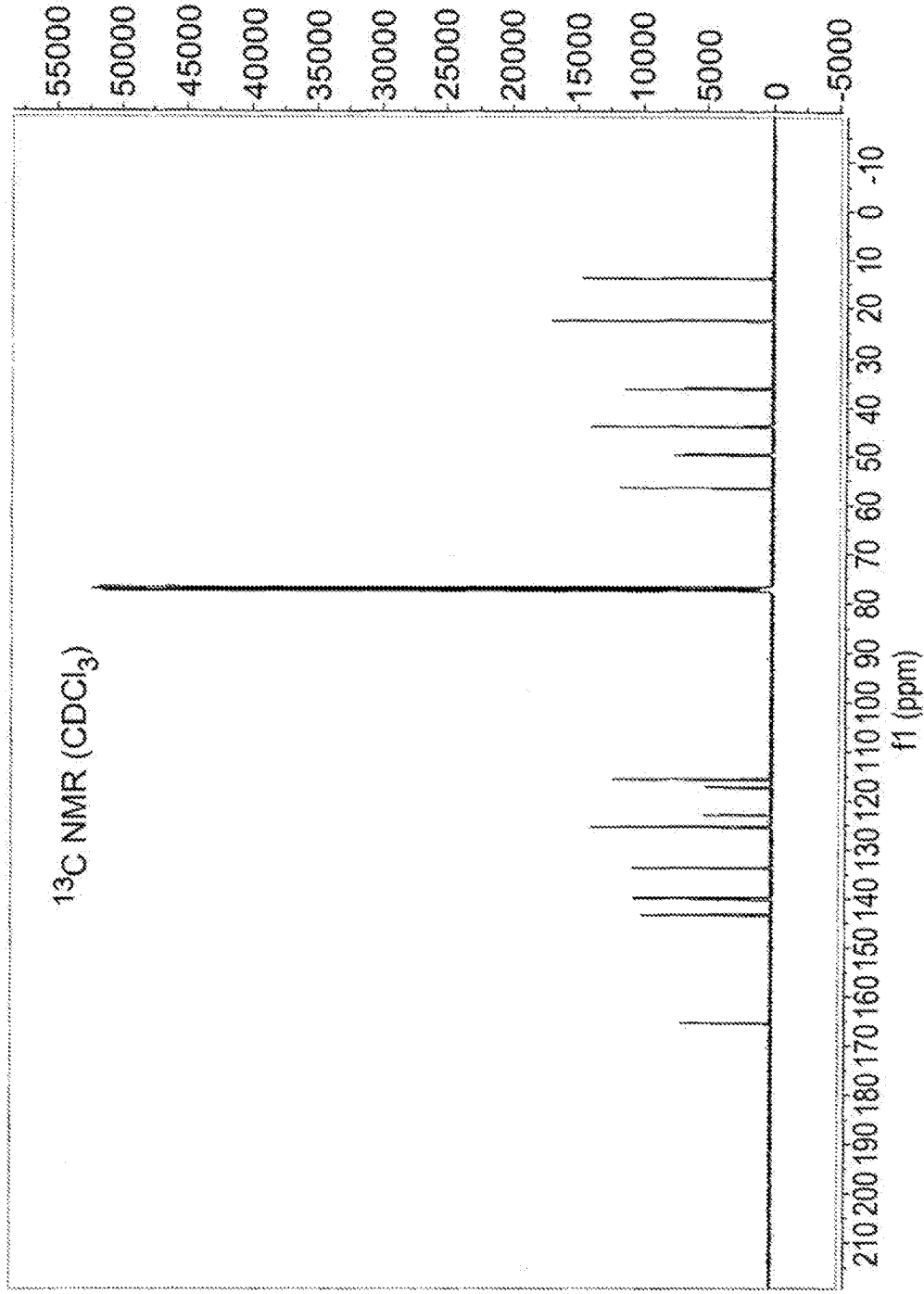
Figure 2:
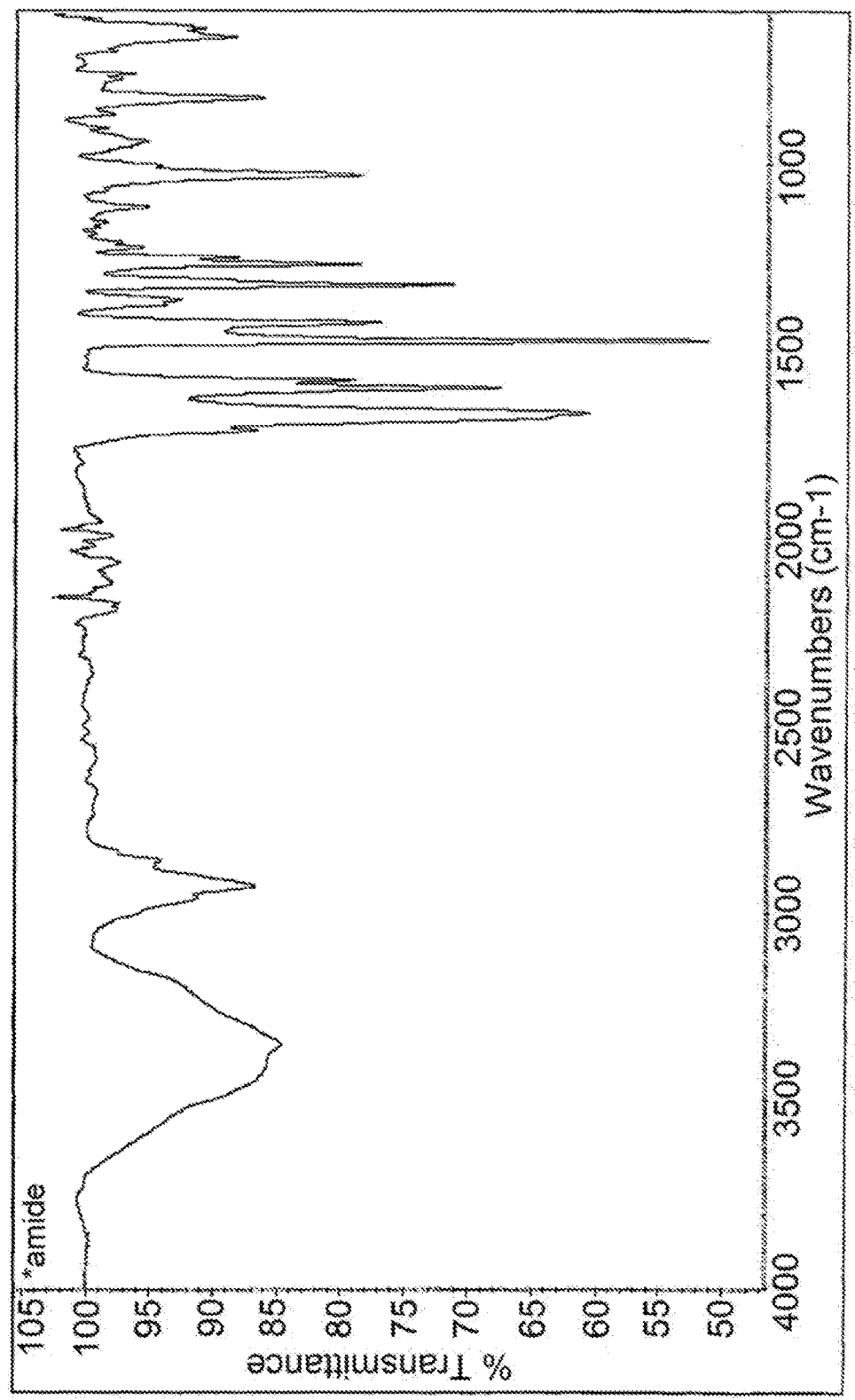

The following terms, among others, are used to describe the present invention. It is to be understood that a term which is not specifically defined is to be given a meaning consistent with the use of that term within the context of the present invention as understood by those of ordinary skill.

The term "compound", as used herein, unless otherwise indicated, refers to any specific chemical compound disclosed herein and includes tautomers, regioisomers, geometric isomers, and where applicable, optical isomers (e.g. enantiomers), stereoisomers (diastereomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal.

The symbol ══ is used in chemical compounds according to the present invention to signify that a bond between atoms is a single bond or double bond according to the context of the bond's use in the compound, which depends on the atoms (and substituents) used in defining the present compounds. Thus, where a carbon (or other) atom is used and the context of the use of the atom calls for a double bond or single bond to link that atom with an adjacent atom in order to maintain the appropriate valence of the atoms used, then that bond is considered a double bond or a single bond.

A "neurological disorder" includes, but is not limited to, an amyloid-related disorder such as Alzheimer's disease and the amyloid-disorders described below, psychiatric disorders such as Tourette's syndrome, posttraumatic stress disorder (PTSD), panic and anxiety disorders, obsessive-compulsive disorder, and schizophrenia, developmental disorders such as fragile X syndrome and autism, pain, drug addictions such as alcoholism, neurodegenerative diseases such as Parkinson's disease and Huntington's disease, as well as stroke and ischemic brain injury, amyotrophic lateral sclerosis, and epilepsy. "Neurological disorder" also includes any disorder, symptom, or effect associated with or relating to exposure to a neurotoxin, including but not limited to neurotoxins such as chemical warfare agents.

"Amyloid-related disorders" include diseases associated with the accumulation of amyloid which can either be restricted to one organ, "localized amyloidosis", or spread to several organs, "systemic amyloidosis". Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic amyloidosis found in long-term hemodialysis patients. Localized forms of amyloidosis include, without limitation, type II diabetes and any related disorders thereof, neurodegenerative diseases such as scrapie, bovine spongiform encephalitis, Creutzfeldt-Jakob disease, Alzheimer's disease, senile systemic amyloidosis (SSA), Cerebral Amyloid Angiopathy, Parkinson's disease, and prion protein related disorders (e.g. prion-related encephalopathies), and rheumatoid arthritis.

The term "effective" is used herein, unless otherwise indicated, to describe an amount of a compound or composition which, in context, is used to produce or effect an intended result, whether that result relates to the inhibition of the effects of a neurological disorder, or to potentiate the effects of a supplementary treatment used in treating a neurological disorder (e.g. an antipsychotic drug or as otherwise described herein). This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for or afflicted by a neurological disorder, including lessening or suppression of at least one symptom of a neurological disorder, delay in progression of a neurological disorder or the reduction in likelihood of the onset of a neurological disorder. Treatment, as used herein, encompasses both prophylactic and therapeutic treatment.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, the term "salt" shall mean a pharmaceutically acceptable salt, consistent with the use of the compounds as pharmaceutical agents.

The term "co-administration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time.

For example, compounds according to the present invention may be administered with one or more agents that are useful in treating an amyloid-related disorder or a stage of an amyloid-related disorder. The type of co-administered agent can vary widely depending on the particular clinical context. For example, co-administered agents can include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

More specifically, in the case of Alzheimer's disease, useful additional agents include but are not limited to cholinesterase inhibitors, antioxidant Ginkobiloba extract, nonsteroidal anti-inflammatory agents, and non-specific NMDA antagonists, such as Ebixa® (Memantine). In the case of Parkinson's disease, useful additional agents include but are not limited to carbidopa/levodopa (Sinemet-Bristol Myers Squibb), which controls temor, bradykinesia, balance, and rigidity. Other therapies include dopamine agonists, carbidopa/levodopa therapy, COMT inhibitors, anticholinergics, and MAO inhibitors such as selegiline/deprenyl. In the case of Type II diabetes, useful additional agents include but are not limited to biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2), glucagon-like peptide-1 (GLP-1), and dipeptidyl peptidase IV (DP4) inhibitors.

The terms "antagonist" and "inhibitor" are used interchangeably to refer to an agent, especially including chemical agents which are specifically disclosed herein that decreases or suppresses a biological activity, such as to repress an activity of a neurological disorder. "Modulators of a neurological disorder" either repress or enhance an activity of a neurological disorder.

The term "acyl" is art-recognized and refers to a group represented by the general formula hydrocarbylC(O)—, preferably alkylC(O)—.

The term "acylamino" is art-recognized and refers to a moiety having an amino group and an acyl group and may include substitutents on same as otherwise disclosed herein.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed herein, except where stability of the moiety is prohibitive. For example, substitution of alkenyl groups by one or more alkyl, carbocyclyl, aryl, heterocyclyl, or heteroaryl groups is contemplated.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$-substituent, where m is 0 to 6 and the substituent is an aryl or substituted aryl group, a cycloalkyl group, a cycloalkenyl, a heterocycle or a polycycle (two or three ringed), each of which may be optionally substituted.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 10 or fewer carbon atoms in its backbone (e.g., C$_1$-C$_{10}$ for straight chains, C$_1$-C$_{10}$ for branched chains), and more preferably 8 or fewer, and most preferably 6 or fewer. Likewise, preferred cycloalkyls have from 3-10 carbon atoms in their ring structure, and more preferably have 5, 6, 7 or 8 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety or as otherwise described herein. It will be understood by those skilled in the art that the individual substituent chemical moieties can themselves be substituted. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary, non-limiting substituted alkyls are described herein. Cycloalkyls can be further substituted with alkyls, alkenyls, alkynyls, alkoxys, alkylthios, aminoalkyls, carbonyl-substituted alkyls, —CF$_3$, —CN, and the like.

Analogous substitutions can be made to alkenyl and alkynyl groups to produce, for example, without limitation, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

Unless the number of carbons is otherwise specified, "lower alkyl" as used herein means an alkyl group, as defined above, but having from one to eight carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—substituent, wherein m is 0 or an integer from 1 to 8 and substituent is the same as defined herein and as otherwise below (R$_9$ and R$_{10}$ for amine/amino). Representative alkylthio groups include methylthio, ethylthio, and the like.

The terms "amine" and "amino" are art-recognized and refer to both unsubstituted and substituted amines, e.g., a moiety that can be represented, without limitation, by the general formula:

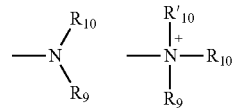

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In certain such embodiments, neither R$_9$ and R$_{10}$ is attached to N by a carbonyl, e.g., the amine is not an amide or imide, and the amine is preferably basic, e.g., its conjugate acid has a pK$_a$ above 7. In even more preferred embodiments, R$_9$ and R$_{10}$ (and optionally, R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group. Each of the groups which is bonded to the amine group, where applicable, may be optionally substituted.

The term "amido" is art-recognized as an amino-substituted carbonyl and includes a moiety that can be represented by the general formula:

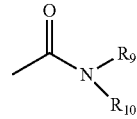

wherein R$_9$, R$_{10}$ are as defined above. Preferred embodiments of the amide will not include imides that may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring or aromatic groups containing from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaromatics" or "heteroaryl groups". The aromatic ring can be substituted at one or more ring positions with such substituents as otherwise described herein, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

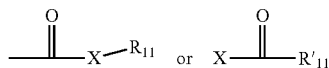

wherein X is a bond or represents an oxygen or a sulfur, and $R_{11}$ represents, for example without limitation, a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as otherwise described herein without limitation. Where X is oxygen and $R^{11}$ or $R'_{11}$ is not hydrogen, the formula represents an "ester". Where X is oxygen, and $R_{11}$ is as defined above, the moiety is referred to herein as a carboxyl group, and particularly when $R_{11}$ is hydrogen, the formula represents a "carboxylic acid". Where X is oxygen, and $R'_{11}$ is hydrogen, the formula represents a "formate". In general, where the oxygen atom of the above formula is replaced by sulfur, the formula represents a "thiocarbonyl" group. Where X is sulfur and $R_{11}$ or $R'_{11}$ is not hydrogen, the formula represents a "thioester." Where X is sulfur and $R_{11}$ is hydrogen, the formula represents a "thiocarboxylic acid." Where X is sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "electron withdrawing group" refers to chemical groups which withdraw electron density from the atom or group of atoms to which electron withdrawing group is attached. The withdrawal of electron density includes withdrawal both by inductive and by delocalization/resonance effects. Examples of electron withdrawing groups attached to aromatic rings include perhaloalkyl groups, such as trifluoromethyl, halogens, azides, carbonyl containing groups such as acyl groups, cyano groups, and imine containing groups.

The term "ester", as used herein, refers to a group —C(O)O-substituent wherein the substituent represents, for example, a hydrocarbyl or other substituent as is otherwise described herein.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heterocycle" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, without limitation, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above without limitation, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like, and as otherwise described herein.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include up to 20-membered polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

Thus, the terms "heterocyclyl", "heterocycle", and "heterocyclic" refer to substituted or unsubstituted aromatic or non-aromatic ring structures (which can be cyclic, bicyclic or a fused ring system), preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "5- to 20-membered heterocyclic group" or "5- to 14-membered heterocyclic group" as used throughout the present specification refers to an aromatic or non-aromatic cyclic group having 5 to 20 atoms, preferably 5 to 14 atoms forming the cyclic ring(s) and including at least one hetero atom such as nitrogen, sulfur or oxygen among the atoms forming the cyclic ring, which is a "5 to 20-membered, preferably 5- to 14-membered aromatic heterocyclic group" (also, "heteroaryl" or "heteroaromatic") in the former case and a "5 to 20-membered", preferably a "5- to 14-membered non-aromatic heterocyclic group" in the latter case.

Among the heterocyclic groups which may be mentioned include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole.

As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 20-membered heterocyclic groups, preferably 3 to 14-membered heterocyclic groups and all subsets of heterocyclic groups (including non-heteroaromatic or heteroaromatic) subsumed under the definition of heterocyclic group are 3 to 20-membered heterocyclic groups, preferably 3 to 14-membered heterocyclic groups.

The term "8 to 20-membered heterocyclic group", or "8 to 14-membered heterocyclic group" refers to an aromatic or non-aromatic fused bicyclic or tricyclic group having 8 to 20, preferably 8 to 14 atoms forming the cyclic rings (two or three rings) and include at least one hetero atom such as nitrogen, sulfur or oxygen among the atoms forming the cyclic rings, which is a "8 to 20-membered", preferably a "8- to 14-membered aromatic heterocyclic group" (also, "heteroaryl" or "heteroaromatic") in the former case and a "8 to 20-membered", preferably a "8- to 14-membered non-aromatic heterocyclic group" in the latter case. "8 to 20-membered heterocyclic groups" and "8 to 14 membered heterocyclic groups" are represented by fused bicyclic, tricyclic and tetracyclic ring structures containing nitrogen atoms such as indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "5- to 14-membered non-aromatic heterocyclic group" as used throughout the present specification refers to non-aromatic cyclic group having 5 to 14 atoms forming the cyclic ring and including at least one hetero atom such as nitrogen, sulfur or oxygen among the atoms forming the cyclic ring. As specific examples there may be mentioned non-aromatic heterocycles such as pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimideandsuccinimide. As examples of the "5- to 14-membered non-aromatic heterocyclic group" there may be mentioned preferably, pyrrolidinyl, piperidinyl and morpholinyl, and more preferably pyrrolidinyl, piperidinyl, morpholinyl and pyrrole.

The term "8- to 14-membered non-aromatic heterocyclic group" as used throughout the present specification refers to a non-aromatic fused cyclic ring system (generally with two or three rings) having 8 to 14 atoms forming the cyclic rings (bicyclic or tricyclic) and including at least one hetero atom such as nitrogen, sulfur or oxygen among the atoms forming the cyclic rings.

The term "5- to 14-membered heterocyclic group" as used throughout the present specification refers to an aromatic or non-aromatic cyclic group having 5 to 14 atoms forming the cyclic ring and including at least one hetero atom such as nitrogen, sulfur or oxygen among the atoms forming the cyclic ring, which is a "5- to 14-membered aromatic heterocyclic group" in the former case and a "5- to 14-membered non-aromatic heterocyclic group" in the latter case. Specific examples of the "5- to 14-membered heterocyclic group" therefore include specific examples of the "5- to 14-membered aromatic heterocyclic group" and specific examples of the "5- to 14-membered non-aromatic heterocyclic group".

As the "5- to 14-membered heterocyclic group" there may be mentioned preferably pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline and carbostyryl, among others.

The term "6- to 14-membered aromatic heterocyclic group" as used throughout the present specification refers to those substituents defined by "5- to 14-membered aromatic heterocyclic group" which have 6 to 14 atoms forming the cyclic ring. As specific examples there may be mentioned pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole and phenothiazine*. "8 to 14-membered aromatic heterocyclic groups" refer to those substituents or radicals having 8 to 14 atoms forming fused two or three cyclic ring systems. Specific examples include indole, quinoline, isoquinoline, quinolizine, phthalazine, naphthyridine, quinazoline, cinnoline, acridine, benzothiophene, benzofuran, benzothiazole, pyrrolopyrimidine, pyrrolopyrazine, furopyrimidine and phenothiazine, among numerous others.

The term "6- to 14-membered heterocyclic group" as used throughout the present specification refers to those substituents defined by "5- to 14-membered heterocyclic group" which have 6 to 14 atoms forming the cyclic ring(s). As specific examples there may be mentioned piperidinyl, piperazinyl, N-methylpiperazinyl, morpholinyl, tetrahydropyranyl, 1,4-dioxane and phthalimide.

The term "3 to 7-membered heterocyclic group" as used throughout the present specification refers to those heterocyclic substituents which have 3 to 7 atoms forming the cyclic ring, preferably 5 to 6 atoms forming the cyclic ring.

The term "8 to 14-membered heterocyclic group" as used throughout the present specification refers to those substituents defined "8- to 14-membered heterocyclic groups which have 8 to 14 atoms forming the fused cyclic ring system.

The term "heterocyclylalkyl", as used herein, refers to an alkyl group substituted with a heterocycle group.

The term "hydrocarbyl", as used herein, refers to an optionally substituted group that is bonded through a carbon atom and typically has at least one carbon-hydrogen bond and a primarily carbon backbone, but may optionally include heteroatoms. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The terms "polycyclyl" or "polycyclic group" refer to two or more rings (e.g., cycloalkyls, cycloalkenyls, cycloalkynyls, aryls and/or heterocyclyls) in which two or more atoms are common to two adjoining rings, e.g., the rings are "fused rings". Rings that are joined through non-adjacent atoms are termed "bridged" rings. Each of the rings of the polycycle can be substituted with, without limitation, such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, $2^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic, non-aromatic and inorganic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents (groups) as otherwise described herein, for example, a halogen, a hydroxyl, a carbonyl (such as a carboxyl, an alkoxycarbonyl, a formyl, or an acyl), an ether, a thioether, a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on a moiety or chemical group can themselves be substituted.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. It is acknowledged that the term "unsubstituted" simply refers to a hydrogen substituent or no substituent within the context of the use of the term.

Preferred substituents for use in the present invention include, for example, within context, hydroxyl, carboxyl, cyano ($C\equiv N$), nitro ($NO_2$), halogen (preferably, 1, 2 or 3 halogens, especially on an alkyl, especially a methyl group such as a trifluoromethyl), thiol, alkyl group (preferably, $C_1$-$C_6$, more preferably, $C_1$-$C_3$), alkoxy group (preferably, $C_1$-$C_6$ alkyl or aryl, including phenyl), ether (preferably, $C_1$-$C_6$ alkyl or aryl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), thioether (preferably, $C_1$-$C_6$ alkyl or aryl) (preferably, $C_1$-$C_6$ alkyl or aryl), thioester (preferably, $C_1$-$C_6$ alkyl or aryl), halogen (F, Cl, Br, I), nitro or amine (including a five- or six-membered cyclic alkylene amine, including a $C_1$-$C_6$ alkyl amine or $C_1$-$C_6$ dialkyl amine), alkanol (preferably, $C_1$-$C_6$ alkyl or aryl), or alkanoic acid (preferably, $C_1$-$C_6$ alkyl or aryl). More preferably, the term "substituted" shall mean within its context of use alkyl, alkoxy, halogen, hydroxyl, carboxylic acid, nitro and amine (including mono- or di-alkyl substituted amines). Any substitutable position in a compound according to the present invention may be substituted in the present invention, but preferably no more than 5, more preferably no more than 3 substituents are present on a single ring or ring system. Preferably, the term "unsubstituted" shall mean substituted with one or more H atoms.

The term "sulfamoyl" is art-recognized and includes a moiety represented by the general formula:

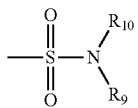

where $R_9$ and $R_{10}$ are substituents as described above.

The term "sulfate" is art-recognized and includes a moiety represented by the general formula:

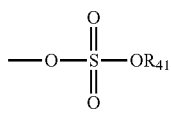

Where $R_{41}$ is an electron pair, hydrogen, alkyl, cycloalkyl or aryl.

The term "sulfonamido" is art-recognized and includes a moiety represented by the general formula:

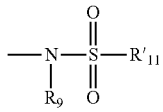

Where $R_9$ and $R'_{11}$ are as described above.

The term "sulfonate" is art-recognized and includes a moiety represented by the general formula:

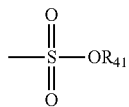

Where $R_{41}$ is an electron pair, hydrogen, alkyl, cycloalkyl or aryl.

The term "sulfoxido" or "sulfinyl" is art-recognized and includes a moiety represented by the general formula:

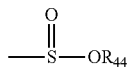

where $R_{44}$ is is selected from the group consisting of hydrogen, alkyl, alkenyl, alkynyl, cycloalkyl, heterocyclyl, aralkyl or aryl., which groups may be optionally substituted.

The term "thioester" is art-recognized and is used to describe a group —C(O)SR$^9$ or —SC(O)R$^9$ wherein R$^9$ represents an optionally substituted hydrocarbyl group as otherwise described herein.

As used herein, the definition of each expression of alkyl, m, n, etc. when it occurs more than once in any structure, is intended to reflect the independence of the definition of the same expression in the structure.

By way of example, certain preferred aromatic and aliphatic rings and their derivatives and substituents which may be used as pharmacophores or substituents in compounds according to the present invention include, but are not limited to, phenyl, benzyl, pyridine, cyclohexadiene, dihydropyridine, tetrahydropyridine, piperidine, pyrazine, tetrahydro-pyrazine, dihydro-pyrazine, piperazine, pyrimidine, dihydro-pyrimidine tetrahydro-pyrimidine, hexahydro-pyrimidine, pyrimidinone, triazine, dihydro-triazine, tetrahydro-triazine, triazinane, tetrazine, dihydro-tetrazine, tetrahydro-tetrazine, tetrazinane, pyrrol, dihydro-pyrrole, pyrrolidine, imidazolidine, dihydro-imidazolidine, imidazole, dihydro-imidazole, azetidine, triazole, dihydro-triazole, triazolidine, tetrazole, dihydro-tetrazole, tetrazolidine, diazepane, tetrahydro-diazepine, dihydro-diazepine, diazepine, oxazole, dihydrooxazole, oxazolidine, isoxazole, dihydroisoxazole, isoxazolidine, thiazole, dihydrothiazole, thiazolidine, isothiazole, dihydroisothiazole, isothiazolidine, oxadiazole, dihydro-oxadiazole, oxadiazolidine, thiadiazole, dihydro-thidiazole, thiadiazolidine, oxazinane, dihydro-oxazinane, dihydro-oxazine, oxazine (including morpholine), thiazinane, dihydro-thiazinane, dihydro-thiazine, thiazine (including thiomorpholine), thiazine, furan, dihydrofuran, tetrahydrofuran, thiophene, pyridazine-3,6-dione, tetrahydrothiophene, dihydrothiophene, tetrahydrothiophene, dithiolane, dithiole, dithiolone, dioxolane, dioxole, oxathiole, oxathiolane, pyridinone, dioxane, dioxanedione, benzoquinone, dihydro-dioxine, dioxine, pyran, 3,4-dihydro-2H-pyran, pyranone, 2H-pyran-2,3(4H)-dione, oxathiane, dihydro-oxathiine, oxathiine, oxetane, thietane, thiazeto, cyclohexadienone, lactam, lactone, piperazinone, pyrroledione, cyclopentenone, oxazete, oxazinanone, dioxolane, 3,4-dihydro-2H-thiopyran 1,1-dioxide, dioxolanone, oxazolidinone, oxazolone, thiane 1-oxide, thiazinane 1-oxide, tetrahydro-thiopyran, thiane 1,1-dioxide, dioxazinane, pyrazolone, 1,3-thiazete, thiazinane 1,1-dioxide, 6,7-dihydro-5H-1,4-dioxepine, 1,2-dihydropyridazin-3(4H)-one, pyridine-2,6(1H,3H)-dione, and sugar (glucose, mannose, galactose, fucose, fructose, ribose). Bicyclic and fused rings include, for example, naphthyl, quinone, quinolinone, dihydroquinoline, tetrahydroquinoline, naphthyridine, quinazoline, dihydroquinazoline, tetrahydroquinazoline, quinoxaline, dihydroquinazoline, tetrahydroquinazoline, pyrazine, quinazoline-2,4(1H,3H)-dione, isoindoline-1,3-dione, octahydro-pyrrolo-pyridine, indoline, isoindoline, hexahydroindolone, tetrahydropyrrolo oxazolone, hexahydro-2H-pyrrolo[3,4-d]isoxazole, tetrahydro-1,6-naphthyridine, 2,3,4,5, 6,7-hexahydro-1H-pyrrolo[3,4-c]pyridine, 1H-benzo[d] imidazole, octahydropyrrolo[3,4-c]pyrrole, 3-azabicyclo [3.1.0]hexane, 7-azabicyclo[2.2.1]hept-2-ene, diazabicycloheptane, benzoxazole, indole, 1,4-diazabicyclo[3.3.1] nonane, azabicyclo-octane, naphthalene-1,4-dione, indene, dihydroindene, 2,3,3a,7a-tetrahydro-1H-isoindole, 2,3,3a,4, 7,7a-hexahydro-1H-isoindole, 1,3-dihydroisobenzofuran, 1-methyl-3a,4,5,6,7,7a-hexahydro-H-indole, 3-azabicyclo [4.2.0]octane, 5,6-dihydrobenzo[b]thiophene, 5,6-dihydro-4H-thieno[2,3-b]thiopyran, 3,4-dihydropyrazin-2(1H)-one, 2H-benzo[b][1,4]thiazine, naphthyridin-4(1H)-one, octahydropyrrolo[1,2-a]pyrazine, imidazo-pyridazine, tetrahydroimidazo-pyridazine, tetrahydropyridazine, thiazinone, 5-thia-1-azabicyclo[4.2.0]oct-2-en-8-one, 4-thia-1-azabicyclo[3.2.0]heptan-7-one, 1,6,7,8-tetrahydroimidazo[4,5-d][1, 3]diazepine, 8H-thiazolo[4,3-c][1,4]oxazin-4-ium, 8H-thiazolo[4,3-c][1,4]thiazin-4-ium, pteridine, thiazolo[3,4-a] pyrazin-4-ium, 7-(methylimino)-7H-pyrrolo[1,2-c]thiazol- 4-ium, thiazolo-pyrazine, 3,7-dioxabicyclo[4.1.0]hept-4-ene, 6,7-dihydro-5H-pyrrolo[1,2-a]imidazole, 3,3a-dihydrofuro[3,2-b]furan-2(6aH)-one, tetrahydro-3 aH-[1,3]dioxolo[4,5-c]pyrrole, 7-ethylidene-7H-pyrrolo[1,2-c]thiazol-4-ium, hexahydro-1H-pyrrolo[2,1-c][1,4]oxazine, 6,7,8,8a-tetrahydro-1H-pyrrolo[2,1-c][1,4]oxazine, 2-azabicyclo[2.2.2]oct-2-ene, 6,6a-dihydrothieno[3,2-b]furan-5(3 aH)-one, 4,5-dihydropyridin-3 (2H)-one, 4,7a-dihydro-3 aH-[1,3]dioxolo[4,5-c]pyran, 6,7-dihydro-1H-furo[3,4-c]pyran-1,3(4H)-dione, 3,3a,4,7a-tetrahydro-2H-furo[2,3-b]pyran, 2,4a,7,7a-tetrahydro-1H-cyclopenta[c]pyridine, 4H-pyrano[3,2-b]pyridine-4,8(5H)-dione, 1,2,3,3a,4,7a-hexahydropyrano[4,3-b]pyrrole, 2,3,8,8a-tetrahydroindolizin-7(1H)-one, octahydro-1H-pyrido[1,2-a]pyrazin-1-one, 2,6,7,8,9,9a-hexahydro-1H-pyrido[1,2-a]pyrazin-1-one, 6,7,8,8a-tetrahydropyrrolo[1,2-a]pyrazin-1(2H)-one, hexahydropyrrolo[1,2-a]pyrazin-1(2H)-one, bicyclo[2.2.1]hepta-2,5-diene.

Spiro moieties: 1,5-dioxaspiro[5.5]undecane, 1,4-dioxaspiro[4.5]decane, 1,4-diazabicyclo[3.2.1]octane, 5-azaspiro[2.5]octane, 5-azaspiro[2.4]heptane, 3,9-diaza-6-azoniaspiro[5.5]undecane, 3,4-dihydrospiro[benzo[b][1,4]oxazine-2,1'-cyclohexane], 7-oxa-4-azaspiro[2.5]oct-5-ene.

Pharmaceutical compositions comprising combinations of an effective amount of at least one STEP-modulating compound according to the present invention, and one or more of the compounds otherwise described herein, all in effective amounts, in combination with a pharmaceutically effective amount of a carrier, additive or excipient, represents a further aspect of the present invention.

The compositions used in methods of treatment of the present invention, and pharmaceutical compositions of the invention, may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in methods of treatment of the present invention, and pharmaceutical compositions of the invention, may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intra-hepatic, intralesional and intracranial injection or infusion techniques. Preferably, the compositions are administered orally, intraperitoneally or intravenously.

Sterile injectable forms of the compositions used in methods of treatment of the present invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional non-antibody attracting compound which may be used to treat cancer, prostate cancer or metastatic prostate cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from or at risk of developing a neurological disorder can be treated by administering to the patient (subject) an effective amount of (−)-huperzine A and related aspects and embodiments according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating a neurological disorder or ameliorate the secondary effects and conditions associated with a neurological disorder. This treatment can also be administered in conjunction with other conventional therapies, such as drugs used to treat cognitive and behavioral symptoms of Alzheimer's patients (e.g. Reminyl®, Exelon®, Aricept®, Cognex®, and Namenda®).

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent, as are topically administered compositions.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Exemplary Processes and Compounds of the Invention

Scheme 1 below illustrates one preferred synthesis within the scope of the instant invention.

The descriptors a, b, c, indicate steps that were performed with intermittent aqueous work-up of products, but without purification of the product. Steps 3a and 3d were accomplished by evaporation of volatiles, and addition of reagents directly to reaction flask (no intermittent work-up). The route to 5 proceeds in 55% overall yield from 1.

The route can begin with the inexpensive, enantiomerically pure reagent (+)-pulegone, which may be transformed to 1 by a four-step procedure, which has been previously published. Lee, H. W.; Ji, S. K.; Lee, I.-Y. C.; Lee, J. H. *J. Org. Chem.* 1996, 61, 254.

There are many novel features associated with exemplary scheme 1. For example, the existing stereochemistry of the starting material can be utilized to control the relative stereochemistry in the product 2.

The conversion of 2 to 3 is not suggested by known techniques. In particular, step 2b is the first known example of cyclization of a β-ketonitrile.

The Wittig reaction (step 2c) is also not suggested by known techniques. Prior workers had obtained mixtures of olefin isomers in the products. We optimized both the substrate and the reaction conditions to obtain a desirable outcome.

The transformation of 4 to 5 is also not suggested by known techniques. Prior workers had relied on a two-step procedure for elimination of the alcohol function (steps 4a). We found that this can be conducted efficiently in one reaction flask using the Burgess reagent.

Step 4b is also not suggested by known techniques. The application of the platinum catalyst in the hydration of nitriles to primary amides is rare. Additionally, it is known in the literature that such catalysts are generally ineffective for the hydration of tertiary nitriles (such as that found in 4). Thus, the direct hydration of the nitrile using this catalyst constitutes an advance over known synthetic methods.

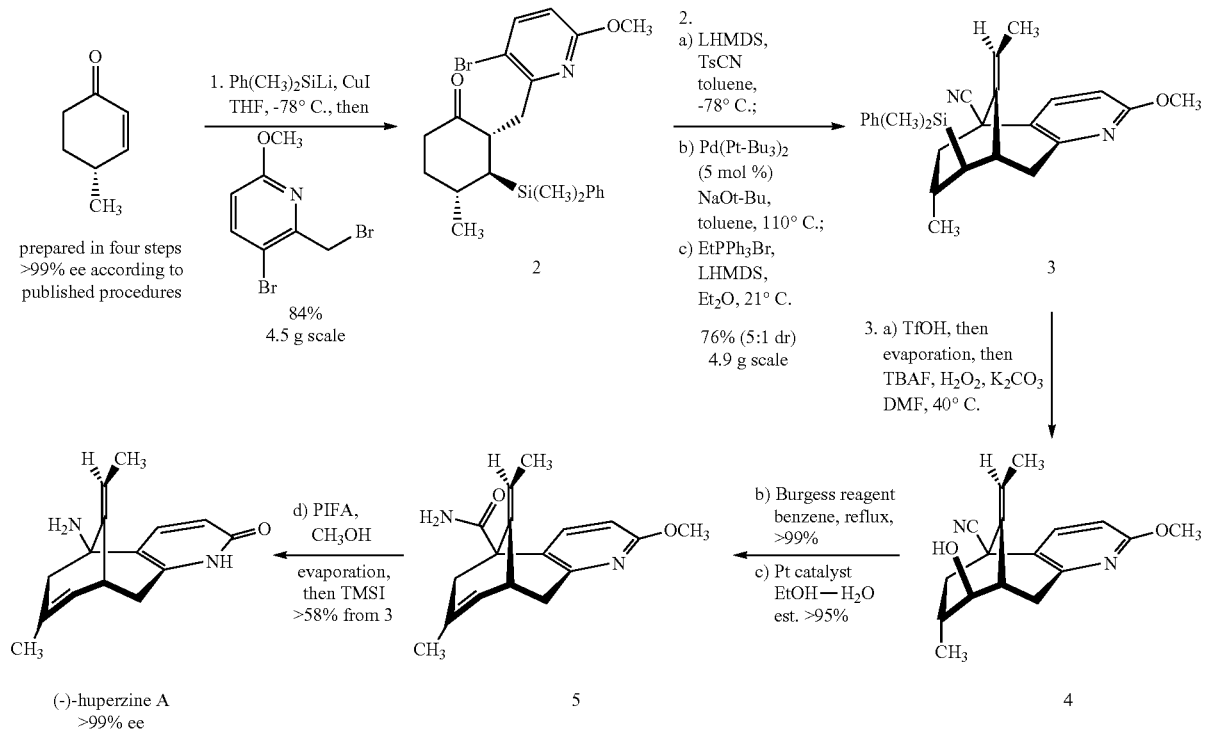

Scheme 1.

Intermediates 3, 4, and 5 may potential be used to access other natural products. Compounds such as 5 in particular may be a useful scaffold for synthesis of other biologically active compounds.

The significant improvement in yield and the notable reduction in process steps achieved by the instant invention is illustrated by a comparison with known processes as summarized below.

Summary of Prior Syntheses

| PI | Stereosel. | Steps | Overall Yield |
|---|---|---|---|
| Kozikowski[1] | Racemic | 12 | 6% |
| Qian[2] | Racemic | 15 | <3.72% (note: yield not reported for the several steps) |
| Kozikowski[3] | Stereosel (chiral aux) | 16 | 2.3% |
| Mann[4] | Racemic | 17 | <2% |
| Mann[4] | Enantiosel (resolution chiral ester) | 16 | <1.4% |
| Fukuyama[5] | Chiral | 23 | 1.8% |

[1]Xia, Y.; Kozikowski, A. P. *J. Am. Chem. Soc.* 1989, 111, 4116.
[2]Qian, L.; Ji, R. *Tetrahedron Lett.* 1989, 30, 2089.
[3]Yamada, F.; Kozikowski, A. P.; Reddy, E. R.; Pang, Y. P.; Miller, J. H.; McKinney, M. *J. Am. Chem. Soc.* 1991, 113, 4695.
[4]Lucey, C.; Kelly, S. A.; Mann, J. *Org. Biomol. Chem.* 2007, 5, 301.
[5]Koshiba, T.; Yokoshima, S.; Fukuyama, T. *Org. Lett.* 2009, 11, 5354.

Further Description of Processes of the Invention

The majority of approaches to huperzine A have relied on introduction of a four-carbon fragment to a bicyclic structure (retrosynthetic cleavage of bonds a and b in 1, as shown below).

Retrosynthetic Analysis of (−)-Huperzine A (1)

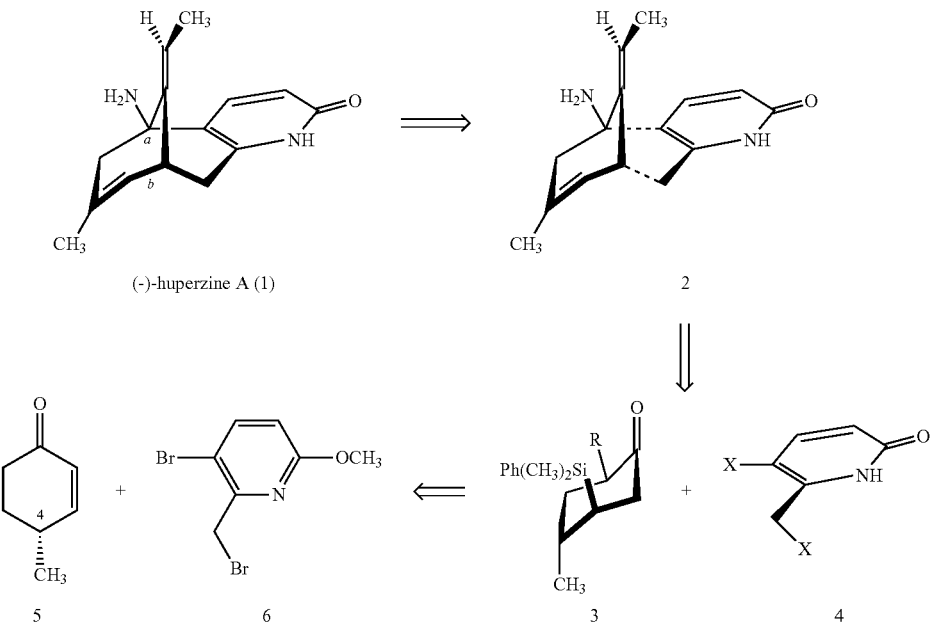

Scheme 2 below provides a further elaboration on the chemical techniques employed in the process of Scheme 1 as described above, and indicates non-isolated intermediates which are generated in various steps of our processes.

Referring to Schemes 1 and 2, we have developed a novel process in which disconnection of two alternative bonds (see 2 in "Retrosynthetic analysis of (−)-huperzine A (1)" above) forms the ketone and pyridone-based synthons 3 and 4, respectively. The former might be obtained from (R)-4-methyl-cyclohex-2-ene-1-one (5) while 3-bromo-2-(bromomethyl)-6-methoxypyridine (6) would serve as a functional equivalent to 4. The C-4 stereocenter in 5 is used in our route to control relative and absolute stereochemistry in the target. Several convenient methods to prepare (R)-4-methylcyclohex-2-ene-1-one (5) have been reported.[16] In preferred embodiments, a straightforward four-step sequence starting from (+)-pulegone can be used.[16a] Dihalopyridines such as 6 have found use in a distinct and significantly more lengthy route to (−)-huperzine A (1), 14c as well as in the synthesis of other *Lycopodium* alkaloids.[17]

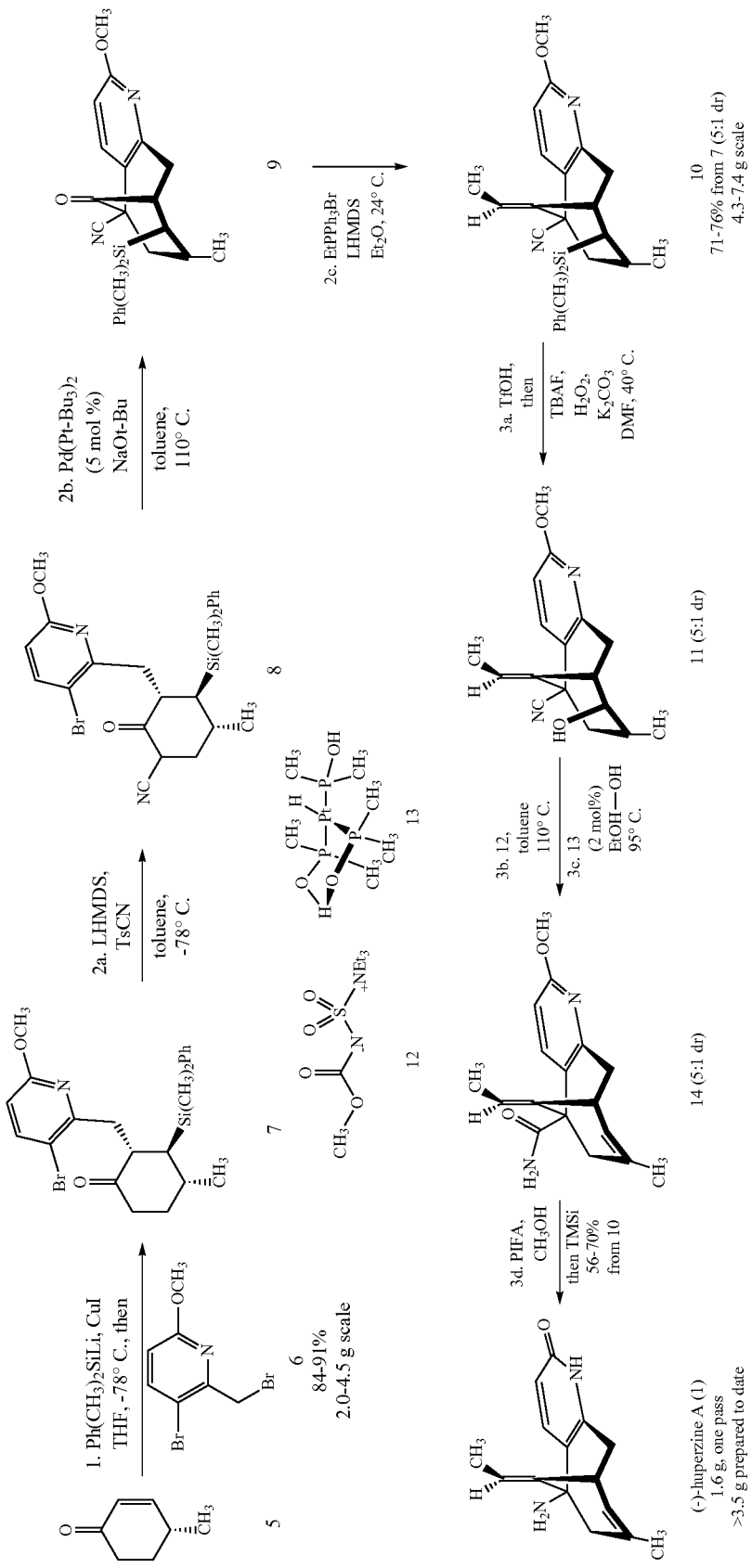

The successful implementation of this strategy is shown in Scheme 2 above. To render the route amenable to large-scale synthesis, we extensively optimized each step, and this allowed many transformations to be efficiently telescoped (the final synthetic route requires three chromatographic purification steps). Our work commenced with conjugate addition of lithium dimethylphenylsilylcuprate to (R)-4-methyl-cyclohex-2-ene-1-one (5). Alkylation of the incipient enolate with 3-bromo-2-(bromomethyl)-6-methoxypyridine (6) afforded the addition-alkylation product 7 as a single detectable diastereomer (1HNMRanalysis), isolated in 84-91% yield after purification (2.0-4.5 g scale).

Kinetically-controlled deprotonation of 7 and trapping of the resulting enolate with para-toluenesulfonyl cyanide,[18] followed by immediate work up of the product mixture, formed the acyanoketone 8 in high purity (est. >95%, $^1$H NMR analysis). Rapid isolation of the product was critical, as the α-cyanoketone 8 underwent disproportionation to starting material (7) and an α, α-dicyanoketone (not shown) if the mixture was allowed to age.

The unpurified α-cyanoketone 8 was then subjected to a palladium-catalyzed intramolecular enolate heteroarylation.[19] Among several catalyst precursors examined, bis(tri-tert-butylphosphine) palladium (0), prepared by the method of Dai and Fu,[20] emerged as the most effective. A dramatic dependence on base was observed (Table 1).

a salt effect and suggests the desired E-isomer is the kinetically-favored product.[21] Under optimized conditions, the olefinated product 10 was isolated in 71-76% yield from 7 as a 5:1 mixture of E/Z isomers by flash-column chromatography (4.3-7.4 g scale). By this approach, the entire carbon skeleton of 1 was formed in high overall yield and in four steps on a multigram scale.

Treatment of the olefination product (10) with trifluoromethanesulfonic acid, followed by oxidative desilylation, provided the cyanoalcohol 11 in high purity ($^1$H NMR analysis). The unpurified cyanoalcohol 11 was efficiently dehydrated by heating with the Burgess reagent (12) in toluene. Thermolysis of the dehydrated product (not shown) in the presence of the platinum catalyst 13[22] in aqueous ethanol afforded the amide 14. Finally, Hofmann rearrangement [bis(trifluoroacetoxy)iodobenzene], global deprotection, and purification by flash-column chromatography afforded separately (−)-huperzine A (1, 56-70% over four operations) and its olefin isomer (not shown, 11-14%). Synthetic (−)-huperzine A (1) was identical in all respects ($^1$H NMR, 13C NMR, IR, three TLC solvent systems, LC/MS retention time, optical rotation) to an authentic sample. Batches of (−)-1 as large as 1.6 g have been prepared.

To date, over 3.5 g of (−)-huperzine A (1) have been prepared by the route delineated above. Our synthesis pro-

TABLE 1

Optimization of the enolate heteroarylation.[a]

| Entry | Base | mol % Pd | Yield 9[b] | Yield 15[c] | Dec.[c] |
|---|---|---|---|---|---|
| 1 | K2CO3 | 10 | <1% | 99% | — |
| 2 | Na2CO3 | 10 | <1% | 99% | — |
| 3 | NaH | 10 | 50% | <1% | 30% |
| 4 | KOt-Bu | 10 | 64% | 10% | 20% |
| 5 | NaOt-Bu | 5 | >99% | <1% | <1% |

[a]All reactions were conducted using Pd(Pt-Bu3)2 as precatalyst in toluene at 110° C. for 3 h.
[b]Isolated yield after purification by flash column chromatography.
[c]Estimated by $^1$H NMR and LC/MS analysis of the unpurified reaction mixture. Dec. = decomposition.

Thus, in the presence of carbonate bases (entries 1, 2), the protodebrominated product 15 predominated. Sodium hydride (entry 3) improved conversion to the cyclized product (9), although extensive decomposition also occurred. Ultimately, we identified sodium tert-butoxide (entry 5) as optimal, and using this base the product was obtained in essentially quantitative yield (1H NMR analysis). The next step of the sequence called for the stereoselective olefination of the ketone function of 9. Treatment of 9 with the lithium ylide derived from ethyltriphenylphosphonium bromide (ether, 24° C.) afforded the olefination product 10 in high yield. A clear trend between E:Z selectivity and concentration was observed (E/Z=1.1, 1.8, 5 at 1.0, 0.1, and 0.01 M, respectively), which is consistent with ceeds in 35-45% overall yield (16-fold more efficient than any other previously reported enantioselective route), and requires only three chromatographic purifications. We envision that this chemistry will provide a reliable supply of synthetic (−)-huperzine A (1) and will greatly facilitate its clinical development for neuroprotective and anti-neurodegenerative applications.

Those of ordinary skill in the art will appreciate that the various reactants, reagents, and reactions used in the processes of the invention may be varied in a number of ways without compromising the efficiency and yield as described herein.

For example, generation of the (−) from huperizine from amide 14 could be achieved by a modified Hoffmann reaction using bis(trifluoroacetoxyiodo)benzene (PIFA) generally in accord with the methods described in Loudon, G. M.; Radhakrishna, A. S.; Almound, M. R.; Blodgett, J. K.; Boutin, R. H. J. Org. Chem., 1984, 49, 4272-4276; Zhang, L.; Kaufmann, G. S.; Pesti, J. A.; Yin, J. J. Org. Chem., 1997, 62, 6918-6920; or Schmuck, C.; Geiger, L. Chem. Comm. 2005, 772-774. Ethanol, propanol, or water can be substituted for methanol in the Hoffman rearrangement of amide 14.

Dehydration of cyanoalcohol 11 using the Burgess reagent can be accomplished in a variety of ways, e.g. by using techniques described in K. C. Nicolaou, D. Y.-K. Chen, X. Huang, T. Ling, M. Bella, S. A. Snyder, "Chemistry and Biology of Diazonamide A: First Total Synthesis and Confirmation of the True Structure" J. Am. Chem. Soc. 126, 12888-12896 (2004).

Conversion of olefination product 10 to cyanoalcohol 11 as described herein can be accomplished in a variety of ways. For example, desilylation can be achieved via reaction with boron trifluoride-acetic acid complex, or a Bronsted acid such as TFA, MSA, FMSA, or tetrafluoroboric acid in an inert solvent, e.g., DCM. When a boron trifluoride-acetic acid complex is used, the olefination product 10 can be oxidized with hydrogen peroxide and $KHCO_3$. When a Bronsted acid is used, the olefination product 10 may be oxidized with hydrogen peroxide, $KHCO_3$, and KF. Methods that may be useful for the transformation of the silyl group to the hydroxy group are also described in Fleming, I. (Chemtracts-Organic Chemistry 1996, 9, 1-64) and Jones, G. R. et al. (Tetrahedron, 1996, 52, 7599-7662).

The Wittig olefination reaction used to convert cyclized product 9 to olefination product 10 could be modified in a variety of ways, e.g. through use of bases such as n-butyllithium, sodium bis(trimethylsilyl)amide, lithium bis(trimethylsilyl)amide, potassium bis(trimethylsilyl)amide or lithium diisopropylamide in solvents such as THF, diethylether or 1,4-dioxane. See Chem. Rev. 1989, 89, 863; Modern Carbonyl Olefination 2004, 1-17; Liebigs Ann. Chem. 1997, 1283.

In the cyanation of the enolate generated by deprotonation of addition-alkylation product 7, THF can be substituted for toluene in the cyanation reaction. See D. Kahne and D. B. Collum, Tetrahedron Lett., 5011 (1981), and lithium bis(trimethylsilyl) amide (LHMDS) can be substituted for lithium diisopropyl amide (LDA).

Any of the methods described in the references of note 16 can be used to prepare the starting material (R)-4-methylcyclohex-2-ene-1-one 1.

Further details regarding the above-described processes are presented below in the illustrative experimental section.

Experimental Section

General Experimental Procedures

All reactions were performed in single-neck, flame-dried, round-bottomed flasks fitted with rubber septa under a positive pressure of argon, unless otherwise noted. Air and moisture-sensitive liquids were transferred via syringe or stainless steel cannula, or were handled in a nitrogen-filled drybox (working oxygen level <1 ppm). Organic solutions were concentrated by rotary evaporation at 30-33° C. Flash-column chromatography was performed as described by Still et al,[1] employing silica gel (60 Å, 40-63 μm particle size) purchased from Sorbent Technologies (Atlanta, Ga.). Analytical thin-layered chromatography (TLC) was performed using glass-plates pre-coated with silica gel (1.0 mm, 60 Å pore size) impregnated with a fluorescent indicator (254 nm). TLC plates were visualized by exposure to ultraviolet light (UV) or/and submersion in aqueous potassium permagnate solution ($KMnO_4$), followed by brief heating on a hot plate (120° C., 10-15 s).

Materials.

Commercial solvents and reagents were used as received with the following exceptions. Benzene, dichloromethane, ether, and toluene were purified according to the method of Pangborn et al.[2] Tetrahydrofuran was distilled from sodium/benzophenone under an atmosphere of nitrogen immediately before use. Methanol was distilled from magnesium methoxide under an atmosphere of nitrogen immediately before use. Hexamethylphosphoramide was distilled from calcium hydride and stored under nitrogen. 4-Å Molecular sieves were activated by heating overnight in vacuo (200° C., 200 mTorr), stored in a gravity oven (120° C.), and were flame-dried in vacuo (100 mTorr) immediately before use. Solutions of phenyldimethylsilyllithium in tetrahydrofuran were prepared according to the procedure of Fleming and co-workers.[3] (R)-4-Methyl-cyclohexe-2-ene-1-one (5) was prepared from (+)-pulegone according to the procedure of Lee and co-workers.[4] 3-Bromo-2-(bromomethyl)-6-methoxypyridine (6) was prepared according to the procedure of Kelly and co-workers.[5] Bis(tri-tert-butylphosphine) palladium (0) was prepared according to the procedure of Dai and Fu.[6] Methyl N-(triethylammoniumsulfonyl)carbamate (Burgess reagent, 12) was prepared according to the procedure of Burgess and co-workers.[7] Hydrido(hydroxydimethylphosphino) [hydrogen bis(hydroxydimethylphosphino)]platinum (II) (13) was prepared according to the procedure of Ghaffar and Parkins.[8] Ethyltriphenylphosphonium bromide was recrystallized from water, and the resulting crystals were dried for 24 h at 50° C. in vacuo.

Instrumentation.

Proton nuclear magnetic resonance spectra ($^1H$ NMR) were recorded at 400 or 500 MHz at 24° C., unless otherwise noted. Chemical shifts are expressed in parts per million (ppm, δ scale) downfield from tetramethylsilane and are referenced to residual protium in the NMR solvent ($CHCl_3$, δ 7.26). Data are represented as follows: chemical shift, multiplicity (s=singlet, d=doublet, t=triplet, q=quartet, m=multiplet and/or multiple resonances, br=broad, app=apparent), integration, coupling constant in Hertz, and assignment. Proton-decoupled carbon nuclear magnetic resonance spectra ($^{13}C$ NMR) were recorded at 100 or 125 MHz at 24° C., unless otherwise noted. Chemical shifts are expressed in parts per million (ppm, δ scale) downfield from tetramethylsilane and are referenced to the carbon resonances of the solvent ($CDCl_3$, δ 77.0). Distortionless enhancement by polarization transfer spectra [DEPT (135)] were recorded at 100 or 125 MHz at 24° C., unless otherwise noted. $^{13}C$ NMR and DEPT (135) data are combined and represented as follows: chemical shift, carbon type [obtained from DEPT (135) experiments]. Attenuated total reflectance Fourier transform infrared spectra (ATR-FTIR) were obtained using a Thermo Electron Corporation Nicolet 6700 FTIR spectrometer referenced to a polystyrene standard. Data are represented as follows: frequency of absorption ($cm^{-1}$), intensity of absorption (s=strong, m=medium, w=weak, br=broad). High-resolution mass spectrometry (HRMS) data were obtained using a Waters UPLC/HRMS instrument equipped with a dual API/ESI high-resolution mass spectrometry detector and photodiode array detector. Unless otherwise noted, samples were eluted over a reverse-phase $C_{18}$ column (1.7 m particle size, 2.1×50 mm) with a linear gradient of 5% acetonitrile-water containing 0.1% formic acid→95% acetonitrile-water containing 0.1% formic acid over 4 min, followed by 100% acetonitrile containing 0.1% formic acid for 1 min, at a flow rate of 600 μL/min. Optical rotations were measured on a Perkin Elmer polarimeter equipped with a sodium (589 nm, D) lamp. Optical rotation data are represented as follows: specific rotation ($[\alpha]^{20}_n$), concentration (g/mL), and solvent.

Synthetic Procedures.[9]

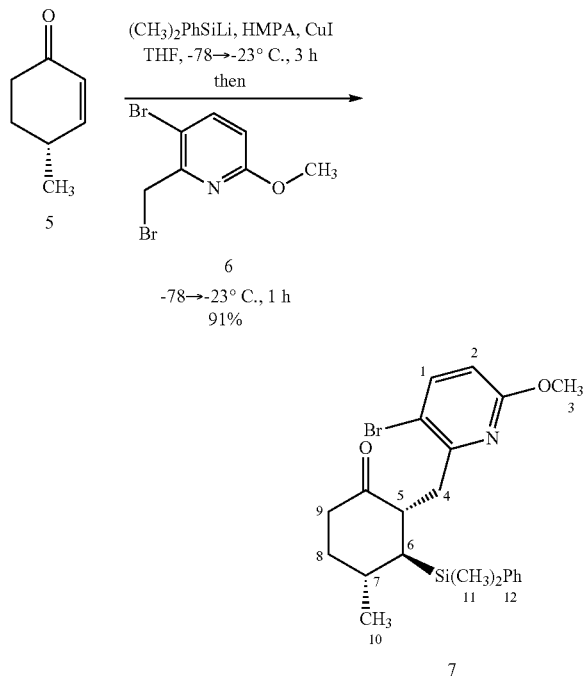

Step 1: Addition-Alkylation of (R)-4-Methyl-cyclohexe-2-ene-1-one (5) (Addition-Alkylation Product 7)

Hexamethylphosphoramide (11.4 mL, 65.4 mmol, 3.60 equiv) was added dropwise via syringe to a stirred suspension of cuprous iodide (3.46 g, 18.2 mmol, 1.00 equiv) in tetrahydrofuran (36 mL) at 24° C. The resulting mixture was cooled to −78° C. A solution of dimethylphenylsilyllithium in tetrahydrofuran (0.46 M, 79.0 mL, 36.3 mmol, 2.00 equiv) was added dropwise via syringe pump over 30 min to the cold brown suspension. Upon completion of the addition, the mixture was warmed to 0° C. The resulting solution was stirred for 1 h at 0° C. The mixture was then cooled to −78° C. (R)-4-Methyl-cyclohexe-2-ene-1-one (5, 2.00 g, 18.2 mmol, 1.00 equiv) was added dropwise via syringe over 5 min. Upon completion of the addition, the reaction mixture was warmed to −23° C. The warmed solution was stirred for 3 h at −23° C. The reaction mixture was then cooled to −78° C. A solution of 3-bromo-2-(bromomethyl)-6-methoxypyridine (6) in tetrahydrofuran (0.50 M, 40.0 mL, 20.0 mmol, 1.10 equiv) was added dropwise via cannula over 30 min to the cold reaction mixture. Upon completion of the addition, the reaction mixture was warmed to −23° C. The warmed solution was stirred for 1 h at −23° C. The product mixture was then warmed over 30 min to 24° C. The warmed product mixture was eluted through a pad of celite (length/diameter=3/9 cm). The celite pad was washed sequentially with saturated aqueous sodium bicarbonate solution (100 mL), ethyl acetate (250 mL), saturated aqueous sodium bicarbonate solution (100 mL), and ethyl acetate (250 mL). The biphasic filtrate was collected and transferred to a separatory funnel. The layers that formed were separated. The organic layer was washed sequentially with saturated aqueous sodium bicarbonate solution (2×200 mL), distilled water (200 mL), and saturated aqueous sodium chloride solution (200 mL). The washed organic layer was dried over sodium sulfate. The dried solution was filtered and the filtrate was concentrated. The residue obtained was purified by flash-column chromatography (eluting with 5% ethyl acetate-hexanes) to afford the addition-alkylation product 7 as a pale-yellow, viscous oil (7.37 g, 91%).

$R_f$=0.27 (5% ethyl acetate-hexanes, KMnO$_4$). $[\alpha]^{20}_n$=−40.8 (c 0.10, CHCl$_3$). $^1$H NMR (500 MHz, CDCl$_3$), δ 7.55 (d, 1H, J=8.5 Hz, H$_1$), 7.45 (dd, 2H, J=8.0, 2.0 Hz, H$_{12}$), 7.33-7.29 (m, 3H, H$_{12}$), 6.42 (d, 1H, J=8.5 Hz, H$_2$), 3.79 (s; 3H, H$_3$), 3.22-3.12 (m, 2H, H$_4$/H$_5$), 2.84 (dd, 1H, J=14.5, 4.5 Hz, H$_4$), 2.58-2.52 (m, 1H, H$_9$), 2.23-2.17 (m, 1H, H$_9$), 2.05-1.94 (m, 2H, H$_7$/H$_8$), 1.82-1.75 (m, 1H, H$_8$), 1.15 (t, 1H, J=6.5 Hz, H$_6$), 1.00 (d, 3H, 6.5 Hz, H$_{10}$), 0.32 (app s, 6H, H$_{11}$). $^{13}$C NMR (125 MHz, CDCl$_3$), δ 214.8 (C), 162.2 (C), 154.7 (C), 142.4 (CH), 138.1 (C), 134.0 (CH), 129.3 (CH), 128.0 (CH), 112.2 (C), 110.1 (CH), 53.6 (CH$_3$), 47.1 (CH), 40.3 (CH$_2$), 37.3 (CH$_2$), 34.3 (CH), 31.1 (CH$_2$), 29.3 (CH), 23.9 (CH$_3$), −3.0 (CH$_3$), −3.6 (CH$_3$). IR (ATR-FTIR), cm$^{-1}$: 2951 (br), 1709 (s), 1575 (s), 1459 (s), 1417 (s), 1295 (m), 1250 (m), 1111 (m), 1037 (m), 1014 (m), 820 (s), 734 (m), 701 (m). HRMS-CI(m/z): [M+H]$^+$ calcd for C$_{22}$H$_{29}$BrNO$_2$Si, 446.1146/448.1125; found, 446.1147/448.1124.

Steps 2a-c: Synthesis of the Olefination Product 10

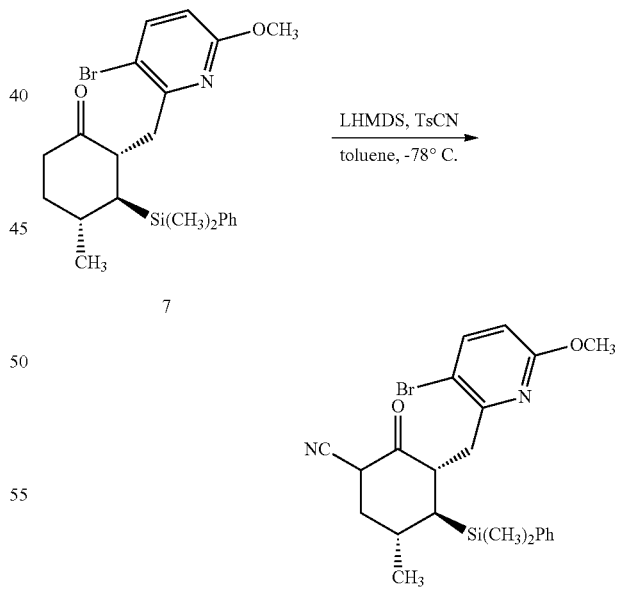

Step 2a: Cyanation of the Addition-Alkylation Product 7 (α-Cyanoketone 8)

A solution of lithium hexamethyldisilazide in toluene (1.00 M, 49.7 mL, 49.7 mmol, 3.00 equiv) was added dropwise over 15 min via syringe pump to a stirred solution of the addition-alkylation product 7 (7.37 g, 16.6 mmol, 1.00 equiv) in toluene (170 mL) at −78° C. Upon completion of the addition, the reaction mixture was warmed to 0° C. The warmed solution was stirred for 15 min at 0° C. The mixture was then cooled to −78° C. A solution of p-toluenesulfonyl cyanide in toluene (1.00 M, 18.2 mL, 18.2 mmol, 1.10 equiv) was added quickly (<1 min) via syringe to the cold reaction mixture. The reaction mixture was stirred for 1 min at −78° C. The cold product mixture was rapidly diluted with 100 mM aqueous sodium phosphate buffer solution (pH 7, 30 mL). The product mixture was allowed to warm over 30 min to 24° C., with stirring. The warmed product mixture was diluted with ethyl acetate (200 mL). The diluted product mixture was transferred to a separatory funnel that had been charged with 100 mM aqueous sodium phosphate buffer solution (pH 7, 150 mL). The layers that formed were separated. The aqueous layer was extracted with ethyl acetate (3×150 mL). The organic layers were combined, and the combined organic layers were dried over sodium sulfate. The dried solution was filtered and the filtrate was concentrated to afford the unpurified α-cyanoketone 8 as a pale-yellow, viscous oil. $^1$H NMR analysis (400 MHz, CDCl$_3$) indicated >95% conversion to the cyanoketone 8 (mixture of (R)-α-cyanoketone, (S)-a-cyanoketone, and β-hydroxy-a,3-unsaturated nitrile isomers). The product so obtained was used directly in the following step.

The α-cyanoketone 8 was found to be unstable towards purification by flash-column chromatography. Therefore, further characterization was not attempted.

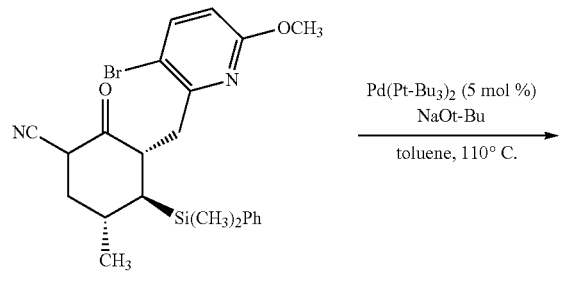

Step 2b: Cyclization of the α-Cyanoketone 8 (Tricycle 9)

A 500-mL round-bottomed flask fused to a Teflon-coated valve was charged with the unpurified α-cyanoketone 8 (16.6 mmol, 1.00 equiv, assuming quantitative yield in the preceding step). The residue was dried by azeotropic distillation with benzene (5.0 mL). The vessel was sealed and the sealed vessel was transferred to a nitrogen-filled drybox. Sodium tert-butoxide (1.75 g, 18.2 mmol, 1.10 equiv), bis(tri-tert-butylphosphine)palladium (0) (423 mg, 828 μmol, 0.05 equiv) and toluene (170 mL) were added sequentially to the flask. The vessel was sealed, and the sealed vessel was removed from the drybox. The reaction vessel was placed in an oil bath that had been preheated to 110° C. The reaction mixture was stirred and heated for 12 h at 110° C. The reaction vessel was removed from the oil bath and the product mixture was allowed to cool over 30 min to 24° C. The cooled product mixture was diluted with dichloromethane (300 mL). The diluted mixture was transferred to a separatory funnel that had been charged with saturated aqueous sodium bicarbonate solution (400 mL). The layers that formed were separated. The aqueous layer was extracted with dichloromethane (3×500 mL). The organic layers were combined, and the combined organic layers were dried over sodium sulfate. The dried solution was filtered and the filtrate was concentrated to afford the unpurified cyclized product 9 as a pale-yellow, viscous oil. $^1$H NMR analysis (400 MHz, CDCl$_3$) indicated >95% conversion to the cyclized product 9. The product so obtained was used directly in the following step. An analytically pure sample of the cyclized product 9 was obtained by flash-column chromatography (eluting with 5% ethyl acetate-hexanes):

R$_f$=0.23 (5% ethyl acetate-hexanes, KMnO$_4$). $^1$H NMR (500 MHz, CDCl$_3$), δ 7.64 (d, 1H, J=9.0 Hz, H$_1$), 7.51 (dd, 2H, J=7.0, 1.5 Hz, H$_{11}$), 7.39-7.29 (m, 3H, H$_{11}$), 6.74 (d, 1H, J=8.5 Hz, H$_2$), 3.91 (s, 3H, H$_3$), 3.14 (dd, 1H, J=18.0, 4.5 Hz, H$_4$), 2.95-2.92 (m, 1H, H$_5$), 2.82-2.77 (m, 2H, H$_4$/H$_8$), 2.15 (dd, 1H, J=13.5, 10.0 Hz, H$_8$), 1.85-1.78 (m, 1H, H$_7$), 1.32 (dd, 1H, J=10.0, 6.5 Hz, H$_6$), 0.75 (d, 3H, J=6.5 Hz, H$_9$), 0.40 (s, 3H, H$_{10}$), 0.37 (s, 3H, H$_{10}$). 13C NMR (125 MHz, CDCl$_3$), δ 206.0 (C), 164.1 (C), 149.5 (C), 138.5 (CH), 136.9 (C), 134.1 (CH), 129.8 (CH), 128.3 (CH), 125.1 (C), 119.2 (C), 111.0 (CH), 53.9 (CH$_3$), 52.4 (CH$_2$), 49.9 (C), 44.9 (CH), 42.4 (CH$_2$), 38.1 (CH), 28.2 (CH), 21.8 (CH$_3$), −3.4 (CH$_3$), −3.8 (CH$_3$). IR (ATR-FTIR), cm$^{-1}$: 2955 (br), 2268 (w), 1736 (s), 1713 (w), 1599 (m), 1576 (w), 1476 (s), 1424 (m), 1321 (m), 1264 (m), 1130 (m), 1112 (m), 1028 (m), 824 (s), 737 (w), 704 (m). HRMS-CI(m/z): [M+H]$^+$ calcd for C$_{23}$H$_{27}$N$_2$O$_2$Si, 391.1837; found, 391.1839.

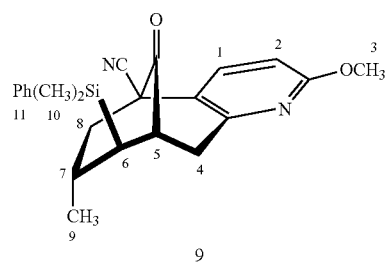

9

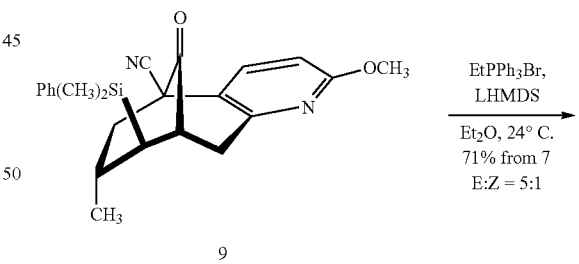

9

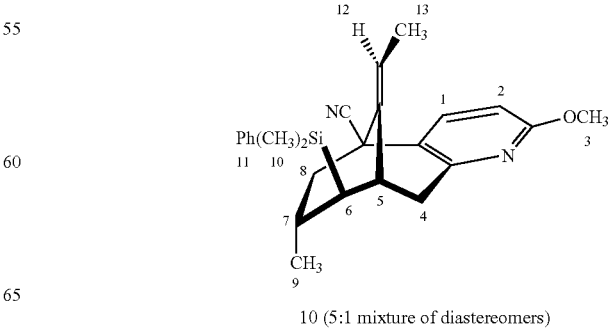

10 (5:1 mixture of diastereomers)

Step 2c: Olefination of the Cyclized Product 9 (Alkene 10)

In a nitrogen-filled drybox, a 500-mL round-bottomed flask was charged sequentially with ethyltriphenylphosphonium bromide (7.38 g, 19.9 mmol, 1.20 equiv) and lithium hexamethyldisilazide (3.33 g, 19.9 mmol, 1.20 equiv). The flask was sealed with a rubber septum, and the sealed flask was removed from the drybox. Ether (200 mL) was added to the flask via syringe. The resulting orange suspension was stirred for 1 h at 24° C. During this time, the solids dissolved to form a clear orange solution. In a separate flask, a solution of the unpurified cyclized product 9 (16.6 mmol, 1.00 equiv, assuming quantitative yield in the preceeding step) in ether (1.5 L) was prepared. The orange ylide solution was transferred via cannula over 10 min to the flask containing the cyclized product 9 at 24° C. The reaction mixture was stirred for 12 h at 24° C. The product mixture was poured into a separatory funnel that had been charged with distilled water (500 mL) and ethyl acetate (500 mL). The layers that formed were separated. The aqueous layer was extracted with ethyl acetate (2×500 mL). The organic layers were combined and the combined organic layers were dried over sodium sulfate. The dried solution was filtered and the filtrate was concentrated. The residue obtained was purified by flash-column chromatography (eluting with 5% ethyl acetate-hexanes) to yield the olefination product 10 as a pale-yellow, viscous oil (4.74 g, 71% from 7, 5:1 mixture of E:Z diastereomers).

Figure 3:
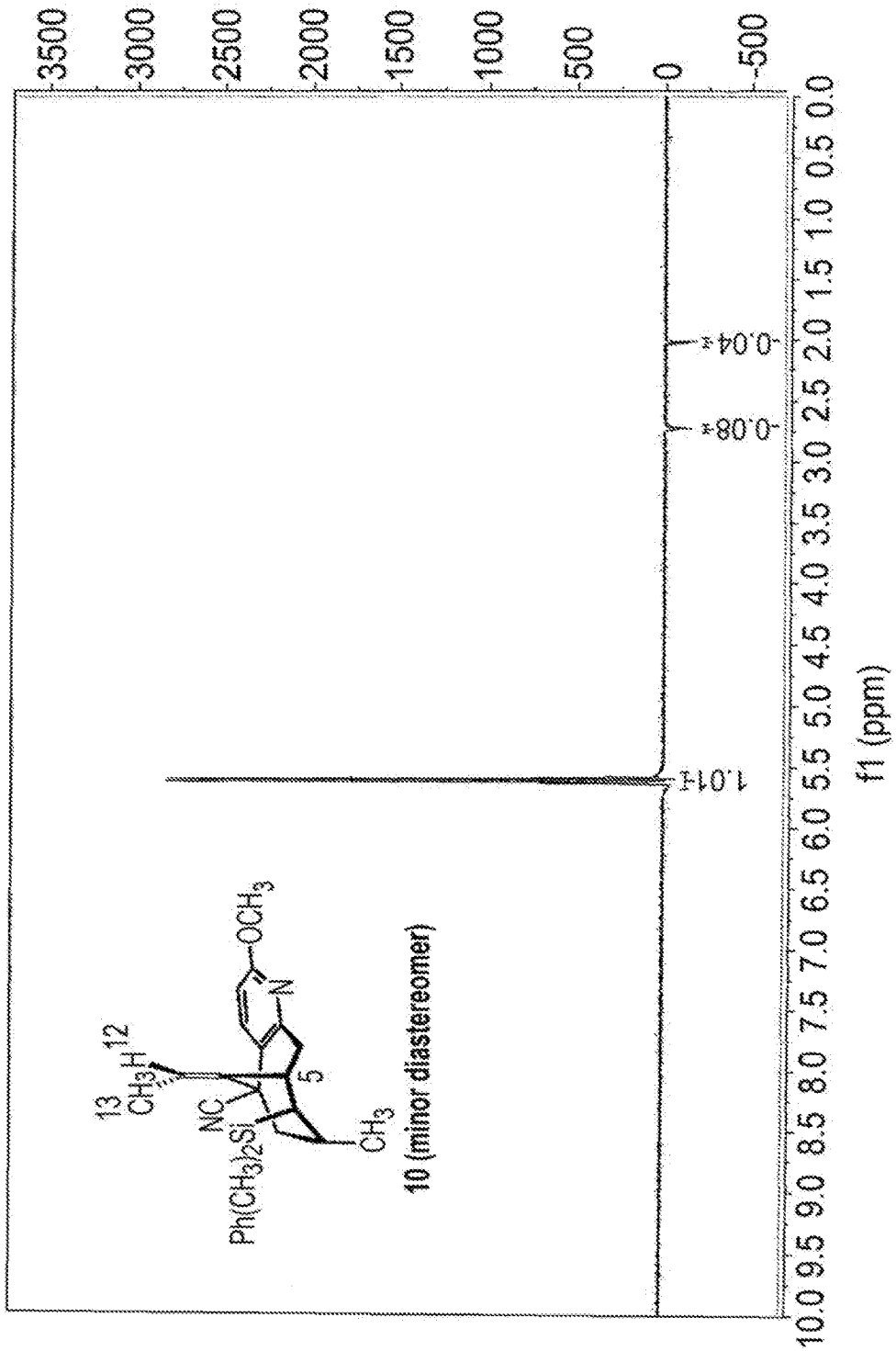
FIG. 3 illustrates that the minor diastereomer of an olefination product made in accordance with a process of the invention was shown to be of the Z-configuration by NOE analysis (500 MHz, CDCl3).

$R_f$=0.20 (5% ethyl acetate-hexanes, KMnO$_4$). $^1$H NMR (400 MHz, CDCl$_3$, 5:1 mixture of diastereomers): E-olefin (major diastereomer), δ 7.69 (d, 1H, J=8.4 Hz, H$_1$), 7.54-7.48 (m, 2H, H$_{11}$), 7.39-7.34 (m, 3H, H$_{11}$), 6.64 (d, 1H, J=8.8 Hz, H$_2$), 5.95 (q, 1H, J=6.8 Hz, H$_{12}$), 3.90 (s, 3H, H$_3$), 3.37-3.34 (m, 1H, H$_5$), 2.86 (dd, 1H, J=17.6, 4.8 Hz, H$_4$), 2.60-2.55 (m, 1H, H$_4$), 2.50 (dd, 1H, J=12.4, 6.0 Hz, H$_8$), 1.79-1.68 (m, 2H, H$_7$/H$_8$), 1.72 (d, 3H, J=6.8 Hz, H$_{13}$), 0.77 (dd, 1H, J=8.8, 5.6 Hz, H$_6$), 0.63 (d, 3H, J=6.8 Hz, H$_9$), 0.37 (s, 3H, H$_{10}$), 0.36 (s, 3H, H$_{10}$); Z-olefin (minor diastereomer), δ 7.78 (d, 1H, J=8.8 Hz, H$_1$), 7.54-7.48 (m, 2H, H$_{11}$), 7.39-7.34 (m, 3H, H$_{11}$), 6.67 (d, 1H, J=8.8 Hz, H$_2$), 5.60 (q, 1H, J=7.6 Hz, H$_{12}$), 3.91 (s, 3H, H$_3$), 2.94 (dd, 1H, J=17.6, 4.8 Hz, H$_4$), 2.75-2.70 (m, 1H, H$_5$), 2.62-2.46 (m, 2H, H$_4$/H$_8$), 2.02 (d, 3H, J=8 Hz, H$_{13}$), 1.79-1.68 (m, 2H, H$_7$/H$_8$), 0.67-0.60 (m, 1H, H$_6$), 0.62 (d, 3H, J=6 Hz, H$_9$), 0.36 (s, 3H, H$_{10}$), 0.33 (s, 3H, H$_{10}$). $^{13}$C NMR (100 MHz, CDCl$_3$, 5:1 mixture of diastereomers): E-olefin (major diastereomer), δ 163.3 (C), 151.9 (C), 138.3 (C), 137.9 (CH), 134.2 (C), 134.0 (CH), 129.4 (CH), 128.1 (CH), 127.4 (C), 122.7 (C), 118.2 (CH), 109.5 (CH), 53.7 (CH$_3$), 50.4 (CH$_2$), 44.4 (C), 42.2 (CH$_2$), 34.7 (CH), 30.7 (C), 27.7 (CH), 22.3 (CH$_3$), 12.7 (CH$_3$), -2.9 (CH$_3$), -3.3 (CH$_3$); Z-olefin (minor diastereomer), δ 163.3 (C), 152.3 (C), 138.4 (C), 138.0 (CH), 134.0 (CH), 132.7 (C), 129.3 (CH), 128.0 (CH), 127.2 (C), 124.6 (C), 120.6 (CH), 109.6 (CH), 53.8 (CH$_3$), 51.1 (CH$_2$), 43.3 (CH$_2$), 41.9 (CH), 39.7 (C), 34.7 (CH), 27.9 (CH), 22.0 (CH$_3$), 12.8 (CH$_3$), -3.0 (CH$_3$), -3.5 (CH$_3$). IR (ATR-FTIR), cm$^{-1}$: 2952 (br), 1598 (m), 1578 (w), 1476 (s), 1426 (m), 1320 (m), 1264 (m), 1112 (w), 1031 (w), 824 (m), 733 (w), 702 (w). HRMS-CI(m/z): [M+H]$^+$ calcd for C$_{25}$H$_{31}$N$_2$OSi, 403.2201; found, 403.2198. The minor diastereomer was shown to be of the Z-configuration by NOE analysis (500 MHz, CDCl$_3$). See FIG. 3.

Steps 3a-d: Conversion of the Olefination Product 10 to (−)-Huperzine A (1)

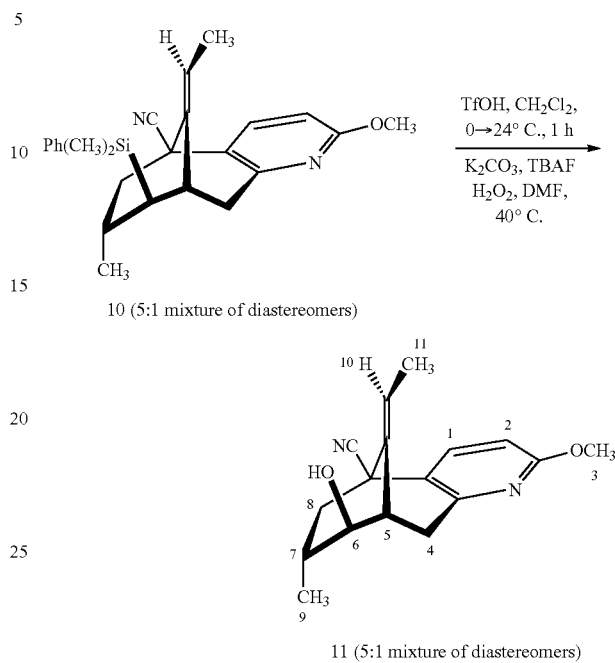

10 (5:1 mixture of diastereomers)

11 (5:1 mixture of diastereomers)

Step 3a: Tamao-Fleming Oxidation of the Olefination Product 10 (Alcohol 11)

Trifluoromethanesulfonic acid (2.29 mL, 26.0 mmol, 2.20 equiv) was added dropwise via syringe over 5 min to a stirred solution of the olefination product 10 (4.74 g, 11.8 mmol, 1.00 equiv) in dichloromethane (59 mL) at 0° C. The reaction mixture was allowed to warm over 10 min to 24° C. The reaction mixture was stirred for 1 h at 24° C. The solvent was evaporated under reduced pressure. The residue obtained was dissolved in N,N-dimethylformamide (94 mL). Potassium carbonate (4.89 g, 35.4 mmol, 3.00 equiv) and distilled water (47 mL) were then added in sequence. The resulting milky solution was stirred for 15 min at 24° C. A solution of tetrabutylammonium fluoride in tetrahydrofuran (1.0 M, 177 mL, 177 mmol, 15.0 equiv) was added, and the resulting mixture was stirred for 1 h at 24° C. A solution of hydrogen peroxide in water (35%, 30.4 mL, 354 mmol, 30.0 equiv) was then added rapidly and the resulting mixture was warmed to 40° C. The reaction mixture was stirred and heated for 12 h at 40° C. The product mixture was cooled over 10 min to 24° C. The cooled product mixture was transferred to a separatory funnel that had been charged with distilled water (300 mL) and 50% ethyl acetate-hexanes (v/v, 500 mL). The layers that formed were separated. The organic layer was washed sequentially with water (5×300 mL) and saturated aqueous sodium chloride solution (2×300 mL). The washed organic layer was dried over sodium sulfate. The dried solution was filtered and the filtrate was concentrated to afford the unpurified alcohol 11 as a pale-yellow solid (3.35 g). $^1$H NMR analysis (400 MHz, CDCl$_3$) indicated >95% conversion to the alcohol 11. The product so obtained was used directly in the following step.

An analytically pure sample of the alcohol 11 was obtained by flash-column chromatography (eluting with 50% ethyl acetate-hexanes):

$R_f$=0.30 (50% ethyl acetate-hexanes, KMnO$_4$). $^1$H NMR (500 MHz, CDCl$_3$, 5:1 mixture of diastereomers): E-olefin (major diastereomer), δ 7.69 (d, 1H, J=8.5 Hz, H$_1$), 6.64 (d, 1H, J=8.5 Hz, H$_2$), 6.12 (q, 1H, J=6.5 Hz, H$_{10}$), 3.89 (s, 3H, H$_3$), 3.54 (dd, 1H, J=6.0, 3.5 Hz, H$_6$), 3.29-3.27 (m, 1H, H$_5$), 3.10 (dd, 1H, J=18.5, 6.5 Hz, H$_4$), 2.99 (d, 1H, J=17.5 Hz, H$_4$), 2.59 (dd, 1H, J=13.5, 7.0 Hz, H$_8$), 1.79 (d, 3H, J=7.0 Hz, H$_{11}$), 1.87-1.76 (m, 2H, H$_7$/H$_8$), 0.71 (d, 3H, J=7.5 Hz, H$_9$); Z-olefin (minor diastereomer), δ 7.78 (d, 1H, J=8.5 Hz, H$_1$), 6.67 (d, 1H, J=8.5 Hz, H$_2$), 5.65 (q, 1H, J=7.5 Hz, H$_{10}$), 3.90 (s, 3H, H$_3$), 3.43 (dd, 1H, J=5.5, 3.5 Hz, H$_6$), 3.17 (dd, 1H, J=18.0, 7.0 Hz, H$_4$), 2.94 (d, 1H, J=18.0 Hz, H$_4$), 2.70 (dd, 1H, J=13.5, 7.5 Hz, H$_8$), 2.62-2.60 (m, 1H, H$_5$), 2.07 (d, 3H, J=7.0 Hz, H$_{11}$), 1.87-1.76 (m, 2H, H$_7$/H$_8$), 0.68 (d, 3H, J=7.5 Hz, H$_9$). $^{13}$C NMR (125 MHz, CDCl$_3$, 5:1 mixture of diastereomers): E-olefin (major diastereomer), δ 163.5 (C), 152.3 (C), 137.7 (CH), 131.5 (C), 126.4 (C), 122.0 (C), 120.4 (CH), 109.7 (CH), 78.4 (CH), 53.8 (CH$_3$), 44.7 (CH$_2$), 44.5 (C), 39.1 (CH), 37.9 (CH$_2$), 34.2 (CH), 17.9 (CH$_3$), 12.8 (CH$_3$); Z-olefin (minor diastereomer), δ 163.5 (C), 152.6 (C), 137.5 (CH), 129.8 (C), 126.0 (C), 122.8 (CH), 122.0 (C), 109.7 (CH), 77.9 (CH), 53.8 (CH$_3$), 49.3 (CH), 45.5 (CH$_2$), 44.5 (C), 37.9 (CH$_2$), 34.2 (CH), 17.9 (CH$_3$), 12.8 (CH$_3$). IR (ATR-FTIR), cm$^{-1}$: 3431 (br), 2925 (br), 1598 (m), 1577 (w), 1476 (s), 1422 (m), 1323 (m), 1267 (m), 1033 (m), 828 (w), 658 (w). HRMS-CI(m/z): [M+H]+ calcd for C$_{17}$H$_{21}$N$_2$O$_2$, 285.1598; found, 285.1597.

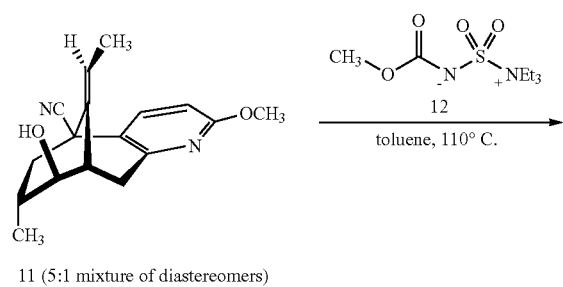

11 (5:1 mixture of diastereomers)

Step 3b: Dehydration of the Tamao-Fleming Oxidation Product 11 (Alkene 16)

A 100-mL round-bottomed flask fused to a Teflon-coated valve was charged sequentially with the unpurified Tamao-Fleming oxidation product 11 (11.8 mmol, 1.00 equiv, assuming quantitative yield in the preceeding step) and methyl N-(triethylammoniumsulfonyl)carbamate 12 (3.09 g, 13.0 mmol, 1.10 equiv). Benzene (10 mL) was added and the resulting solution was stirred for 15 min at 24° C. The solution was concentrated to dryness and the residue obtained was redissolved in toluene (59 mL). The reaction vessel was sealed and the sealed vessel was placed in an oil bath that had been preheated to 110° C. The reaction mixture was stirred and heated for 12 h at 110° C. The product mixture was cooled over 30 min to 24° C. The cooled product mixture was diluted with ethyl acetate (200 mL) and the diluted solution was transferred to a separatory funnel that had been charged with saturated aqueous sodium bicarbonate solution (200 mL). The layers that formed were separated. The aqueous layer was extracted with ethyl acetate (200 mL). The organic layers were combined and the combined organic layers were dried over sodium sulfate. The dried solution was filtered and the filtrate was concentrated to afford the alkene 16 as an off-white solid (3.19 g). $^1$H NMR analysis (400 MHz, CDCl$_3$) indicated >95% conversion to the alkene 16. The product so obtained was used directly in the following step. An analytically pure sample of the alkene 16 was obtained by flash-column chromatography (eluting with 10% ethyl acetate-hexanes):

$R_f$=0.32 (10% ethyl acetate-hexanes, KMnO$_4$). $^1$H NMR (400 MHz, CDCl$_3$, 5:1 mixture of diastereomers): E-olefin (major diastereomer), δ 7.70 (d, 1H, J=8.8 Hz, H$_1$), 6.63 (d, 1H, J=8.8 Hz, H$_2$), 5.95 (q, 1H, J=6.8 Hz, H$_9$), 5.48 (m, 1H, H$_6$), 3.89 (s, 3H, H$_3$), 3.62 (m, 1H, H$_5$), 2.98 (dd, 1H, J=17.2, 5.2 Hz, H$_4$), 2.88-2.80 (m, 2H, H$_4$/H$_7$), 2.38 (d, 1H, J=16.8 Hz, H$_7$), 1.76 (d, 3H, J=6.8 Hz, H$_{10}$), 1.55 (s, 3H, H$_8$); Z-olefin (minor diastereomer), δ 7.78 (d, 1H, J=8.4 Hz, H$_1$), 6.66 (d, 1H, J=8.4 Hz, H$_2$), 5.65 (q, 1H, J=7.2 Hz, H$_9$), 5.46 (d, 1H, J=4.8 Hz, H$_6$), 3.89 (s, 3H, H$_3$), 3.10-2.77 (m, 4H, 2×H$_4$/H$_5$/H$_7$), 2.38 (d, 1H, J=16.8 Hz, H$_7$), 2.06 (d, 3H, J=7.6 Hz, H$_{10}$), 1.54 (s, 3H, H$_8$). $^{13}$C NMR (100 MHz, CDCl$_3$, 5:1 mixture of diastereomer): E-olefin (major diastereomer), δ 163.5 (C), 152.9 (C), 137.7 (CH), 132.3 (C), 130.7 (C), 125.2 (CH), 124.8 (C), 121.7 (C), 116.7 (CH), 109.2 (CH), 53.7 (CH$_3$), 47.5 (CH$_2$), 44.6 (C), 39.8 (CH$_2$), 31.6 (CH), 22.6 (CH$_3$), 12.7 (CH$_3$); Z-olefin (minor diastereomer), δ 163.5 (C), 153.2 (C), 137.7 (CH), 130.9 (C), 130.2 (C), 126.3 (CH), 124.6 (C), 121.7 (C), 119.0 (CH), 109.3 (CH), 53.7 (CH$_3$), 48.3 (CH$_2$), 42.1 (CH), 40.7 (CH$_2$), 40.1 (C), 22.5 (CH$_3$), 12.3 (CH$_3$). IR (ATR-FTIR), cm$^{-1}$: 2934 (br), 1598 (m), 1576 (w), 1476 (s), 1421 (m), 1323 (m), 1268 (m), 1028 (w), 826 (w). HRMS-CI(m/z): [M+H]$^+$ calcd for C$_{17}$H$_{19}$N$_2$O, 267.1492; found, 267.1492.

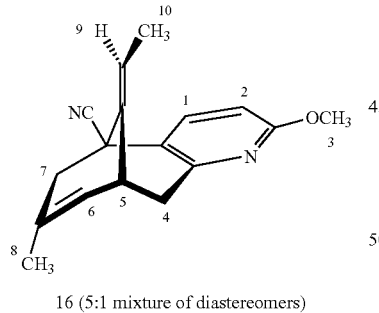

16 (5:1 mixture of diastereomers)

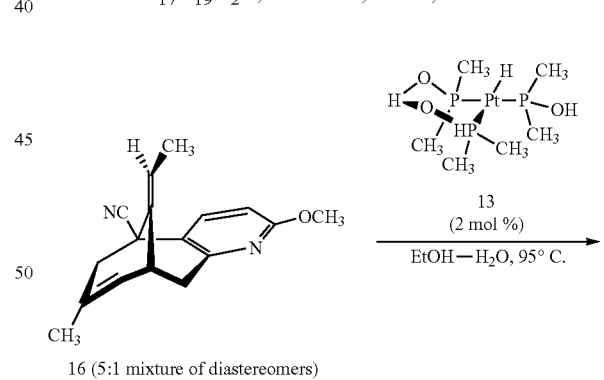

16 (5:1 mixture of diastereomers)

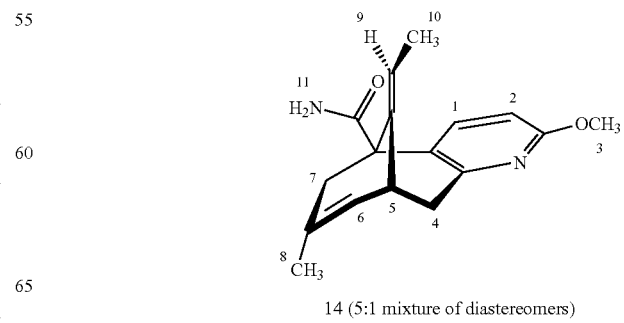

14 (5:1 mixture of diastereomers)

Step 3c: Hydrolysis of the Nitrile 16 (Amide 14)

Hydrido(hydroxydimethylphosphino)[hydrogenbis(hydroxydimethylphosphino)]platinum (II) (13, 101 mg, 240 µmol, 0.02 equiv) was added to a solution of the unpurified nitrile 16 (11.8 mmol, 1.00 equiv, assuming quantitative yield in the preceeding step) in ethanol (6.6 mL) and water (3.3 mL) at 24° C. The resulting mixture was placed in an oil bath that had been preheated to 95° C. The reaction mixture was stirred and heated for 24 h at 95° C. The product mixture was cooled over 10 min to 24° C. The cooled mixture was concentrated to dryness. The residue obtained was dissolved in dichloromethane (15 mL) and chloroform (15 mL), and the resulting solution was filtered through a pad of sodium sulfate. The filtrate was concentrated to afford the amide 14 as an off-white solid (3.60 g). $^1$H NMR analysis (400 MHz, CDCl$_3$) indicated >95% conversion to the amide 14. The product so obtained was used directly in the following step. An analytically pure sample of the amide 14 was obtained by flash-column chromatography (eluting with 50% ethyl acetate-hexanes):

$R_f$=0.20 (50% ethyl acetate-hexanes, KMnO$_4$). $^1$H NMR (500 MHz, CDCl$_3$, 5:1 mixture of diastereomers): E-olefin (major diastereomer), δ 7.33 (d, 1H, J=8.5 Hz, H$_1$), 6.57 (d, 1H, J=8.5 Hz, H$_2$), 5.62 (br s, 1H, H$_{11}$), 5.40 (q, 1H, J=7.0 Hz, H$_9$), 5.38-5.35 (m, 1H, H$_6$), 5.17 (br s, 1H, H$_{11}$), 3.90 (s, 3H, H$_3$), 3.60 (m, 1H, H$_5$), 3.09-3.01 (m, 2H, H$_4$/H$_7$), 2.88 (d, 1H, J=16.5 Hz, H$_4$), 2.11 (d, 1H, J=17.5 Hz, H$_7$), 1.70 (d, 3H, J=7.0 Hz, H$_{10}$), 1.53 (s, 3H, H$_8$); Z-olefin (minor diastereomer), δ 7.37 (d, 1H, J=8.4 Hz, H$_1$), 6.58 (d, 1H, J=8.4 Hz, H$_2$), 5.58 (br s, 1H, H$_{11}$), 5.54 (q, 1H, J=16.5 Hz, H$_9$), 5.38-5.35 (m, 1H, H$_6$), 5.30 (br s, 1H, H$_{11}$), 3.90 (s, 3H, H$_3$), 3.15-3.01 (m, 3H, H$_4$/H$_5$/H$_7$), 2.83 (d, 1H, J=16.5 Hz, H$_4$), 2.18 (d, 1H, J=17.0 Hz, H$_7$), 1.73 (d, 3H, J=7.5 Hz, H$_{10a}$), 1.53 (s, 3H, H$_8$); $^{13}$C NMR (125 MHz, CDCl$_3$, 5:1 mixture of diastereomer): E-olefin (major diastereomer), δ 176.9 (C), 162.9 (C), 153.8 (C), 138.9 (CH), 138.1 (C), 133.7 (C), 128.5 (C), 124.1 (CH), 115.3 (CH), 108.9 (CH), 54.4 (C), 53.7 (CH$_3$), 45.3 (CH$_2$), 39.8 (CH$_2$), 33.0 (CH), 23.0 (CH$_3$), 13.0 (CH$_3$); Z-olefin (minor diastereomer), δ 178.4 (C), 162.9 (C), 153.1 (C), 138.5 (CH), 137.1 (C), 133.6 (C), 128.3 (C), 125.9 (CH), 117.5 (CH), 109.2 (CH), 53.7 (CH$_3$), 51.2 (C), 45.1 (CH$_2$), 44.2 (CH), 39.7 (CH$_2$), 23.0 (CH$_3$), 13.0 (CH$_3$). IR (ATR-FTIR), cm$^{-1}$: HRMS-CI (m/z): 3346 (br), 2926 (br), 1710 (w), 1664 (s), 1597 (m), 1576 (w), 1475 (s), 1422 (m), 1322 (m), 1267 (w), 1028 (m), 824 (w). [M+H]$^+$ calcd for C$_{17}$H$_{21}$N$_2$O$_2$, 285.1598; found, 285.1601.

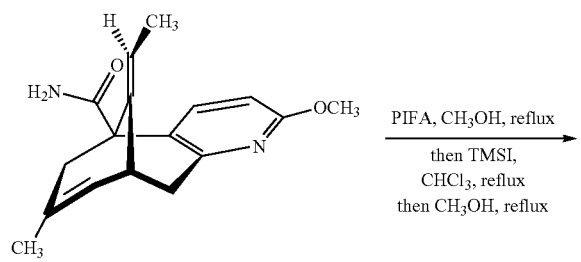

14 (5:1 mixture of diastereomers)

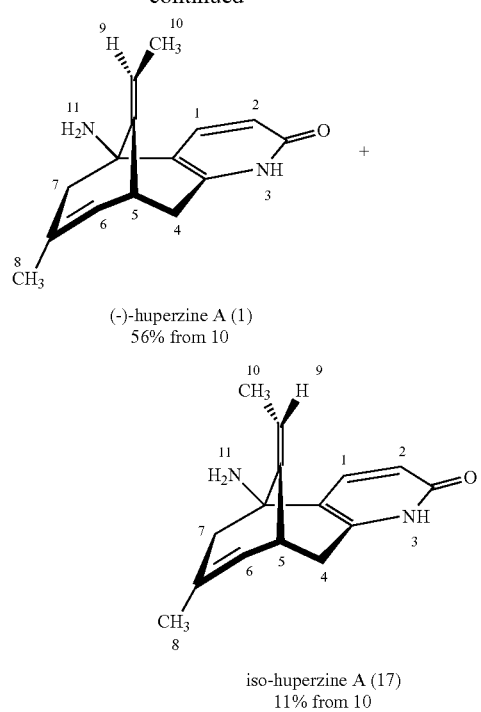

(−)-huperzine A (1)
56% from 10 iso-huperzine A (17)
11% from 10

Step 3d: Conversation of the Amide 14 to (−)-Huperzine A (1)

[Bis(trifluoroacetoxy)iodo]benzene (5.58 g, 13.0 mmol, 1.10 equiv) was added to a stirred solution of the unpurified amide 14 (11.8 mmol, 1.00 equiv, assuming quantitative yield in the preceeding step) in methanol (240 mL). The resulting mixture was heated to reflux (bath temperature=65° C.). The reaction mixture was stirred and heated for 2 h at 65° C. The product mixture was cooled over 30 min to 24° C. The cooled mixture was concentrated to dryness. The residue obtained was dissolved in chloroform (120 mL). Iodotrimethylsilane (8.40 mL, 59.0 mmol, 5.00 equiv) was added, and the reaction mixture was heated to reflux (bath temperature=61° C.). The reaction mixture was stirred and heated for 3 h at 61° C. The mixture was then cooled over 30 min to 24° C. Methanol (120 mL) was added and the resulting mixture was heated to reflux (bath temperature=65° C.). The reaction mixture was stirred and heated for 12 h at 65° C. The product mixture was then cooled over 30 min to 24° C. The cooled product mixture was concentrated to dryness. The residue obtained was dissolved in 50% dichloromethane-chloroform (v/v, 200 mL). The resulting solution was transferred to a separatory funnel that had been charged with 1.0 N aqueous sulfuric acid solution (200 mL). The layers that formed were separated. The aqueous layer was then extracted with 50% dichloromethane-chloroform (v/v, 2×200 mL). The organic layers were combined and discarded. The aqueous layer was basified with saturated aqueous ammonium hydroxide solution (100 mL, final pH=12-13). The basified aqueous layer was extracted with 50% dichloromethane-chloroform (v/v, 4×200 mL). The organic layers were combined and the combined organic layers were dried over sodium sulfate. The dried solution was filtered and the filtrate was concentrated. The residue obtained was purified by flash-column chromatography (eluting with 10% methanol-ethyl acetate) to yield (−)-huperzine A (1, 1.61 g, 56%, off-white solid) and the olefin isomer (iso-huperzine A, 17, 310 mg, 11%, off-white solid).

Synthetic (−)-huperzine A (1) was identical in all respects [$^1$H NMR, $^{13}$C NMR, LC/MS retention time, IR, TLC solvent systems (10% methanol-ethyl acetate, 5% methanol-dichloromethane, 5% methanol-dichloromethane+1% ammonium hydroxide) and optical rotation] to an authentic sample.

(−)-huperzine A (1): $R_f$=0.15 (10% methanol-ethyl acetate, KMnO$_4$). $t_R$=0.91. $[\alpha]^{20}{}_n$ −144 (c 0.23, CHCl$_3$), lit. $[\alpha]^{20}{}_n$=−150 (c 0.12, CHCl$_3$).$^{10}$ $^1$H NMR (500 MHz, CDCl$_3$), δ 13.25 (br s, 1H, H$_3$), 7.88 (d, 1H, J=9.5 Hz, H$_1$), 6.37 (d, 1H, J=9.0 Hz, H$_2$), 5.46 (q, 1H, J=6.5 Hz, H$_9$), 5.38 (d, 1H, J=4.5 Hz, H$_6$), 3.59-3.55 (m, 1H, H$_5$), 2.86 (dd, 1H, J=17.0, 5.0, H$_4$), 2.73 (dd, 1H, J=16.5, 1.0 Hz, H$_4$), 2.12 (app s, 2H, H$_7$), 1.88 (br s, 2H, H$_{11}$), 1.64 (d, 3H, J=6.5 Hz, H$_{10}$), 1.51 (s, 3H, H$_8$). $^{13}$C NMR (125 MHz, CDCl$_3$), δ 165.5 (C), 143.3 (C), 142.4 (C), 140.3 (CH), 134.1 (C), 124.4 (CH), 122.8 (C), 117.1 (CH), 111.4 (CH), 54.5 (C), 49.2 (CH$_2$), 35.4 (CH$_2$), 33.0 (CH), 22.7 (CH$_3$), 12.5 (CH$_3$). IR (ATR-FTIR), cm$^{-1}$: 3355 (br), 1644 (s), 1608 (s), 1552 (m), 1452 (m), 1121 (m), 837 (m). HRMS-CI(m/z): [M+H]$^+$ calcd for C$_{15}$H$_{19}$N$_2$O, 243.1492; found, 243.1493.

iso-huperzine A (17): $R_f$=0.15 (5% methanol-dichloromethane+1% ammonium hydroxide, KMnO$_4$). $[\alpha]^{20}{}_n$=−121 (c 0.01, CHCl$_3$). $^1$H NMR (400 MHz, CDCl$_3$), δ 13.10 (br s, 1H, H$_3$), 7.86 (d, 1H, J=9.6 Hz, H$_1$), 6.42 (d, 1H, J=9.6 Hz, H$_2$), 5.41 (q, 1H, J=7.2 Hz, H$_9$), 5.37 (br s, 1H, H$_6$), 3.00-2.88 (m, 2H, H$_4$/H$_5$), 2.70 (d, 1H, J=16.0 Hz, H$_4$), 2.40 (d, 1H, J=16.8, H$_7$), 2.05 (d, 1H, H$_7$), 1.93 (d, 3H, J=7.2 Hz, H$_{10}$), 1.90 (br s, 2H, H$_{11}$), 1.53 (s, 3H, H$_8$). $^{13}$C NMR (100 MHz, CDCl$_3$), δ 165.5 (C), 143.4 (C), 140.2 (C), 140.0 (CH), 133.7 (C), 125.4 (CH), 123.0 (C), 117.3 (CH), 115.7 (CH), 56.6 (C), 49.8 (CH$_2$), 44.0 (CH), 36.4 (CH$_2$), 22.6 (CH$_3$), 14.0 (CH$_3$). IR (ATR-FTIR), cm$^{-1}$: 3380 (br), 2909 (br), 1653 (s), 1611 (m), 1551 (m), 1459 (m), 833 (m), 755 (m), 651 (m). HRMS-CI(m/z): [M+H]$^+$ calcd for C$_{15}$H$_{19}$N$_2$O, 243.1492; found, 243.1494.

EXPERIMENTAL SECTION REFERENCES

1. W. C. Still, M. Kahn, A. Mitra, *J. Org. Chem.* 1978, 43, 2923.
2. A. B. Pangborn, M. A. Giardello, R. H. Grubbs, R. K. Rosen, F. J. Timmers, *Organometallics* 1996, 15, 1518.
3. I. Fleming, R. S. Roberts, S. C. Smith *J. Chem. Soc., Perkin Trans. 1* 1998, 1209.
4. H. W. Lee, S. K. Ji, I-Y. C. Lee, J. H. Lee, *J. Org. Chem.* 1996, 61, 2542.
5. S. A. Kelly, Y. Foricher, J. Mann, J. M. Bentley, *Org. Biomol. Chem.* 2003, 1, 2865.
6. C. Dai, G. C. Fu, *J. Am. Chem. Soc.* 2001, 123, 2719.
7. E. M. Burgess, H. R. Penton, E. A. Taylor, *J. Org. Chem.* 1973, 38, 26.
8. T. Ghaffar, A. W. Parkins, *J. Mol. Catal. A* 2000, 160, 249.
9. For clarity, synthetic intermediates not described in the manuscript are numbered in the Supporting Information beginning with 16.
10. F. Yamada, A. P. Kozikowski, E. R. Reddy, Y. P. Pang, J. H. Miller, M. McKinney, *J. Am. Chem. Soc.* 1991, 113, 4695.

BACKGROUND AND DETAILED DESCRIPTION OF THE INVENTION REFERENCES 1. (a) J.-S. Liu, Y.-L. Zhu, C.-M. Yu, Y.-Z. Zhou, Y.-T. Han, F.-W. Wu and B.-F. Qi, Can. J. Chem., 1986, 64, 837. Selected review: (b) A. P. Kozikowski and W. T€uckmantel, Acc. Chem. Res., 1999, 32, 641.
2. (a) Y. E. Wang, D. X. Yue and X. C. Tang, Acta. Pharmacol. Sin., 1986, 7, 110. For the structure of (−)-huperzine A (1) bound to AChE, see: (b) M. L. Raves, M. Harel, Y.-P. Pang, I. Silman, A. P. Kozikowski and J. L. Sussman, Nat. Struct. Biol., 1997, 4, 57.
3. (a) G. Lallement, J.-P. Demoncheaux, A. Foquin, D. Baubichon, M. Galonnier, D. Clarenc on and F. Dorandeu, Drug Chem. Toxicol., 2002, 25, 309; (b) R. Gordon, J. Haigh, G. Garcia, S. Feaster, M. Riel, D. Lenz, P. Aisen and B. Doctor, Chem.-Biol. Interact., 2005, 157-158, 239; (c) J. Haigh, S. Johnston, A. Peppernay, P. Mattern, G. Garcia, B. Doctor, R. Gordon and P. Aisen, Chem.-Biol. Interact., 2008, 175, 380; (d) J. Z. Karasova, J. Bajgar, L. Novotny and K. Kuca, Lett. Drug Des. Discovery, 2009, 6, 563. For a review, see: (e) G. Lallement, V. Baille, D. Baubichon, P. Carpentier, J.-M. Collombet, P. Filliat, A. Foquin, E. Four, C. Masqueliez, G. Testylier, L. Tonduli and F. Dorandeu, NeuroToxicology, 2002, 23, 1.
4. For selected reviews, see: (a) D. L. Bai, X. C. Tang and X. C. He, Curr. Med. Chem., 2000, 7, 355; (b) R. Wang, H. Yan and X.-c. Tang, Acta Pharmacol. Sin., 2006, 27, 1; (c) H. Y. Zhang and X. C. Tang, Trends Pharmacol. Sci., 2006, 27, 619; (d) H. Y. Zhang, C. Y. Zheng, H. Yan, Z. F. Wang, L. L. Tang, X. Gao and X. C. Tang, Chem.-Biol. Interact., 2008, 175, 396.
5. J. T. Little, S. Walsh and P. S. Aisen, Expert Opin. Invest. Drugs, 2008, 17, 209.
6. X. Ma, C. Tan, D. Zhu and D. R. Gang, J. Ethnopharmacol., 2006, 104, 54.
7. T. Xi-Can, G. H. Kindel, A. P. Kozikowski and I. Hanin, J. Ethnopharmacol., 1994, 44, 147.
8. Y. Xia and A. P. Kozikowski, J. Am. Chem. Soc., 1989, 111, 4116.
9. L. Qian and R. Ji, Tetrahedron Lett., 1989, 30, 2089.
10. F. Yamada, A. P. Kozikowski, E. R. Reddy, Y. P. Pang, J. H. Miller and M. McKinney, J. Am. Chem. Soc., 1991, 113, 4695.
11. (a) S. Kaneko, T. Yoshino, T. Katoh and S. Terashima, Heterocycles, 1997, 46, 27; (b) S. Kaneko, T. Yoshino, T. Katoh and S. Terashima, Tetrahedron: Asymmetry, 1997, 8, 829; (c) S. Kaneko, T. Yoshino, T. Katoh and S. Terashima, Tetrahedron, 1998, 54, 5471; (d) C. Chassaing, A. Haudrechy and Y. Langlois, Tetrahedron Lett., 1999, 40, 8805; (e) X.-C. He, B. Wang, G. Yu and D. Bai, Tetrahedron: Asymmetry, 2001, 12, 3213; (f) Q.-B. Pan and D.-W. Ma, Chin. J. Chem., 2003, 21, 793.
12. T. Koshiba, S. Yokoshima and T. Fukuyama, Org. Lett., 2009, 11, 5354.
13. J. Ward and V. Caprio, Tetrahedron Lett., 2006, 47, 553.
14. (a) A. Haudrechy, C. Chassaing, C. Riche and Y. Langlois, Tetrahedron, 2000, 56, 3181; (b) I. Y. C. Lee, M. H. Jung, H. W. Lee and J. Y. Yang, Tetrahedron Lett., 2002, 43, 2407; (c) C. Lucey, S. A. Kelly and J. Mann, Org. Biomol. Chem., 2007, 5, 301.
15. The most efficient route to racemic huperzine proceeds in 12 steps and 8.9% overall yield. See, ref. 8 and: A. P. Kozikowski, E. R. Reddy and C. P. Miller, J. Chem. Soc., Perkin Trans. 1, 1990, 195.
16. (a) H. W. Lee, S. K. Ji, I.-Y. C. Lee and J. H. Lee, J. Org. Chem., 1996, 61, 2542; (b) F. Bertozzi, P. Crotti, B. L. Feringa, F. Macchia and M. Pineschi, Synthesis, 2001, 483; (c) R. Naasz, L. A. Arnold, A. J. Minnaard and B. L. Feringa, Angew. Chem., Int. Ed., 2001, 40, 927.
17. V. Bisai and R. Sarpong, Org. Lett., 2010, 12, 2551.

18. D. Kahne and D. B. Collum, Tetrahedron Lett., 1981, 22, 5011.
19. (a) M. Kawatsura and J. F. Hartwig, J. Am. Chem. Soc., 1999, 121, 1473; (b) J. M. Fox, X. Huang, A. Chieffi and S. L. Buchwald, J. Am. Chem. Soc., 2000, 122, 1360. For a review, see: (c) F. Bellina and R. Rossi, Chem. Rev., 2010, 110, 1082.
20. C. Dai and G. C. Fu, J. Am. Chem. Soc., 2001, 123, 2719.
21. See A. B. Reitz, S. O. Nortey, A. D. Jordan, Jr., M. S. Mutter and B. E. Maryanoff, J. Org. Chem., 1986, 51, 3302 and references therein.
22. T. Ghaffar and A. W. Parkins, J. Mol. Catal. A: Chem., 2000, 160, 249.

What is claimed is:

1. A compound according to the chemical structure:

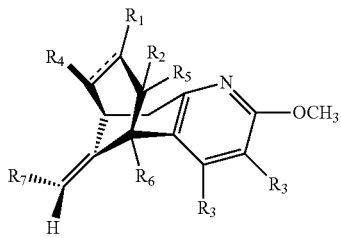

wherein:
$R_1$ is a methyl group;
$R_2$ and $R_5$ are each independently selected from the group consisting of H and methyl;
$R_3$ at each occurrence is H or methyl;
$R_4$ is selected from the group consisting of H, OH, and $Si(CH_3)_2Ph$;
$R_6$ is selected from the group consisting of —C(O)NH$_2$ or CN; and
$R_7$ is methyl; or
a pharmaceutically acceptable salt, enantiomer or diastereomer thereof.

2. The compound according to claim 1 wherein $R_2$ and $R_5$ are each H.

3. The compound according to claim 2 wherein $R_4$ is OH.

4. The compound according to claim 2 wherein $R_4$ is H.

5. The compound according to claim 2 wherein $R_4$ is $Si(CH_3)_2Ph$.

6. A compound according to the chemical structure:

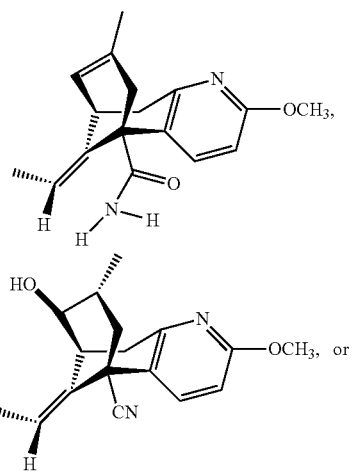

-continued

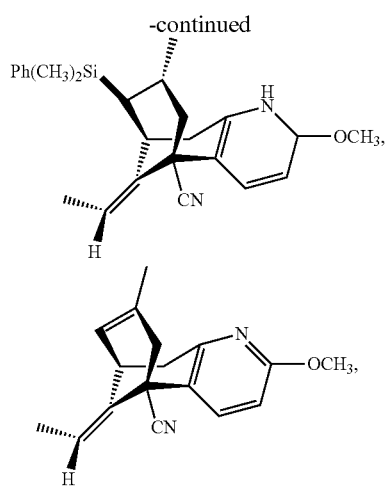

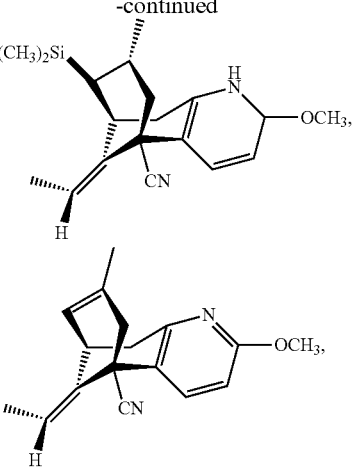

or
a pharmaceutically acceptable salt, enantiomer or diastereomer thereof.

7. The compound of claim 6 according to the chemical structure:

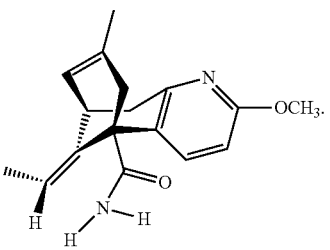

8. The compound of claim 6 according to the chemical structure:

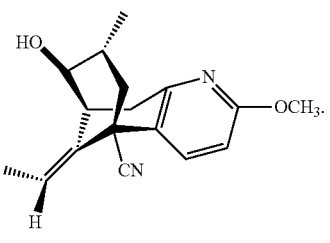

9. The compound of claim 6 according to the chemical structure:

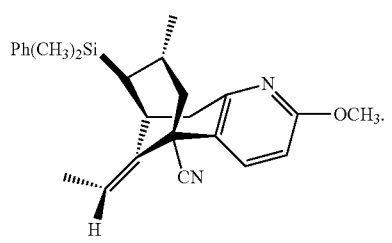

10. The compound of claim 6 according to the chemical structure:

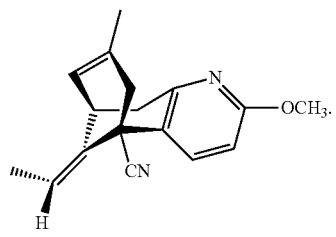
* * * * *